US012727860B2

(12) United States Patent
Keshavarz Motamed et al.

(10) Patent No.: US 12,727,860 B2
(45) Date of Patent: Sep. 8, 2026

(54) DOPPLER-BASED NON-INVASIVE COMPUTATIONAL DIAGNOSTIC METHOD FOR PERSONALIZED CARDIOLOGY

(71) Applicant: McMaster University, Hamilton (CA)

(72) Inventors: Zahra Keshavarz Motamed, Ancaster (CA); Nikrouz Bahadormanesh, Hamilton (CA)

(73) Assignee: McMaster University, Hamilton (CA)

( * ) Notice: Subject to any disclaimer, the term of this patent is extended or adjusted under 35 U.S.C. 154(b) by 91 days.

(21) Appl. No.: 18/703,488

(22) PCT Filed: Oct. 21, 2022

(86) PCT No.: PCT/CA2022/051562
§ 371 (c)(1),
(2) Date: Apr. 22, 2024

(87) PCT Pub. No.: WO2023/065048
PCT Pub. Date: Apr. 27, 2023

(65) Prior Publication Data

US 2024/0407761 A1 Dec. 12, 2024

Related U.S. Application Data

(60) Provisional application No. 63/262,908, filed on Oct. 22, 2021, provisional application No. 63/262,902, filed on Oct. 22, 2021.

(51) Int. Cl.
*A61B 8/00* (2006.01)
*A61B 8/08* (2006.01)

(52) U.S. Cl.
CPC ............ *A61B 8/488* (2013.01); *A61B 8/0883* (2013.01); *A61B 8/0891* (2013.01); *A61B 8/5246* (2013.01); *A61B 2576/023* (2013.01)

(58) Field of Classification Search
None
See application file for complete search history.

(56) References Cited

U.S. PATENT DOCUMENTS 9,167,974 B2 10/2015 Taylor
2016/0140730 A1* 5/2016 Falahatpisheh ...... A61B 8/0883 382/128

(Continued)

FOREIGN PATENT DOCUMENTS

WO 2018108276 A1 6/2018

OTHER PUBLICATIONS

International Search Report & Written Opinion dated Jan. 30, 2023 issued in corresponding PCT International Application No. PCT/CA2022/051562 issued from the Canadian Intellectual Property Office.

(Continued)

*Primary Examiner* — Jonathan Cwern
(74) *Attorney, Agent, or Firm* — SMART & BIGGAR LP; Stephen Beney; Sunil R. Rao

(57) ABSTRACT

Described is a Doppler-based non-invasive computational diagnostic method for personalized cardiology of subjects (e.g., patients with valvular diseases in both pre and post intervention status). The method may be performed for determining dynamic behavior of an aortic valve of the subject, the aortic valve having multiple asymmetric valve leaflets. The method includes receiving Doppler echocardiography images of the subject; processing the received images to reconstruct a 3D geometry of the valve leaflets; determining transient pressure boundary conditions for the valve leaflets using a lumped parameter model specific to the subject; performing a first finite element simulation to determine one or more geometrical parameters for the valve leaflets; iteratively calibrating initial value of one or more material parameters for the subject; and performing a second (Continued)

finite element simulation, based on the calibrated one or more material parameters, to determine an indicator of the dynamic behavior of the aortic valve.

15 Claims, 36 Drawing Sheets

(56) References Cited

U.S. PATENT DOCUMENTS

| | | | | |
|---|---|---|---|---|
| 2016/0171766 | A1* | 6/2016 | Grbic | A61B 17/00 345/423 |
| 2016/0228190 | A1* | 8/2016 | Georgescu | A61B 34/10 |

OTHER PUBLICATIONS

"A diagnostic, monitoring, and predictive tool for patients with complex valvular, vascular and ventricular diseases", Keshavarz-Motamed Z., Sci Rep 2020;10:1-19. https://doi.org/10.1038/s41598-020-63728-8.

Amindari A, Saltik L, Kirkkopru K, Yacoub M, Yalcin HC. "Assessment of calcified aortic valve leaflet deformations and blood flow dynamics using fluid-structure interaction modeling". Informatics in Medicine Unlocked 2017;9:191-9. https://doi.org/10.1016/j.imu.2017.09.001.

Dabiri Y, Sack KL, Rebelo N, Wang P, Wang Y, Choy JS, et al. "Method for Calibration of Left Ventricle Material Properties Using Three-Dimensional Echocardiography Endocardial Strains". Journal of Biomechanical Engineering 2019;141. https://doi.org/10.1115/1.4044215.

Alqahtani AM, Boczar KE, Kansal V, Chan K, Dwivedi G, Chow BJW. "Quantifying Aortic Valve Calcification using Coronary Computed Tomography Angiography". Journal of Cardiovascular Computed Tomography 2017;11:99-104. https://doi.org/10.1016/j.jcct.2017.01.007.

Auricchio F, Conti M, Morganti S, Reali A. "Simulation of transcatheter aortic valve implantation: a patient-specific finite element approach". Comput Methods Biomech Biomed Engin 2014;17:1347-57. https://doi.org/10.1080/10255842.2012.746676.

Morganti S, Auricchio F, Benson DJ, Gambarin FI, Hartmann S, Hughes TJR, et al. "Patient-specific isogeometric structural analysis of aortic valve closure". Computer Methods in Applied Mechanics and Engineering 2015;284:508-20. https://doi.org/10.1016/j.cma.2014.10.010.

Labrosse MR, Beller CJ, Boodhwani M, Hudson C, Sohmer B. "Subject-specific finite-element modeling of normal aortic valve biomechanics from 3D+t TEE images". Medical Image Analysis 2015;20:162-72. https://doi.org/10.1016/j.media.2014.11.003.

Kim HS. "Nonlinear multi-scale anisotropic material and structural models for prosthetic and native aortic heart valves". PhD Thesis. Georgia Institute of Technology, 2009.

Maleki H, Shahriari S, Durand LG, Labrosse MR, Kadem L. "A metric for the stiffness of calcified aortic valves using a combined computational and experimental approach". Med Biol Eng Comput 2014;52:1-8. https://doi.org/10.1007/s11517-013-1113-y.

* cited by examiner

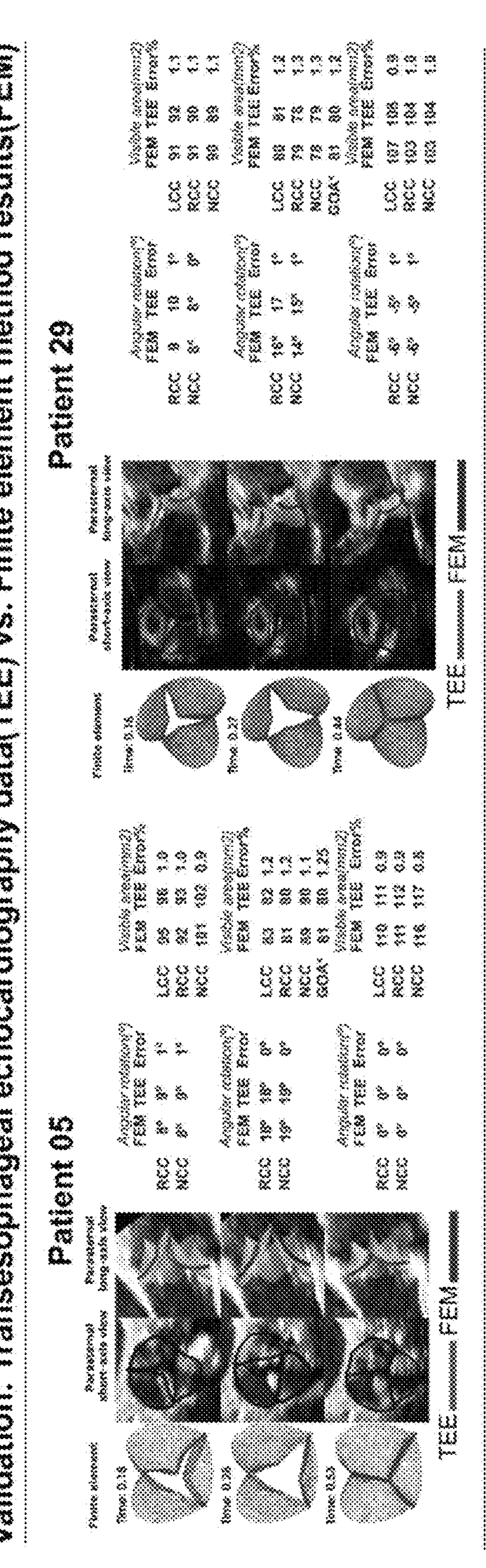
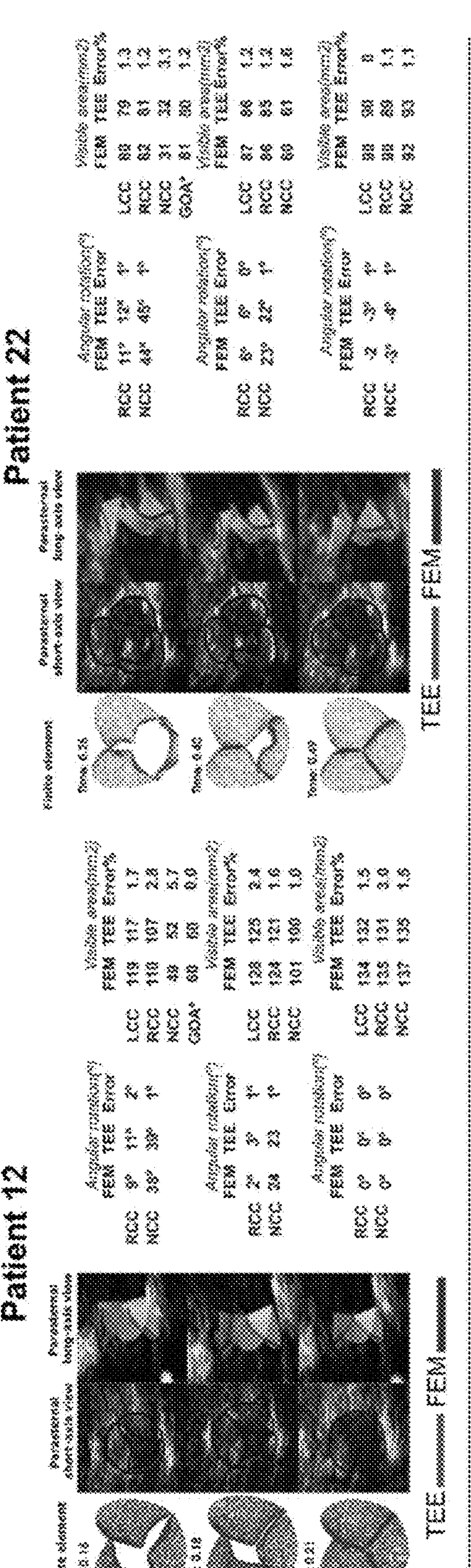
FIG. 4A

Patient #22
(a) Doppler echocardiogrpahy *vs.* Finite element results
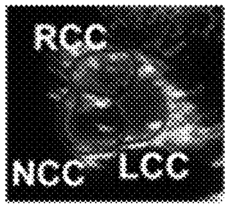
Parasternal short-axis view
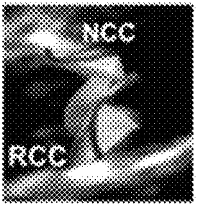
Parasternal long-axis view
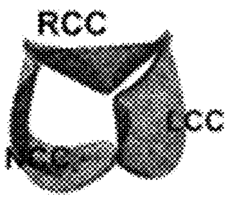
3D Finite Element results
DE FE
(b) Doppler-based calibrated material properties
RCC stiffness (C10=1.0 MPa)
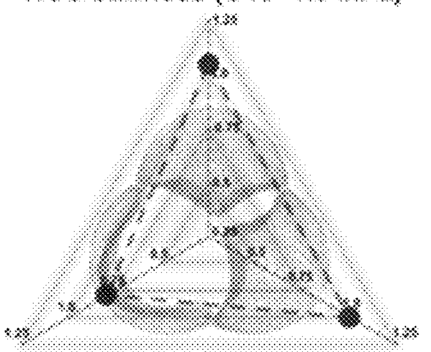
NCC stiffness (C10=0.8 MPa) LCC stiffness (C10=1.0 MPa)
(c) Computed tomography
Described calcified regions in computed tomography
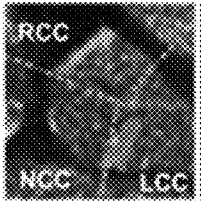
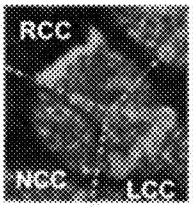
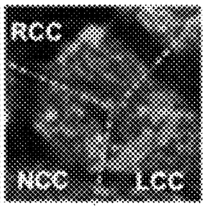
CT axial views
FIG. 6

Patient #23
(a) Doppler echocardiogrpahy *vs.* Finite element results
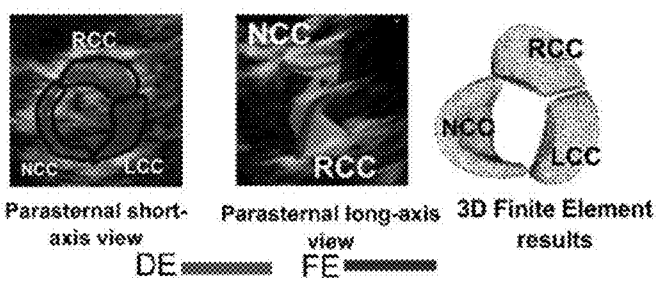
(b) Doppler-based calibrated material properties
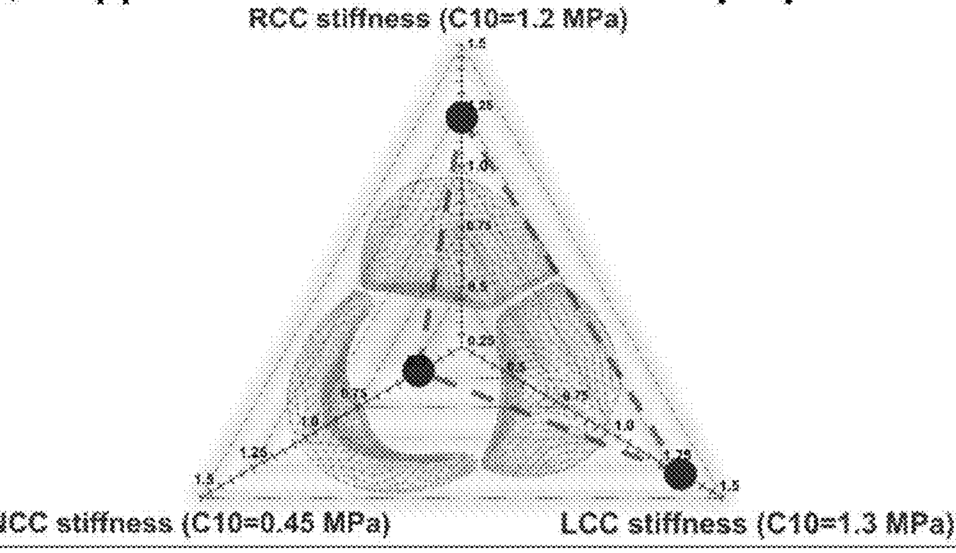
(c) Computed tomography
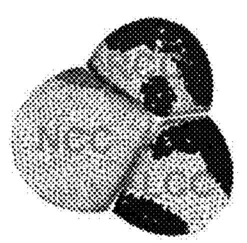
Described calcified regions in computed tomography
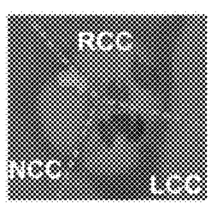
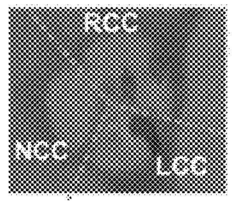
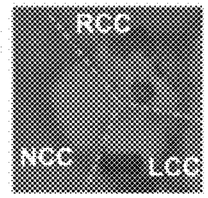
CT axial views
FIG. 8

Patient #29
(a) Doppler echocardiogrpahy *vs.* Finite element results
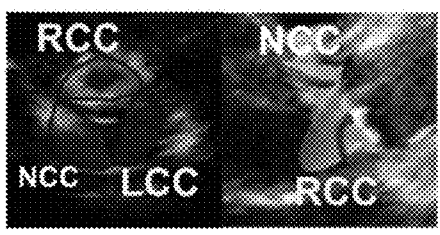
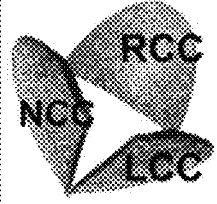
Parasternal short-axis view
Parasternal long-axis view
3D Finite Element results
DE FE
(b) Doppler-based calibrated material properties
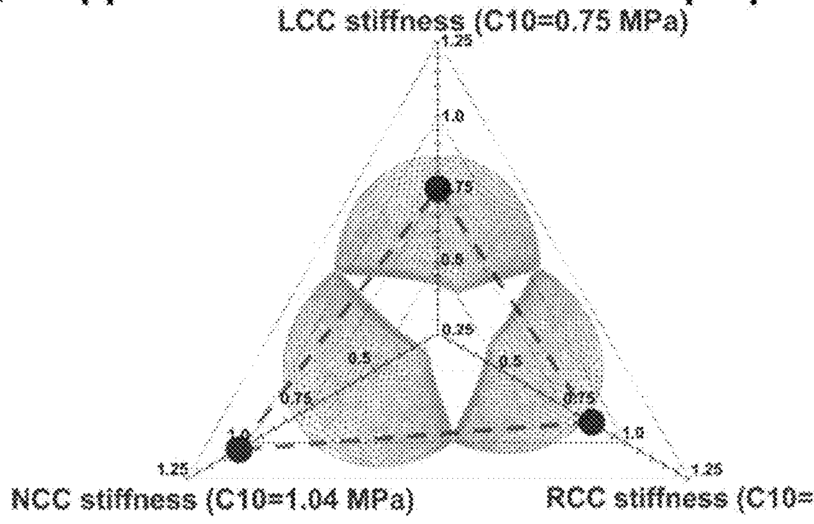
(c) Computed tomography
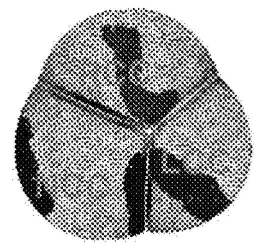
Described calcified regions in computed tomography
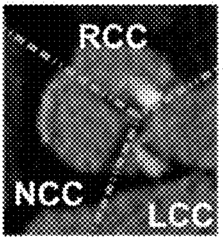
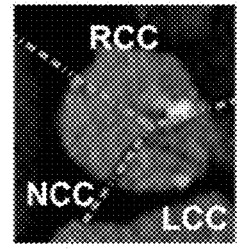
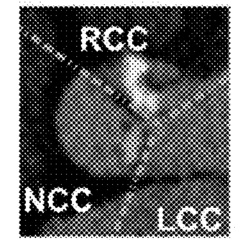
CT axial views
FIG. 10

Validation: Transesophageal echocardiography data vs. Finite element modeling results
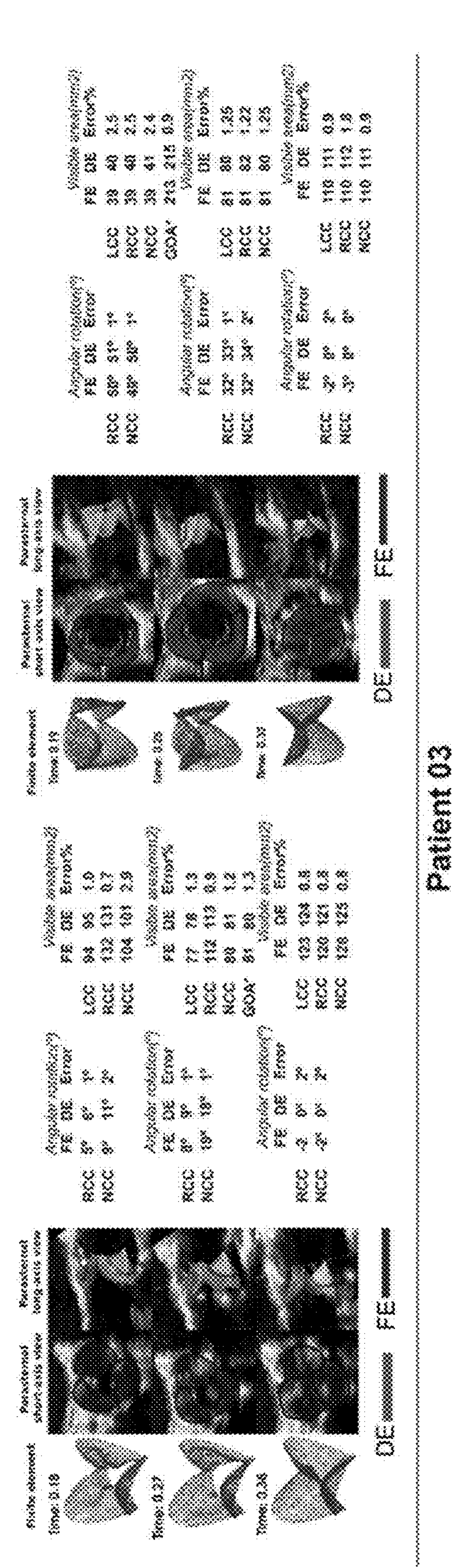
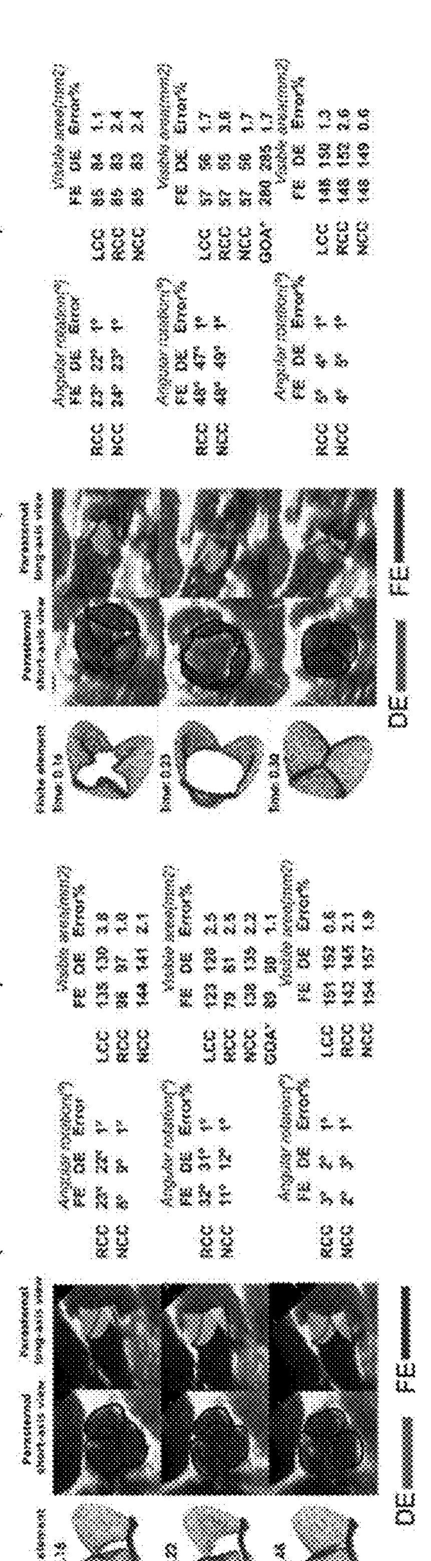
FIG. 13B 3-D leaflets motion and Von Mises stress (MPa) in Patient #3

Figure 14:
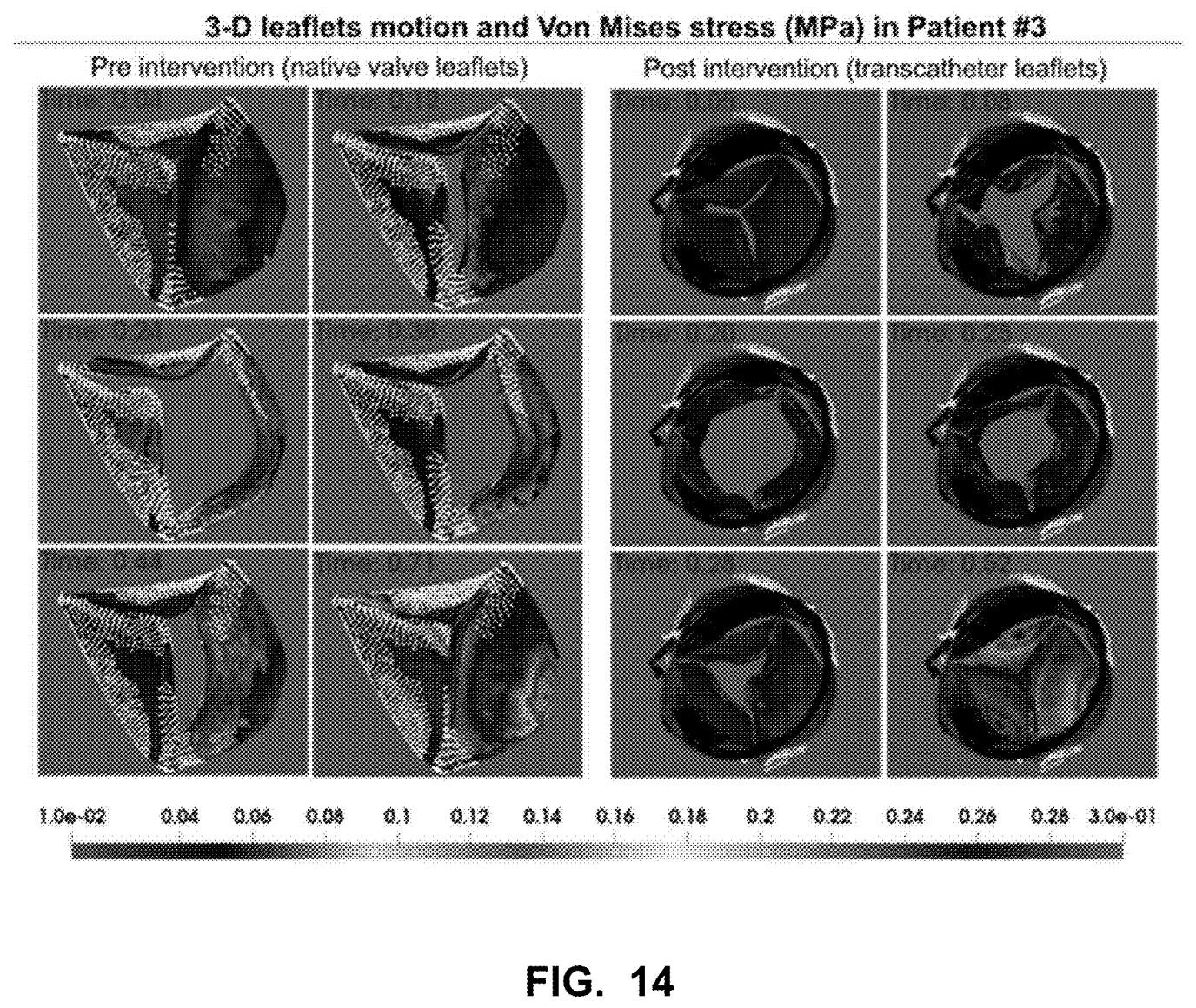

Pre intervention (native valve leaflets)

Post intervention (transcatheter leaflets)

Patient #03

(a) Doppler Echocardiogrpahy/Computed Tomography/Finite Element results

Pre intervention (native valve leaflets) Post intervention (transcatheter leaflets)

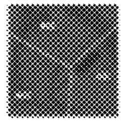
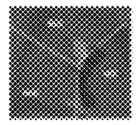
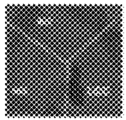
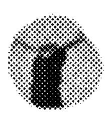
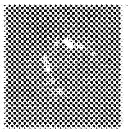
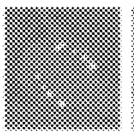
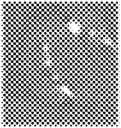

CT axial views CT axial views

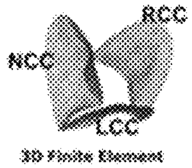

3D Finite Element results

Parasternal short-axis view

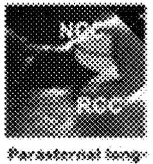

Parasternal long-axis view

3D Finite Element results

Parasternal short-axis view

Parasternal long-axis view

DE FE DE FE (b) Time-averaged maximum principal stress during full cardiac cycle (MPa)

Pre intervention (native valve leaflets) Post intervention (transcatheter leaflets)

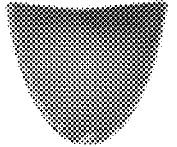

Left-coronary cusp

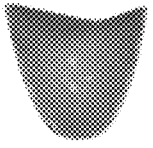

Non-coronary cusp

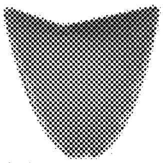

Right-coronary cusp

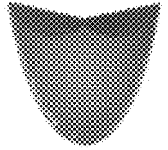

Left-coronary cusp

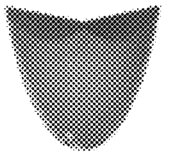

Non-coronary cusp

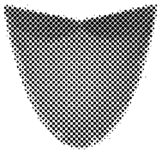

Right-coronary cusp

-1.0e-01 -0.05 0 0.05 0.1 0.15 0.2 0.25 0.3 0.35 0.4 0.45 0.5 0.55 6.1e-01

(c) Leaflet stiffness and valve performance

Pre intervention (native valve leaflets) Post intervention (transcatheter leaflets)

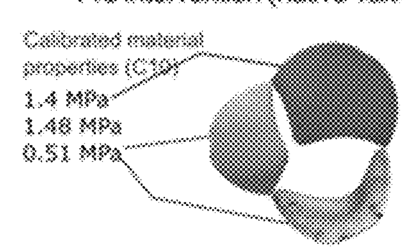

0.34 Ejection time (seconds)

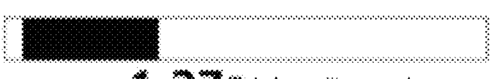

1.27 Total cardiac cycle duration (seconds)

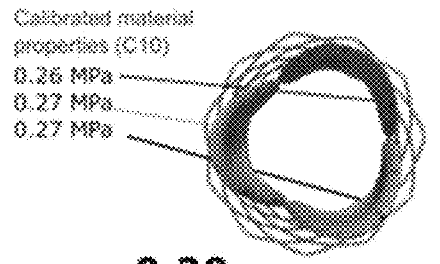

0.29 Ejection time (seconds)

0.75 Total cardiac cycle duration (seconds)

FIG. 16

Figure 17:
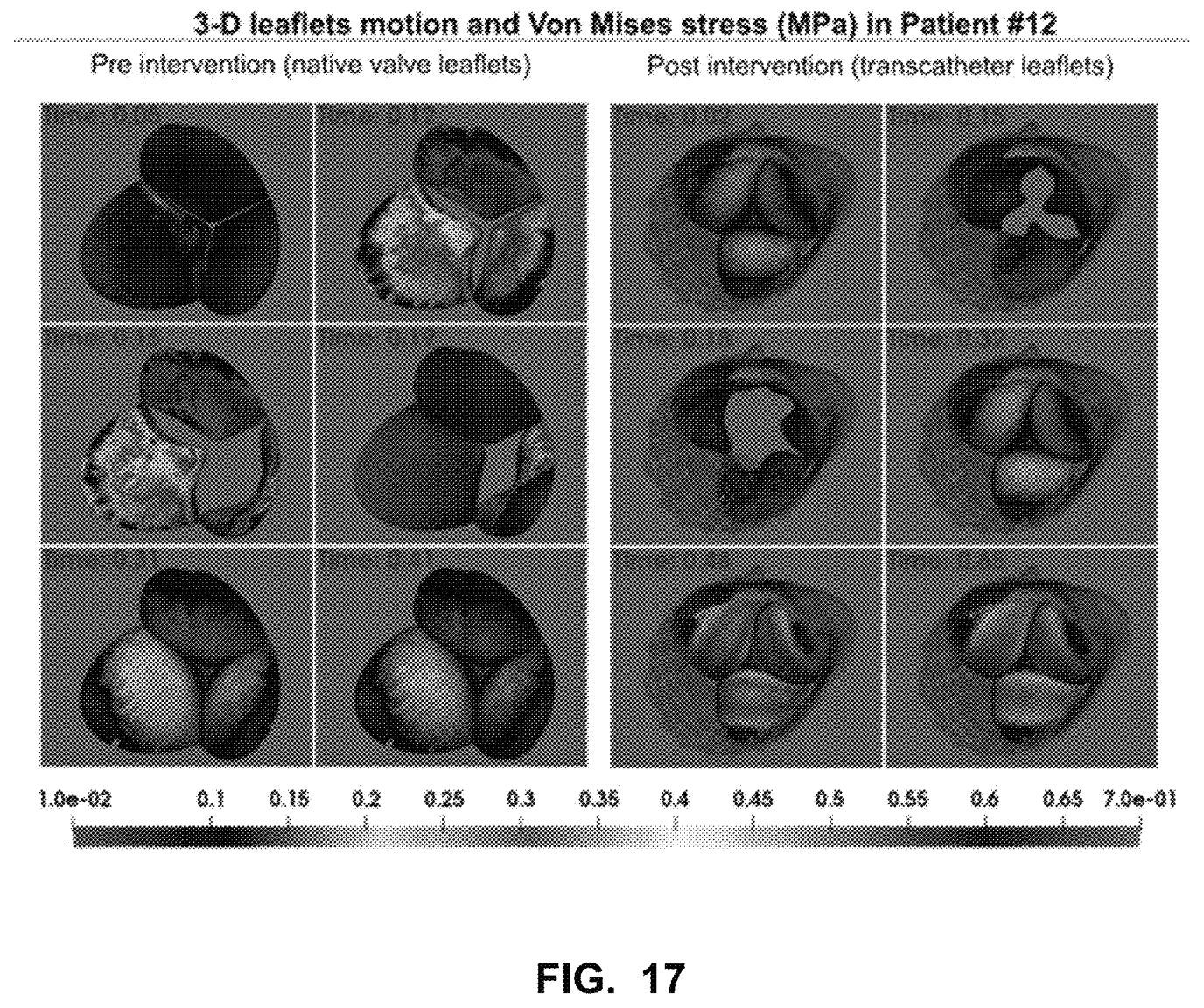

3-D leaflets motion and Von Mises stress (MPa) in Patient #12

Pre intervention (native valve leaflets)

Post intervention (transcatheter leaflets)

Patient #12
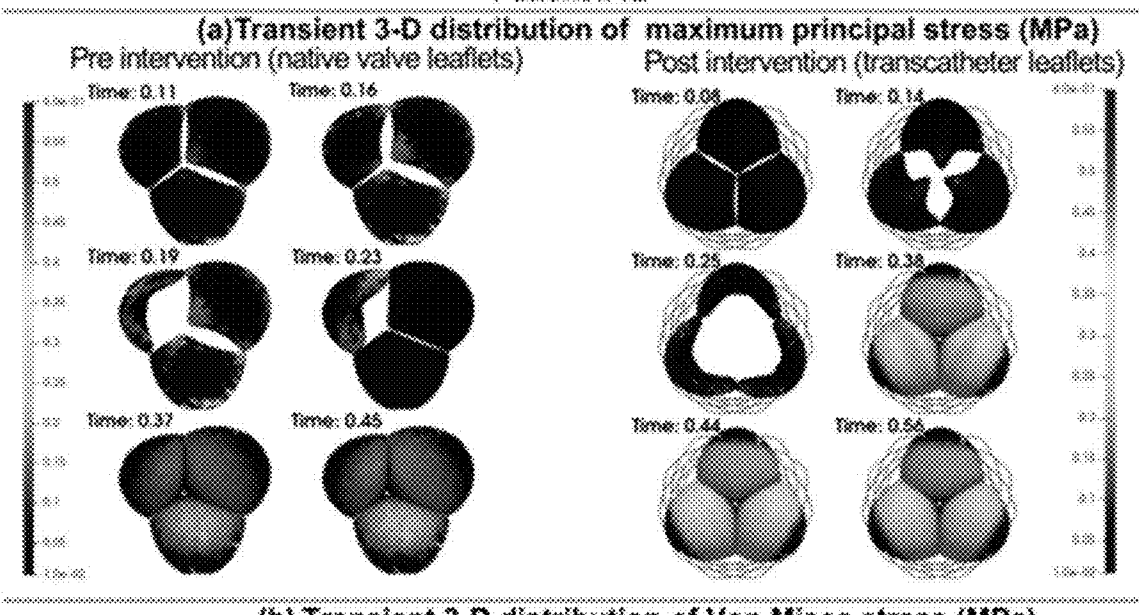
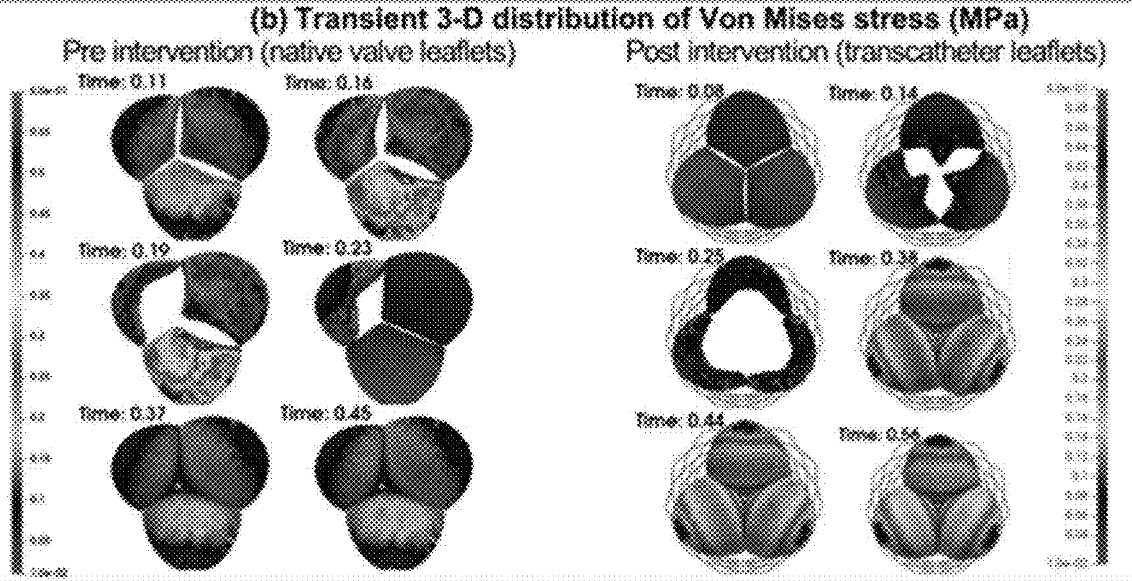
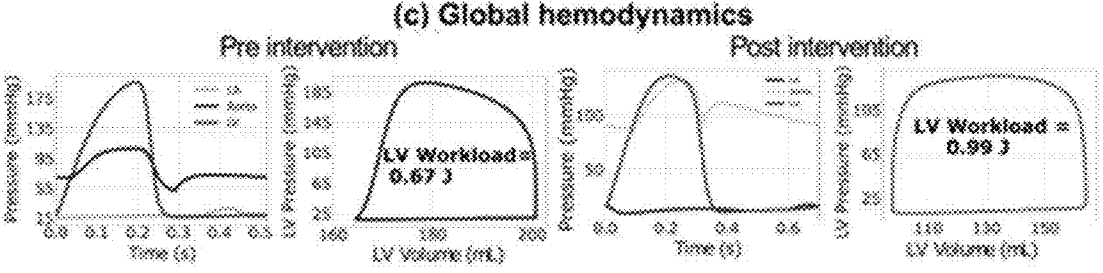
FIG. 18

Patient #12

(a) Doppler Echocardiogrpahy/Computed Tomography/Finite Element results

Pre intervention (native valve leaflets) Post intervention (transcatheter leaflets)

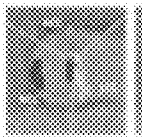
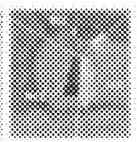
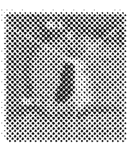
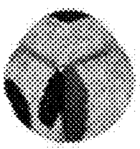
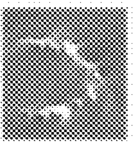
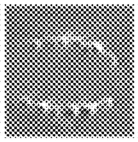
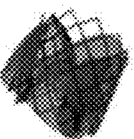

CT axial views CT axial views

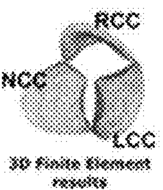

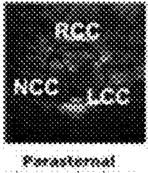

3D Finite Element results / Parasternal short-axis view / Parasternal long-axis view / 3D Finite Element results / Parasternal short-axis view / Parasternal long-axis view

DE FE DE FE (b) Time-averaged maximum principal stress during full cardiac cycle (MPa)

Pre intervention (native valve leaflets) Post intervention (transcatheter leaflets)

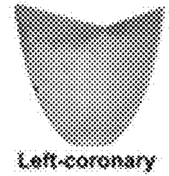
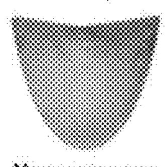
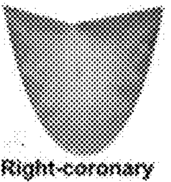
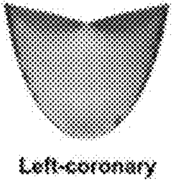
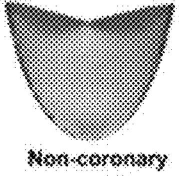

Left-coronary cusp / Non-coronary cusp / Right-coronary cusp / Left-coronary cusp / Non-coronary cusp / Right-coronary cusp -3.0e-01 -0.2 -0.1 0 0.1 0.2 0.3 0.4 0.5 5.6e-01

(c) Leaflet stiffness and valve performance

Pre intervention (native valve leaflets) Post intervention (transcatheter leaflets)

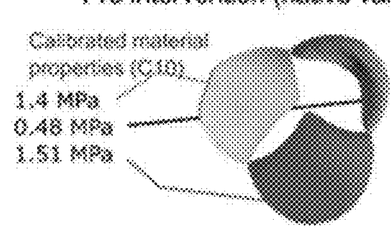

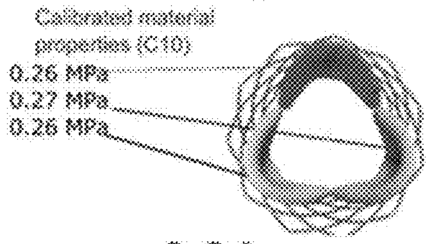

0.25 Ejection time (seconds)

0.51 Total cardiac cycle duration (seconds)

0.24 Ejection time (seconds)

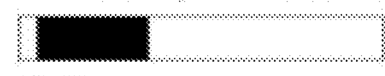

0.7 Total cardiac cycle duration (seconds)

FIG. 19

Patient #16

(a) Doppler Echocardiogrpahy/Computed Tomography/Finite Element results

Pre intervention (native valve leaflets) Post intervention (transcatheter leaflets)

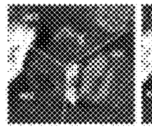
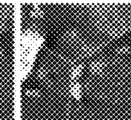
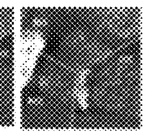

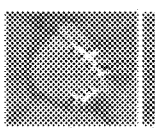
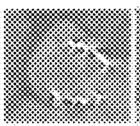

CT axial views

CT axial views

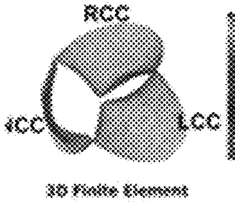

3D Finite Element results

Parasternal short-axis view

Parasternal long-axis view

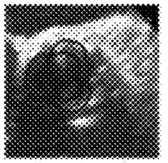

3D Finite Element results

Parasternal short-axis view

Parasternal long-axis view

DE FE

DE FE (b) Time-averaged maximum principal stress during full cardiac cycle (MPa)

Pre intervention (native valve leaflets) Post intervention (transcatheter leaflets)

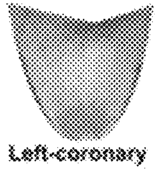

Left-coronary cusp

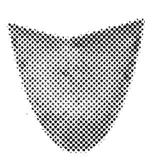

Non-coronary cusp

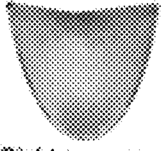

Right-coronary cusp

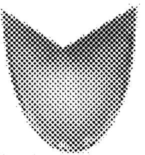

Left-coronary cusp

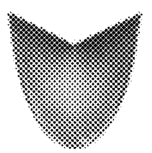

Non-coronary cusp

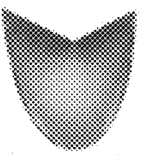

Right-coronary cusp

-1.2e-01 -0.05 0 0.05 0.1 0.15 0.2 0.25 0.3 0.35 4.2e-01

(c) Leaflet stiffness and valve performance

Pre intervention (native valve leaflets) Post intervention (transcatheter leaflets)

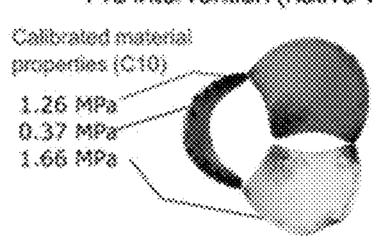

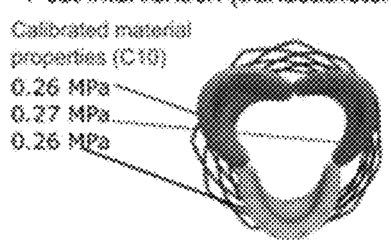

0.37 Ejection time (seconds)

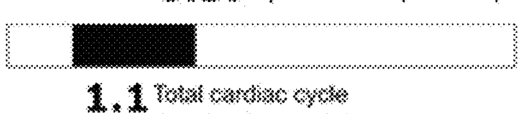

1.1 Total cardiac cycle duration (seconds)

0.31 Ejection time (seconds)

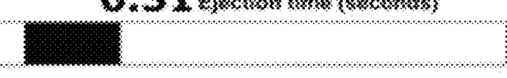

0.9 Total cardiac cycle duration (seconds)

FIG. 22

Figure 23:
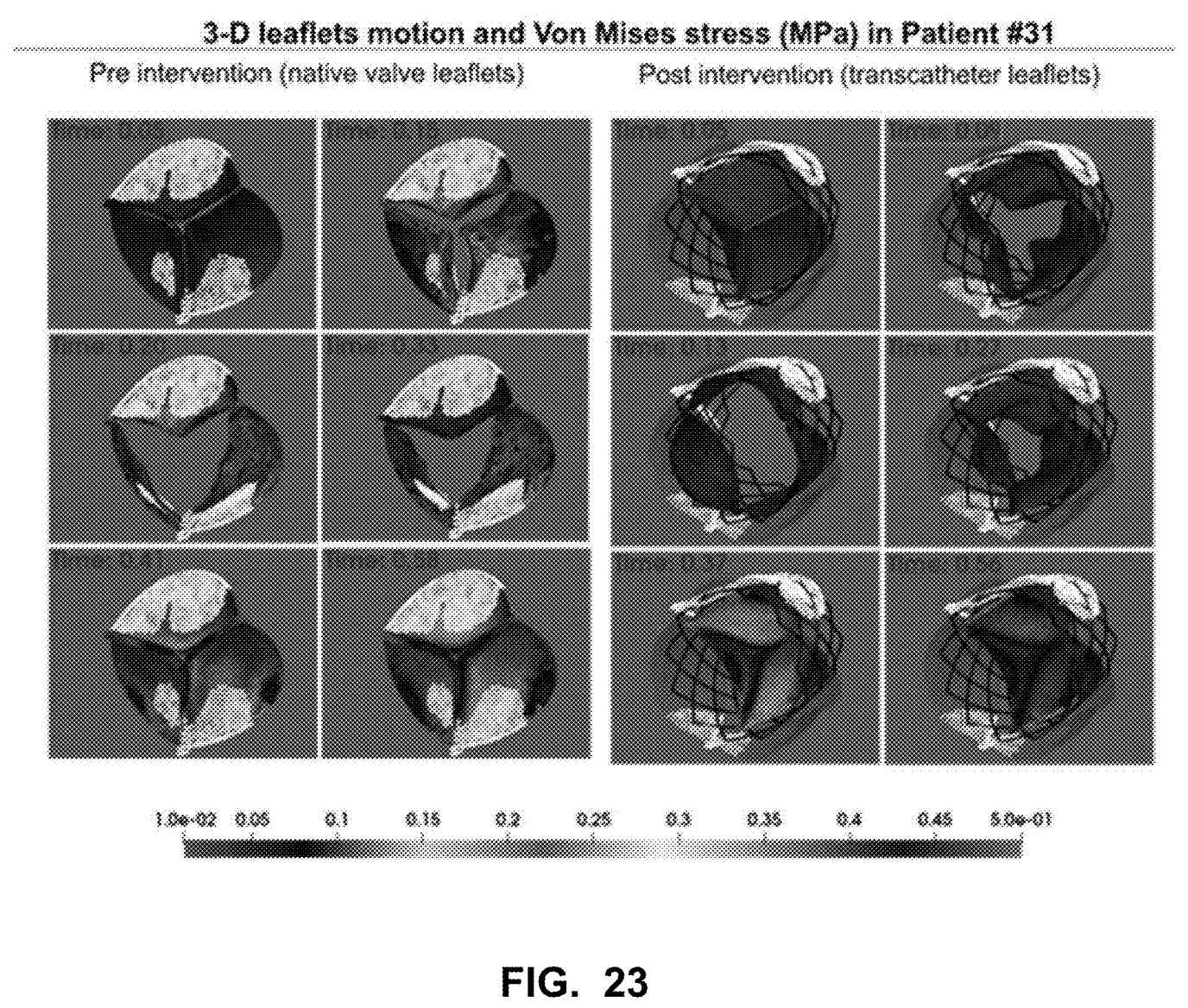

3-D leaflets motion and Von Mises stress (MPa) in Patient #31

Pre intervention (native valve leaflets)

Post intervention (transcatheter leaflets)

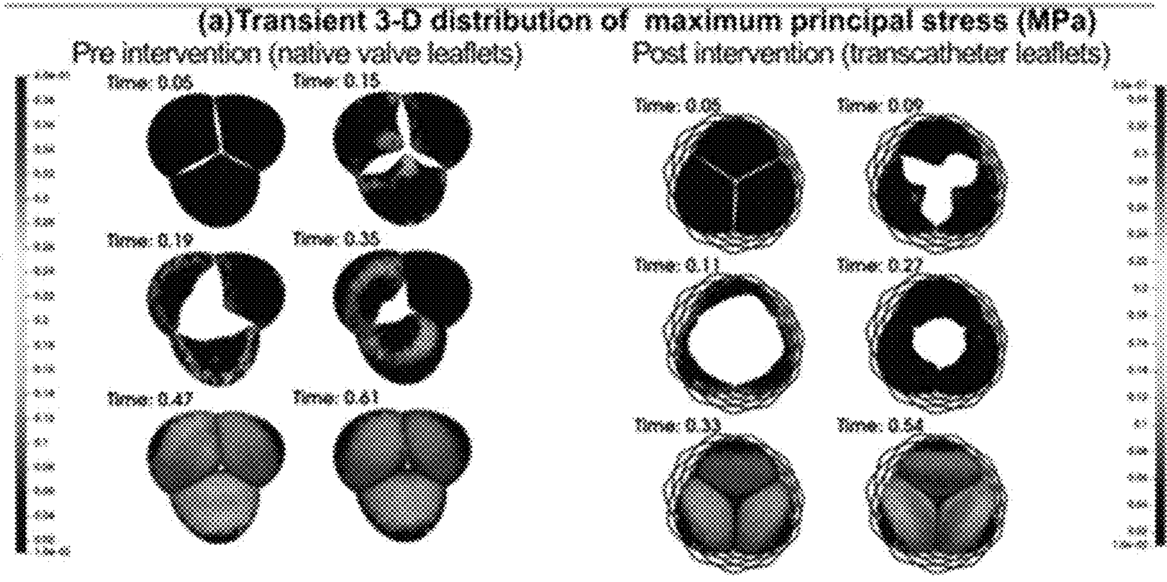
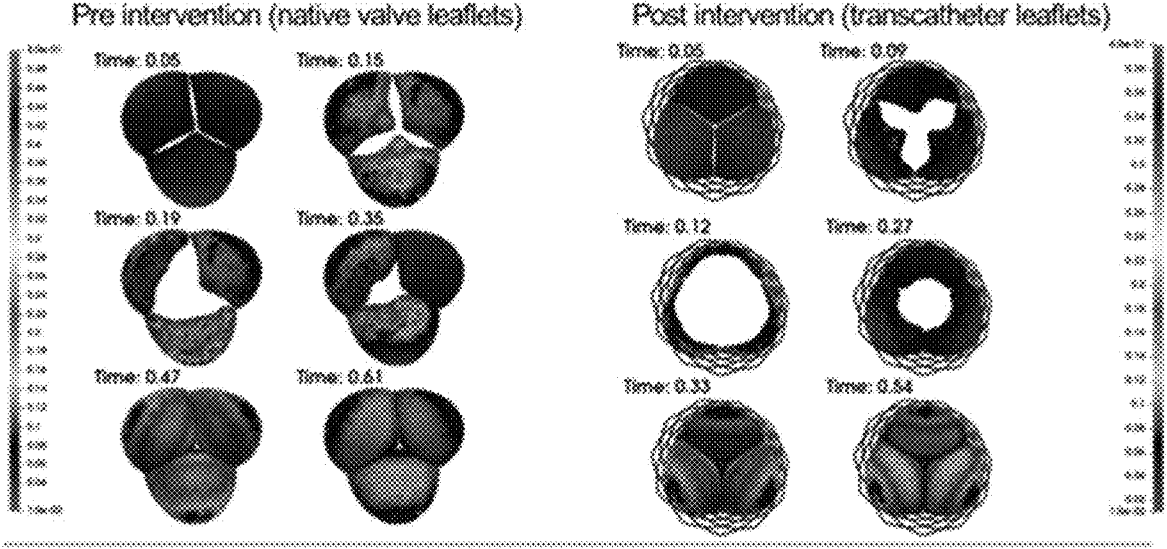
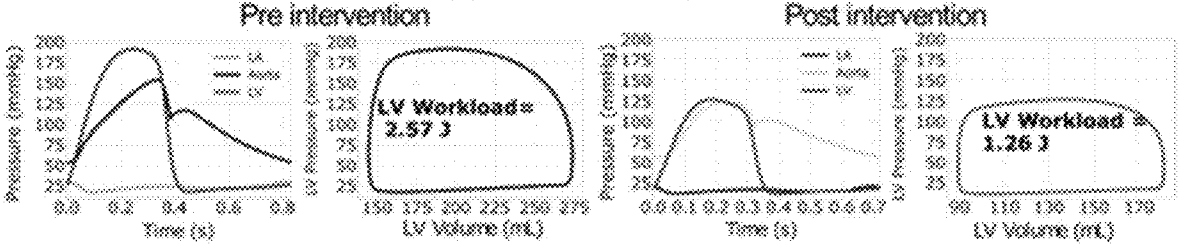
FIG. 24

Patient #31

(a) Doppler Echocardiogrpahy/Computed Tomography/Finite Element results

Pre intervention (native valve leaflets)

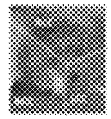
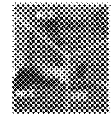
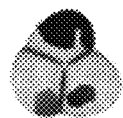

CT axial views

Post intervention (transcatheter leaflets)

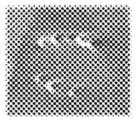
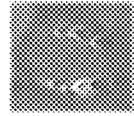
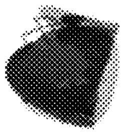

CT axial views

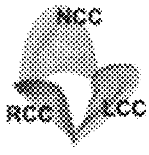

3D Finite Element results

Parasternal short-axis view

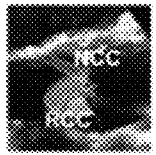

Parasternal long-axis view

DE FE

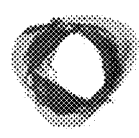

3D Finite Element results

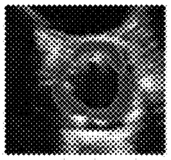

Parasternal short-axis view

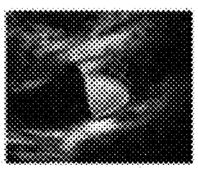

Parasternal long-axis view

DE FE (b) Time-averaged maximum principal stress during full cardiac cycle (MPa)

Pre intervention (native valve leaflets)

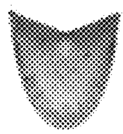

Left-coronary cusp

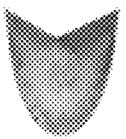

Non-coronary cusp

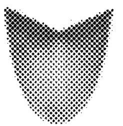

Right-coronary cusp

Post intervention (transcatheter leaflets)

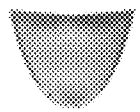

Left-coronary cusp

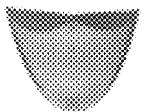

Non-coronary cusp

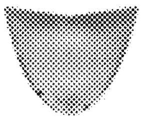

Right-coronary cusp

-2.0e-01 -0.15 -0.1 -0.05 0 0.05 0.1 0.15 0.2 0.25 0.3 0.35 4.0e-01

(c) Leaflet stiffness and valve performance

Pre intervention (native valve leaflets)

Calibrated material properties (C10)
1.4 MPa
1.48 MPa
0.51 MPa

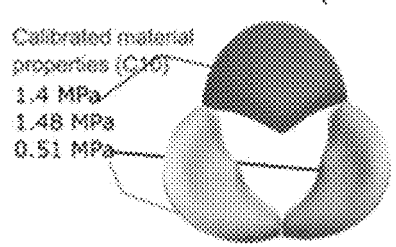

0.38 Ejection time (seconds)

0.82 Total cardiac cycle duration (seconds)

Post intervention (transcatheter leaflets)

Calibrated material properties (C10)
0.25 MPa
0.25 MPa
0.26 MPa

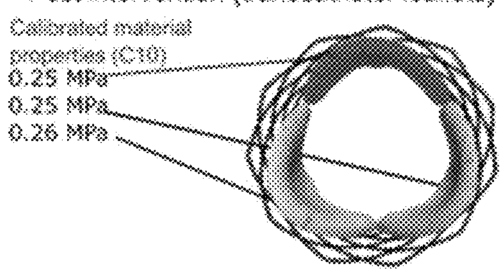

0.27 Ejection time (seconds)

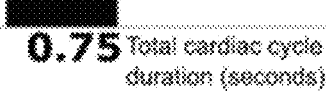

0.75 Total cardiac cycle duration (seconds)

FIG. 25

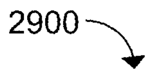

Receive Doppler echocardiography images of the subject — 2905

Process received images to reconstruct a 3D geometry of the valve leaflets — 2910

Determine transient pressure boundary conditions using subject-specific lumped parameter model — 2915

Perform first finite element simulation to determine one or more geometrical parameters based on the reconstructed 3D geometry, determined transient boundary conditions and initial value of material parameters of the valve leaflets — 2920

Iteratively calibrate the initial value of the material parameters for the subject by comparing determined geometrical parameters with a measured geometrical parameter — 2925

Perform second finite element simulation based on calibrated material parameters to determine indicators — 2930

FIG. 29

DOPPLER-BASED NON-INVASIVE COMPUTATIONAL DIAGNOSTIC METHOD FOR PERSONALIZED CARDIOLOGY

RELATED APPLICATIONS

This application claims the benefit of priority to U.S. Provisional Application No. 63/262,902 filed Oct. 22, 2021 and U.S. Provisional Application No. 63/262,908 filed Oct. 22, 2021, the entire contents of both of which are hereby incorporated by reference.

FIELD

The described embodiments relate to non-invasive computational diagnostic methods for personalized cardiology, and more specifically relate to non-invasive computational diagnostic methods for personalized cardiology using doppler-based computational mechanics.

BACKGROUND

Aortic stenosis (AS) is an acute and chronic cardiovascular disease that is described as the narrowing of the aortic valve opening which restricts blood flow from the left ventricle (LV) to the aorta. Most importantly, in many patients, AS coexists with other complex valvular, ventricular, and vascular diseases. In this situation, several complex (and mixed) diseases of the valves, ventricles and the vascular system mechanically interact with one another, and their combination may exacerbate adverse effect on AS and each isolated disease on the cardiovascular system. Patients with AS are often asymptomatic for a long period of time but can suddenly become symptomatic [1, 2]. Once symptoms emerge, there is a 25% increase in mortality rate per year [3]. Over time, AS is likely to lead to LV dysfunction and hypertrophy which often results in cardiac failure and early mortality [3]. If aortic valve disease is left untreated in these patients, 50% will die within two years of developing symptoms. Furthermore, sudden death has occurred in 3-5% of patients with AS and thus, diagnosis and treatment must be administered promptly and precisely [4, 5].

Transcatheter aortic valve replacement (TAVR) is an emerging treatment alternative to surgical aortic valve replacement that covers a range of patients suffering from moderate to severe aortic stenosis (AS) [6]. Surgical valve replacement remains the standard treatment method for AS, however, many patients suffering from this pathology are at a high risk for surgery and may suffer death or other complications [7-9]. Up to 30% of patients with severe AS do not undergo surgical treatment due to the risks [10, 11], however, if left untreated AS carries dismal prognosis [12]. TAVR is a growing alternative for intervention of AS patients across a broad risk spectrum and has lower death rates in severe cases compared to a surgical approach [8, 9]. Although TAVR has critical benefits for surgical high-risk patients, there are several drawbacks that patients may experience. Above 20% of patients suffer from paravalvular leaks post-intervention [6, 13-15], mitral regurgitation has been shown to occur in approximately 33%, and other negative outcomes such as heart failure have occurred [6, 16]. Given the associated risks with TAVR, it is crucial to determine: how the implant will affect the cardiac function? When is the proper timing for intervention? Will TAVR improve or worsen the outcome of the patient [17].

The condition of the heart valves heavily relies on the geometry and material properties of the leaflets as well as the interaction between the flow and the valve [18, 19]. Valvular disease, including AS, often results in, or is a result of abnormal stress and strain distributions on aortic valve leaflets for both pre- and post-interventional cases [20, 21]. The main cause of AS is calcification build-up [22], however, additional potential causes include birth defects, rheumatic fever, or radiation therapy [23]. Mechanical strain and stress on the aortic valve are heavily influential on the progression of calcification [17,24-27]. The accurate estimate of the valve dynamics is crucial in the proper diagnosis of heart valve diseases [17,28-30]. Furthermore, the main causes of degeneration and, consequently, failure of prosthetic heart valves (e.g., transcatheter aortic valve) are mechanical stresses [31]. Effective treatment strategies, indeed, rely heavily on the complete understanding of the valve dynamics [32]. Such biomechanical features are greatly impactful when diagnosing and evaluating aortic valve pathologies [33]. However, there are no tools currently available to invasively or noninvasively quantify stress or strain distribution of aortic valve leaflets [29, 34].

Assessments of the valve dynamics in both pre and post-TAVR can have incredible impacts on patient care. If available, assessment of valve dynamics provide valuable information about the patient's state of cardiac deterioration as well as heart recovery, planning interventions and making critical clinical decisions with life-threatening risks [27, 35]. Despite remarkable advancements in medical imaging, imaging on its own cannot provide valve dynamics features which are very important for the long-term health of the heart and durability of the valve leaflets [29, 36]. There are no current clinical tools available to invasively or noninvasively quantify valve dynamics [29, 34, 36].

Numerical frameworks devised for 3-D quantification of valve dynamics in patients are expected to have the following 6 requirements:

Requirement #1. The physical model should sufficiently represent the realistic dynamic behavior of aortic valve leaflets. Anisotropic tissues of aortic valve leaflets experience extremely large deformations in interaction with transvalvular blood flow in each cardiac cycle and any numerical solver should accurately address these complexities. Neglecting the anisotropic behavior of leaflet tissues could cause non-physical stress distribution and displacement during valve closure [37, 38].

Requirement #2. There has been a conclusion by many researchers that valvular disease is a complex disease that also depends on the dictates of the ventricle and the vascular system [6, 39-44]. Local flow dynamics are greatly influenced by both downstream and upstream conditions, and therefore, it is critical to impose correct boundary conditions to the model that takes the interactive coupling of the valve, ventricle, and the vascular system into account [6, 45-48].

Requirement #3. Material properties of each patient should be calibrated to mimic each patient's tissue behavior. Several experimental tests were performed on normal aortic valve tissues; however, for calcified aortic valve leaflets, there should be a calibration step for material properties of each individual patient [49-51]. Furthermore, because calcification patterns on aortic leaflets differ, each leaflet's dynamic behavior should be evaluated on a leaflet-by-leaflet basis [52-55]. This is especially crucial for patients with valvular disease who undergo transcatheter aortic valve replacement [56-58].

Requirement #4. The 3-D geometry of aortic valve leaflets should be patient-specific and reconstructed in both pre- and post-interventional states. Using simplified geometry, such as symmetric leaflets, would make the framework blind to geometrical differences of leaflets [59]. Leaflet sizes differ, and consequently experience different stress distribution and biomechanical behavior [60]. In addition, patients have different other geometrical parameters, such as the height of aortic valve cusps varying from patient to patient, which can have a considerable impact on the stress distribution [59, 60]. As there is a link between leaflets' stress distributions and disease progressions [27, 55], it is critical to consider the patient-specific leaflet geometry when assessing the stress and biomechanical features.

Requirement #5. A computational framework should ideally be transferrable to clinical practice. As such, it is imperative that the computational cost of the framework, non-invasiveness, and number of unknown parameters in each step of the framework are rigorously evaluated [47, 61-63]. Based on predetermined clinical goals, a trade-off should be considered between accuracy, time, and invasiveness [64, 65].

Requirement #6. Any computational framework devised for clinical diagnosis should be validated against clinical data, e.g., clinical cardiac catheterization, DE, MRI and/or CT [61, 66-69, 69, 70].

Many past studies have used nonlinear finite element methods to quantify stress and strain distributions on aortic valve leaflets. None of these previous models can satisfy all six of the above requirements [7, 18, 29, 71-92]. Several past studies have been unable to satisfy Requirement 1 as quasi-static assumptions were used for motion equations, which assume a static situation rather than dynamic [80, 88, 90] or isotropic hyper-elastic models were used which do not account for the anisotropic structure of the aortic valve leaflets [18, 32, 73, 75, 76, 78, 79, 82, 85, 87, 89]. Requirement 2 has never been met as all previous models have used constant or non-patient specific pressure loads which ultimately leads to the failure of Requirement 3 as material properties cannot be calibrated properly for each patient [7, 18, 32, 71, 72, 74-78, 81, 83-85, 87-90, 93]. Several other studies have used simplified 3-D geometries for aortic valve leaflets that are symmetric which contradicts Requirement 4 [32, 72, 83-86, 89, 91-93]. Requirements 5 and 6 have never been mentioned in any of the proposed models [7, 18, 32, 71-93].

Methods for monitoring, treatment planning and risk assessment in patients with AS are heavily reliant on the data gathered from the various forms of medical imaging such as Doppler echocardiography (DE), computed tomography (CT), and magnetic resonance imaging (MRI). CT carries risk and MRI can not be used in patients with implanted devices, remaining a major risk during the examination. Moreover, CT and MRI can be used to reconstruct the 3-D geometry of aortic valve leaflets [94], however, the segmentation procedure is time-consuming and challenging since aortic valve leaflets are thin structures that move swiftly in each cardiac cycle [95-97]. DE is commonly used in patients with cardiovascular diseases and is risk-free.

SUMMARY

The described embodiments use computational mechanics as a powerful means to enhance clinical measurements, and medical imaging to develop a novel Doppler-based non-invasive diagnostic method for personalized cardiology of subjects. In one or more embodiments, the subjects may be patients with valvular diseases in both pre-intervention and post-intervention status. The described embodiments can be eventually used for monitoring, treatment planning and risk assessment in patients with valvular disease (e.g., AS) in both pre-intervention and post-intervention states upon future further validations. In one or more embodiments, the intervention can be TAVR and the described embodiments may be used for monitoring, treatment planning and risk assessment in patients with AS in both pre-TAVR and post-TAVR states. DE is a risk-free, non-invasive imaging technique commonly used in patients with cardiovascular diseases. The described embodiments include a highly innovative non-invasive Doppler-exclusive computational-mechanics framework that can function as a diagnostic tool to assess aortic valve dynamics in pre-intervention and post-intervention states at no risk to the patients.

The developed diagnostic tool can dynamically couple the local valve dynamics with the global circulatory system that provides a platform for testing intervention scenarios (e.g., TAVR) and evaluating their effects. In order to achieve this, a framework was developed based on an innovative Doppler-based patient-specific lumped parameter algorithm and 3-D non-linear finite element solver interaction that satisfies all of the six above-mentioned requirements for developing a clinically-effective computational diagnostic framework to quantify valve dynamics (e.g. transient 3-D distribution of stress and displacement, 3-D deformed shape of leaflets, geometric orifice area and angular positions of leaflets) in patients in both pre-intervention and post-intervention states. The developed lumped parameter algorithm allows for the analysis of any combination of complex valvular, vascular and ventricular diseases in patients, purposefully uses limited and reliable non-invasive input parameters using Doppler echocardiography and sphygmomanometer to continuously calculate patient-specific local and global hemodynamics quantities [43]. To construct the 3-D geometry of the asymmetric aortic valve leaflets, a Doppler-based parametric method was developed. A multi-thread algorithm can be used for solving linear equations of the finite element solver in a timely manner due to the importance of computational time in clinical applications.

Clinical data of 12 patients with AS in both pre-TAVR and post-TAVR states (24 cases) was used to validate the proposed framework and also to demonstrate its monitoring capacities by providing novel analyses and interpretations of clinical data. The validation was done against clinical Doppler echocardiography data and measurements.

In one aspect, there is provided a Doppler-based non-invasive method for determining dynamic behavior of an aortic valve of a subject, the aortic valve having multiple asymmetric valve leaflets. The method includes receiving Doppler echocardiography images of the subject; processing the received images to reconstruct a 3D geometry of the valve leaflets; determining transient pressure boundary conditions for the valve leaflets using a lumped parameter model specific to the subject; performing a first finite element simulation to determine one or more geometrical parameters for the valve leaflets, wherein the first finite element simulation is based on the reconstructed 3D geometry of the valve leaflets, the determined transient boundary conditions and an initial value of one or more material parameters of the valve leaflets; iteratively calibrating the initial value of the one or more material parameters for the subject by comparing the determined one or more geometrical parameters with a measured geometrical parameter; and performing a second finite element simulation, based on the calibrated one or more material parameters, to determine an indicator of the dynamic behavior of the aortic valve.

In one or more embodiments, the 3D geometry of the valve leaflets is reconstructed by processing parasternal long-axis view and parasternal short-axis view Doppler echocardiography images.

In one or more embodiments, the 3D geometry of the valve leaflets is reconstructed by measuring a base diameter, a diameter of commissures, a valve height and a length of central coaptation from the parasternal long-axis view Doppler echocardiographic image.

In one or more embodiments, the 3D geometry of the valve leaflets is reconstructed by measuring multiple leaflet angles from the parasternal short-axis view Doppler echocardiography image.

In one or more embodiments, the lumped parameter model includes one or more of a left ventricle sub-model, a left atrium sub-model, an aortic valve sub-model, a mitral valve sub-model, a pulmonary circulation sub-model, and a systemic circulation sub-model.

In one or more embodiments, the transient pressure boundary conditions include a transient pressure difference between a left ventricle of the subject and an aorta of the subject.

In one or more embodiments, the measured geometrical parameter for the iterative calibration includes an angular position or a geometric orifice area of the valve leaflets.

In one or more embodiments, the measured geometrical parameter is measured from a parasternal long-axis view and a parasternal short-axis view Doppler echocardiographic image at the peak systole time frame in which the aortic valve is in its fully open configuration.

In one or more embodiments, the indicator indicates one or more of a transient 3D distribution of stress and displacement field for the valve leaflets at different time points of a cardiac cycle, a 3D deformed shape of the valve leaflets and a stiffness of the valve leaflets.

In one or more embodiments, the valve leaflets include native valve leaflets or prosthetic valve leaflets.

In one or more embodiments, the method further includes diagnosing, monitoring or prognosing aortic valve stenosis (AS) in the subject based on the indicator.

In one or more embodiments, the indicator indicates dynamic behavior of each of the valve leaflets.

In one or more embodiments, the diagnosing, monitoring or prognosing aortic valve stenosis (AS) is conducted pre-intervention or post-intervention.

In one or more embodiments, the intervention is a transcatheter aortic valve replacement (TAVR).

In another aspect, there is provided a system for determining dynamic behavior of an aortic valve of a subject, the aortic valve having multiple asymmetric valve leaflets. The system includes a processor; and a memory storing processor-executable instructions, wherein the instruction configure the processor to perform any of the methods described herein.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

One or more embodiments will now be described in detail with reference to the drawings, in which:

FIGS. 4A and 4B (collectively referred to herein as FIG. 4) show example validation results of Doppler-based lumped parameter algorithm and Doppler-based 3-D non-linear finite element solver vs. clinical Transesophageal echocardiography data.

FIG. 6 shows Doppler-based patient-specific material properties for the example patient of FIG. 5.

FIG. 8 shows Doppler-based patient-specific material properties in the example patient of FIG. 7.

FIG. 10 shows Doppler-based patient-specific material properties in the example patient of FIG. 9.

FIGS. 13A and 13B (collectively referred to herein as FIG. 13) show example validation results of Doppler-based lumped parameter algorithm and Doppler-based 3-D non-linear finite element solver vs. clinical Transesophageal echocardiography data in pre-intervention and post-intervention status.

FIG. 14 shows 3D motion and 3D distribution contours of Mises stress in an example patient at six time points throughout the cardiac cycle in both pre- and post-intervention states, in accordance with one or more embodiments.

FIG. 16 shows comparison of doppler-based finite element results with computed tomography; leaflet-specific time-averaged major principal stress; and Doppler-based calibrated material properties for the example patient of FIGS. 14 and 15.

FIG. 17 shows 3D motion and 3D distribution contours of Mises stress in another example patient at six time points throughout the cardiac cycle in both pre- and post-intervention states, in accordance with one or more embodiments.

FIG. 18 shows changes in valve dynamics and global hemodynamics between baseline and 90-day post-TAVR for the example patient of FIG. 17.

FIG. 19 shows comparison of doppler-based finite element results with computed tomography; leaflet-specific time-averaged major principal stress; and Doppler-based calibrated material properties for the example patient of FIGS. 17 and 18.

FIG. 22 shows comparison of doppler-based finite element results with computed tomography; leaflet-specific time-averaged major principal stress; and Doppler-based calibrated material properties for the example patient of FIGS. 20 and 21.

FIG. 23 shows 3D motion and 3D distribution contours of Mises stress in another example patient at six time points throughout the cardiac cycle in both pre- and post-intervention states, in accordance with one or more embodiments.

FIG. 24 shows changes in valve dynamics and global hemodynamics between baseline and 90-day post-TAVR for the example patient of FIG. 23.

FIG. 25 shows comparison of doppler-based finite element results with computed tomography; leaflet-specific time-averaged major principal stress; and Doppler-based calibrated material properties for the example patient of FIGS. 23 and 24.

FIG. 29 shows a non-invasive method for determining dynamic behavior of an aortic valve of a subject, in accordance with one or more embodiments.

DESCRIPTION OF EXEMPLARY EMBODIMENTS

Definitions

Figures 1A, 1B:
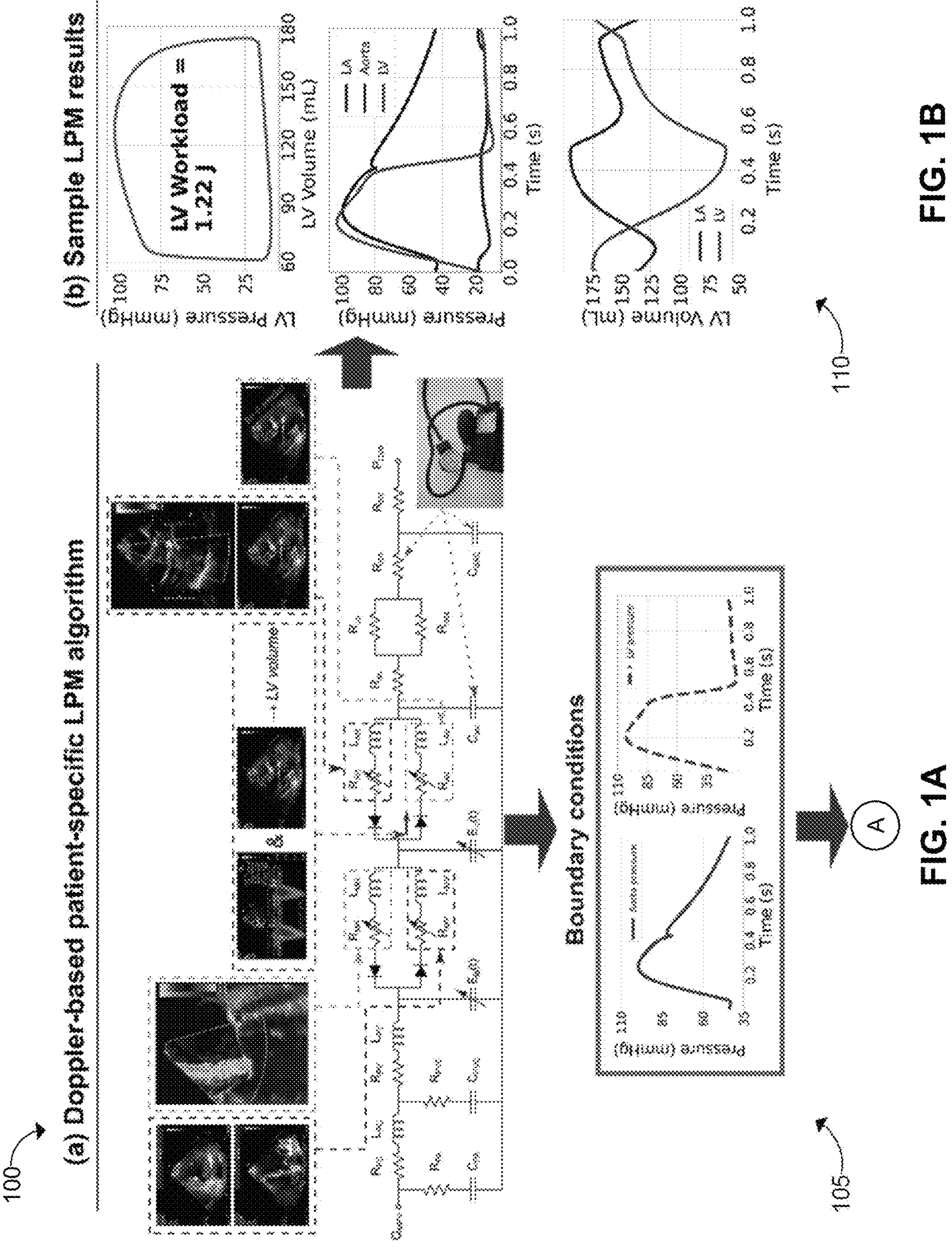
FIGS. 1A-1D (collectively referred to herein as FIG. 1) show a schematic diagram of a Doppler-based diagnostic framework (Doppler-based lumped parameter algorithm and Doppler-based 3-D non-linear finite element solver), in accordance with one or more embodiments.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is used or present.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers or computing devices may be a server, network appliance, embedded device, computer expansion module, a personal computer, laptop, personal data assistant, cellular telephone, smart-phone device, tablet computer, a wireless device or any other computing device capable of being configured to carry out the methods described herein.

In one embodiment, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloads, magnetic and electronic storage media, digital and analog signals, and the like. The computer useable instructions may also be in various forms, including compiled and non-compiled code.

Figures 1C, 1D:
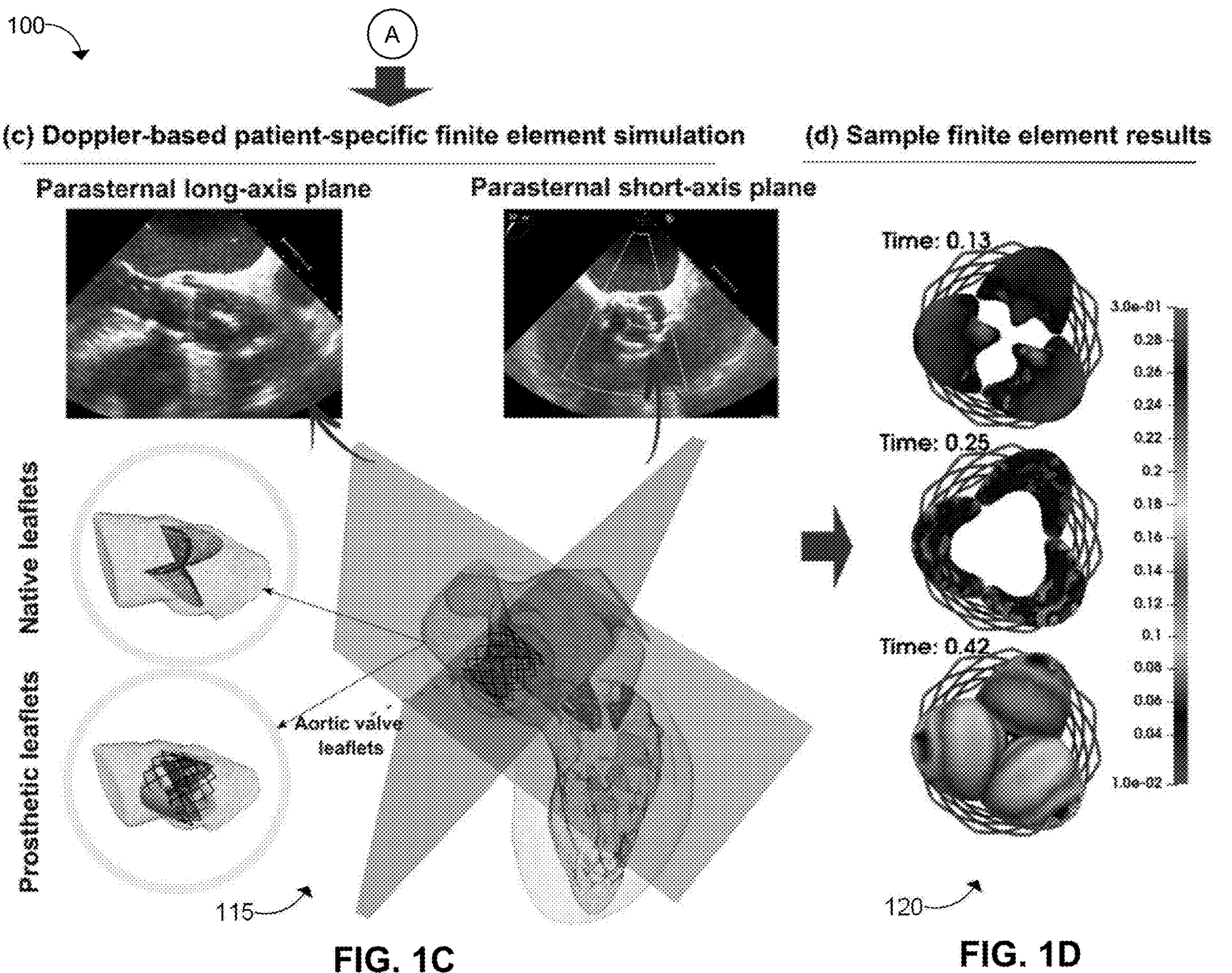
Figure 2:
FIG. 2 shows Doppler-based patient-specific 3-D geometry reconstruction of the aortic valve, in accordance with one or more embodiments.

Referring first to FIGS. 1 and 2, there is provided a Doppler-based computational mechanics diagnostic framework to non-invasively investigate the dynamic behavior of the aortic valve (e.g., transient 3-D distribution of stress and displacement field, 3-D deformed shape of leaflets, geometric orifice area, angular positions of leaflets, stiffness, etc.). This framework may be based on a Doppler-based patient-specific lumped parameter algorithm (LPM) [43], and a 3-D Doppler-based nonlinear (using anisotropic hyper elastic) finite element solver CalculiX [98]. The LPM algorithm is described in U.S. Patent Publication No. 20210338192A1 (U.S. patent application Ser. No. 17/232,606, publication date Nov. 4, 2021), the entire contents of which are hereby incorporated by reference. The LPM algorithm may include a parameter estimation algorithm and a lumped-parameter model [43] that includes several sub-models allowing analysis of any combination of complex valvular, vascular and ventricular diseases (e.g., FIG. 1). In one embodiment, there is provided a Doppler-based parametric method to construct the 3-D geometry of the asymmetric aortic valve leaflets. Calculations of this Doppler-based computational mechanics diagnostic framework were validated against clinical Doppler echocardiography data (FIG. 4) in 12 patients with AS (see e.g., Table 1 included herein below). The transthoracic echocardiogram (TTE) data and transesophageal echocardiography (TEE) data were only used for validation of the framework.

FIG. 1 shows a schematic diagram 100 of a Doppler-based diagnostic framework (Doppler-based lumped parameter algorithm and Doppler-based 3-D non-linear finite element solver), in accordance with one or more embodiments. FIG. 1(*a*) shows a schematic diagram 105 of the lumped parameter algorithm which includes the following sub-models: (i) left ventricle; (ii) left atrium; (iii) aortic valve; (iv) mitral valve; (v) pulmonary circulation; and (vi) systemic circulation [43]. The lumped parameter algorithm can provide patient-specific transient loads on the aortic valve, including the aorta and left ventricle pressure during cardiac cycle. These transient loads can be imposed on both the ventricular and aortic surface of aortic valve leaflets. FIG. 1(*b*) shows sample curves 110 representing global hemodynamic parameters including pressure-volume loop, volume, and pressure variation of different regions of the heart during full-cardiac cycle including the left ventricle, aorta, and left atrium. The workload may be the integral of LV pressure and its volume change and may be computed as the area encompassed by the LV pressure and volume loop. FIG. 1(*c*) shows doppler heart views 115 that may be used for the valve reconstruction to be used in finite element simulations. The aortic valve leaflets may include native leaflets or prosthetic leaflets. FIG. 1(*d*) shows sample finite element results 120, including 3D distribution of stress and displacement over heart valve leaflets at different time points of the cardiac cycle.

TABLE 1

Baseline patient characteristics including patient description, arterial hemodynamics, aortic valve hemodynamics and left ventricle hemodynamics of patients selected for the example study.

| | AS Patients (n = 12, mean ± SD) |
|---|---|
| Patient description | |
| Mean age (years) | 76 ± 3.5 |
| Gender | (Male: 9; Female: 3) |
| Mean weight (kg) | 69 ± 12.5 |
| Mean height (cm) | 169.9 ± 10.6 |
| Body surface area ($m^2$) | 1.7 ± 0.11 |
| Body mass index ($kg/m^2$) | 32.1 ± 24.8 |
| Arterial hemodynamics | |
| Systolic arterial pressure (mmHg) | Pre-TAVR: 131.16 ± 26.13; Post-TAVR: 124.9 ± 16.25 |
| Diastolic arterial pressure (mmHg) | Pre-TAVR: 61.16 ± 10.46; Post-TAVR: 61.0 ± 12.09 |
| Aortic valve hemodynamics | |
| Stenotic aortic valve effective orifice area ($cm^2$) | 0.725 ± 0.135 |
| Stenotic aortic valve type | Tricuspid: 12; Bicuspid: 0 |
| Prosthetic size (mm) | 25 ± 2.83 |
| Prosthetic type | Edwards SAPIEN (n = 12) |
| Maximum aortic valve pressure gradient (mmHg) | Pre-TAVR: 52.22 ± 20.37; Post-TAVR: 17.26 ± 13.8 |
| Mean aortic valve pressure gradient (mmHg) | Pre-TAVR: 29 ± 18.6; Post-TAVR: 12.5 ± 4.7 |
| Left ventricle hemodynamics | |
| Ejection fraction (%) | Pre-TAVR: 36.26 ± 14.4; Post-TAVR: 38.75 ± 13.4 |
| Heart rate (bpm) | Pre-TAVR: 70 ± 25.7; Post-TAVR: 70.52 ± 10.56 |

Study Population

Twelve patients with severe AS were selected who underwent TAVR at St. Paul's Hospital (Vancouver, Canada). Demographic and procedural data were collected from the patient medical records (see Table 1 for details). The data were transferred as the de-identified & anonymized data from St. Paul's Hospital and the approval was granted by the Clinical Research Ethics Board (CREB). All methods and measurements were performed in accordance with the relevant guidelines and regulations including guidelines of the American College of Cardiology and American Heart Association. Results were expressed as mean±standard deviations (SD).

Data Acquisition—Doppler Echocardiography

Doppler echocardiography (DE) data included raw images and documented reports, and were collected at the baseline, and at 90-day post procedure. Echocardiograms and reports were reviewed and analyzed by senior cardiologists using OsiriX imaging software (OsiriX version 8.0.2; Pixmeo, Switzerland).

Input Parameters of the LPM Algorithm

In one embodiment, the algorithm may use the following input parameters that can be reliably measured using DE: forward left ventricular outflow tract stroke volume, heart rate, ejection time, ascending aorta area, left ventricular outflow tract area, aortic valve effective orifice area, mitral valve effective orifice area, and grading of aortic and mitral valves regurgitation severity. These parameters may be measured in the parasternal long-axis, parasternal short-axis, apical two-chamber, apical four-chamber, and apical five-chamber views of the heart [43] (see e.g., FIG. 1 and Table 1 for details).

Patient-Specific Doppler-Based 3-D Geometry of Aortic Valve Leaflets

FIG. 2 shows Doppler-based patient-specific 3-D geometry reconstruction of the aortic valve, in accordance with one or more embodiments. FIG. 2(*a*) shows parasternal long-axis doppler echocardiographic image with labelled dimensions including base diameter (D_b), diameter of commissures (D_c), valve height (H), length of central coaptation (X_s) to be used for valve reconstruction. FIG. 2(*b*) shows parasternal short-axis doppler echocardiographic image with labelled dimensions (two angles of the leaflets; $\alpha$ and $\beta$). FIG. 2(*c*) shows patient-specific 3-D geometry construction of aortic valve leaflets. All input parameters may be measured using parasternal long-axis view and parasternal short-axis view.

Parametric models of aortic valve leaflets can be used to directly represent the function of the aortic valve [87, 99]. The developed method [100, 101] was further modified [73, 102] to remove the symmetric simplifying assumption (see e.g., FIGS. 2B and 2C). This parametric method may be implemented using Autodesk Inventor 2017 [103] to construct the 3-D geometry of the aortic valve leaflets of patients in both pre and post intervention status using 2-D DE images (see e.g., parasternal long-axis and short-axis views, FIG. 2). For this purpose, the essential parameters may be measured using DE images and can be as follows: base diameter (D_b), diameter of commissures (D_c), valve height (H), length of central coaptation (X_s) and two angles of the leaflets ($\alpha$ and $\beta$); all measured at the end of diastole:

A conical frustum can be composed using the following dimensions (see e.g., FIG. 2(*a*)): diameter of the base (D_b), diameter of commissures (D_c) and valve height (H). These dimensions can be measured on the long-axis parasternal Doppler echocardiography plane view (see e.g., FIG. 2(*a*)). The conical frustum may be composed of three surfaces: two circular flat surfaces 205 and 210 (shown in hatch in FIG. 2(*c*) (step 1)) and a curved surface 215. The plane M 220 (shown in FIG. 2(*c*) (steps 1, 4 and 5)) may pass though the upper surface 205.

In order to account for the asymmetry of the leaflets, two angles, $\alpha$ and $\beta$ may be measured using the parasternal short-axis plane view (see e.g., FIG. 2(*b*)) to specify points A, B and C on the base surface of the conical frustrum (see e.g., FIG. 2(*c*), steps 2 and 3). Three additional points (A', B' and C') with a rotation of 180° may be marked on the upper circle of the conical frustum (FIG. 2(*c*), steps 2 and 3).

For each leaflet, a plane determined by three points (two on the upper surface and one on the base surface) can be made (see e.g., FIG. 2(*c*), step 3). The three defined planes have curved intersections with the cone-shaped surface (see e.g., FIG. 2(*c*), step 4). Intersection curves 1, 2, and 3 (labelled as curves 225, 230 and 235 respectively) may be made between the intersection of the cone shaped surface and planes 1, 2 and 3, respectively (FIG. 2(*c*), steps 3 and 4). The green curves 225, 230 and 235 represent the attachment of the leaflets to the aortic root (FIG. 2(*c*), step 4).

All green curves 225, 230, and 235 defined in the previous step may be projected to plane M 220 (see e.g., FIG. 2(*c*), step 5), their projection axes were measured to be 5.25° from the Z axis (see e.g., FIG. 2(*c*), supplement 1). The projected curves on plane M may be used to represent the open configuration of the leaflets (see e.g., FIG. 2(*c*), step 5; FIG. 2(*c*), supplement 2). Each leaflet can be defined by an intersection curve (shown in green, e.g., 225, 230 and 235), its projection on plane M (shown in purple, e.g., 240), and the marched surface of the loft technique (see e.g., FIG. 2(*c*), step 5).

The Thubrikar approach may be employed using symmetry planes to approximate the closed configuration of the leaflets. To achieve this, each leaflet in its fully open configuration may be mirrored by its corresponding plane marked in orange lines 245, 250, 255, 260 and 265 (see e.g., FIG. 2(*c*), step 5 and supplement 2). Furthermore, the intersection region that resulted from the closed configuration may be removed from each leaflet (see e.g., the hatched area in FIG. 2(*c*), supplement 2).

Using parameter X_S, the coaptation area can be added to the closed configuration of each leaflet. X_S can show the length of the coaptation region for each leaflet in the Z direction. Additionally, three points, X, Y and Z may be defined with the X_S distance on the top of the free edge 270 (shown in blue color) in the Z direction (see e.g., FIG. 2(*c*), step 6). Two lines 275 and 280 may then be used to connect points X and Y as well as points Y and Z, both displayed in red (see e.g., FIG. 2(*c*), supplement 3). Finally, the blue edges 270 can be extended to the red lines 275 and 280 in the Z direction (see e.g., FIG. 2(*c*), supplement 3).

Patient-Specific Doppler-Based Finite Element Modeling

In one embodiment, the dynamic behavior of the aortic valve leaflets can be modelled using motion equations solved by a non-linear finite element method. There are various challenges associated with solving motion equations of aortic valve leaflets and several past studies have been conducted with many limitations: (1) Quasi static assumptions were often used for motion equations which assume a static situation rather than dynamic [80, 88, 90]; (2) Isotropic hyper-elastic models were used which do not account for the anisotropic structure of the aortic valve leaflets [18, 32, 73, 75, 76, 82, 87, 89, 104-106]; (3) Pressure loads and boundary conditions were often non-patient specific or constant; (4) Material properties were not calibrated for each individual patient [7, 18, 32, 71, 72, 74, 76-78, 81, 83-85, 87-90, 93]; and (5) Symmetric configuration of leaflets was assumed [32, 72, 83-86, 89, 91, 93]. To overcome these limitations, a realistic finite element simulation can be performed by addressing the non-linearities of the aortic valve leaflet motion and a fibre-reinforced constitute law can be used, representing the anisotropic structure of aortic valve leaflets. In addition, the inertia term in motion equations may be considered (see e.g., Equation 3) to represent dynamic loading. For the disclosed model to have a patient-specific simulation, patient-specific transient pressure loads can be calculated using a LPM algorithm [43]. The hyper-elastic material properties of each leaflet can be calibrated using parasternal long and short axis DE plane views for each patient. Further, the asymmetric configuration of aortic valve leaflets can be considered in 3-D geometry construction of leaflets using DE images.

Finite Element Solver

Dynamic equations of motion can be obtained by considering the conservation of linear momentum in conjunction with the conservation of mass, expressed as the following:

$$\rho_s \frac{D^2 U}{D^2 t^2} = \nabla \cdot P + \rho_s f \qquad \text{Equation (1)}$$

where P, f, $\rho_s$, U and $$\frac{D^2(U)}{D^2 t^2}$$

are the Piola transform of the Cauchy stress tensor (viz. Piola-Kirchhoff stress tensor), the body force (e.g., unit weight of the material), the density, the displacement and the second rate operator, respectively. To complement Equation 1, an appropriate constitutive law may be employed, which assumes the materials of the aortic valve to be hyper-elastic based, leading to the following expression:

$$P = C{:}E,\ E = \frac{1}{2}\left(F^T F - \delta\right) \qquad \text{Equation (2)}$$

where C, E and F are the elasticity tensor, the Green-Lagrange strain tensor, and the deformation gradient (the unit tensor), respectively. In order to calibrate the stiffness tensor (C), performing experimental tests may be necessary which can be found described herein in the Material Properties section.

Due to the existing nonlinearities and complex geometries of the aortic valve leaflets, the governing equation of motion (Equation 1) may not be solved analytically. In order to solve Equation 1, it can be converted to its weak (variational) form of representation, employing the Galerkin method and incorporating finite element discretization [98, 107]. By doing so, the semi-discrete form of the governing equations can be obtained as follows:

$$[K]\{U\} + [M]\frac{D^2}{Dt^2}\{U\} = \{F\} \qquad \text{Equation (3)}$$

where [K] is the global stiffness matrix, [M] represents the global mass matrix, and {F} denotes the global force vector. Euler time-discretization of motion equations may be done using the implicit a-method of Miranda et al. [108]. The time steps can be kept sufficiently small (1 E-4 s) to avoid divergence of the nonlinear Newton solver. SPOOLES library may be used for a multi-threaded approach to solve linear equations [109]. CalculiX (version 2.15, an open-source package) may be applied for the dynamic finite element simulation [98].

Boundary Condition

Local flow dynamics may be greatly influenced by both downstream and upstream conditions, and therefore, it may be critical to impose correct boundary conditions to the model. Each leaflet can have two surfaces, one on the ventricular side and one on the ascending aorta side. Initially, the faces connected to the root may have no displacement (see e.g., FIG. 1). The time-dependent pressure boundary conditions (both aorta and LV side) can be calculated using the described patient-specific image-based lumped-parameter algorithm and can be imposed on the surface of the leaflets of both aorta and LV sides (see e.g., FIG. 1). In some embodiments, the pressure difference between the LV and aorta can define the dynamic behavior of the aortic valve and not each of these pressures independently. A dry assumption (without flow) may be used in the described finite element simulation. Van de vosse et al. [110], who performed a fluid-structure simulation to analyze pressure distribution around the aortic valve, showed that dry assumption for the aortic valve can be acceptable. Their results confirmed that the time-dependent pressure imposed on the leaflet surfaces can be nearly uniform across the entire leaflet. To consider the effect of the surrounding fluid, the viscous damping in the described computational framework may be employed using the coefficients suggested by Marom et al. [111]. All aortic valve geometries may be reconstructed using DE images taken at late diastole to obtain the best possible unpressurized geometry. All simulations may be performed during the entire cardiac cycle.

Material Properties

Experimental studies have shown that the aortic-valve leaflets can be six to eight times stiffer in the circumferential direction than they are in the radial direction since collagen fibers are dominantly aligned in the circumferential direction [100]. Despite the fact that several experimental studies demonstrated that the aortic valve leaflets are anisotropic [112-114], some finite element studies focused on the importance of anisotropic behavior of aortic valve leaflets [115]. For instance, Zakerzadeh et al. [38, 51] showed that in small strain movements of aortic valve leaflets (closure time), assuming isotropy has considerable effects on the finite element results and particularly with regards to the stress distribution. In another study, which used rotation-free shell elements, it was shown that using isotropic behavior can impact the deformed leaflet configuration and underestimate displacements during valve closure [51]. Another comparative study, focusing on the effect of anisotropy of leaflets on the finite element results, found shifts in the location of the leaflet peak stress contrary to what is implied with the isotropic assumption [31]. Furthermore, with regards to the effect of blood flow on the dynamic behavior of leaflets, compared with isotropic leaflets, anisotropic leaflets showed less fluttering during systole [116]. In one embodiment, the following strain energy function that is composed of isotropic and anisotropic terms was employed [117]:

$$U = U_{iso} + U_{aniso} = C_{10}(\bar{I}_1 - 3) + \frac{1}{D_1}(J-1)^2 + \sum_{i=0}^{n} \frac{k_{1i}}{2k_{2i}}\left[e^{k_{2i}(I_{4i}-1)^2} - 1\right] \qquad [4]$$

where $U_{iso}$ and $U_{aniso}$ are isotropic and anisotropic strain energy functions, respectively. $\bar{I}_1$ and J are the first strain invariant and volumetric expansion ratio respectively. $C_{10}$ and $D_1$ are material constants for the isotropic neo-Hookean material model for the matrix. Since the material of aortic valve tissues can be considered to be incompressible [118], the second term of the isotropic component $$\left(\frac{1}{D_1}(J-1)^2\right)$$

vanishes. Numerically, employing zero incompressibility may result in a divergence issue. To avoid divergence, a conservative incompressibility value (i.e., a Poisson's ratio of 0.475) may be assumed in the described simulations. Several studies have used this in simplifying assumption of nearly compressible behavior to finite element simulation of cardiac tissues [119-122].

The isotropic matrix can be reinforced by exponential strengthening terms (U_aniso) in the circumferential fiber direction. Parameter n may define the number of fiber family directions. The dominant alignment of fibers may be assumed to be in the circumferential direction (n=1) [123, 124]. For each leaflet, a local cylindrical coordinate system may be implemented in the finite-element solver, which assigns fiber orientations of each tetrahedral element [111]. $k_1$ and $k_2$ can denote two material constants required for describing the anisotropic component and thus, there may be three material constants ($C_{10}$, $k_1$ and $k_2$) to be determined. Due to the exponential behavior of the anisotropic component of Equation 4, an incorrect initial estimation while running the finite-element code may result in divergence. A correction sub-iteration may therefore be implemented to avoid any divergence during numerical iterations of the Newton-Raphson method for each time step.

In one embodiment, the constitutive model of Equation 4 may be used for aortic-valve leaflets. However, more complicated constitutive equations may also be used for aortic valve leaflets. For instance, Equation 4 can be modified to consider fiber dispersions [125]. More sophisticated methods to account for the local alignment of collagen fibers of each aortic valve leaflet were proposed as well [85, 111, 117]. Kim [117] used beam and shell elements to represent collagen fibers and the elastin matrix, respectively. Marom et al. [85, 126] have adopted a similar method for an FSI simulation of a bicuspid aortic valve. They applied the method to porcine aortic valve by obtaining the fiber orientations of leaflets using microscopy. Even though this is the most detailed model to date, its usage for clinical applications can be unpractical with the currently available imaging modalities to non-invasively obtain fiber orientations of aortic valve leaflets in each patient [127]. To decrease the number of unknown parameters of the anisotropic constitutive model of the aortic valve tissues, Equation 4 was used in one embodiment.

Although several studies applied porcine material properties for humans, Martin et al. showed that the human aortic valve tissues are considerably stiffer than porcine aortic valve tissues in radial and circumferential directions [128]. Moreover, any solution to estimate material properties for clinical applications should be practical and based on non-invasive clinical data.

The detailed information on the mechanical properties of calcified regions of aortic valve leaflets, especially for humans, is not available. It was observed that calcified regions are more brittle than normal leaflets [100] and therefore, two different simplifying methods may be used to model calcification:

(1) Increasing the stiffness of the leaflets [129] using geometrical Doppler echocardiography parameters such as effective orifice area (EOA), geometric orifice area (GOA) or angular position. Calcified leaflets are less elastic than healthy ones, therefore their deformation is restricted. As leaflets get stiffer, they become more resistant to deformation, resulting in a lower geometric orifice area, which is the area available during systole [130]. Healthy leaflets, on the other hand, with greater elastic material qualities, give more area for blood flow, resulting in a larger geometric orifice area [131]. It may be worth noting that the dynamic behavior of leaflets, such as time-dependent deformation, is also influenced by the aortic valve's geometry and pressure loads [132].

(2) modifying local thickness or material properties using CT images of local distributions of calcification on aortic valve leaflets. An increase in thickness or stiffness can reproduce calcification effects on specific regions of leaflets [117, 133].

In one embodiment, the first method can be applied to stiffen each calcified leaflet assuming that calcification only affects the isotropic component of the leaflets [72]. Since the tissue is incompressible, only one constant $C_{10}$ (Equation 4) must be determined to model calcification. It may be important to note that material properties of each leaflet can be determined separately, and one set of parameter values may not be assigned to all leaflets. In one embodiment, to determine the material properties, DE images may be used to compare angular positions obtained from the model with those obtained in patients. To perform this, DE plane views may be reconstructed in the computational domain to directly compare geometrical parameters such as angular position or visible area of leaflets with DE images. The DE parasternal short-axis plane view may be used to observe the left coronary leaflet and DE parasternal long-axis plane views may be used to observe non-coronary and right-coronary leaflets (see e.g., FIG. 3).

Grid Study

All 3-D geometries reconstructed using DE images may be discretized into second-order tetrahedral elements [98]. Mesh generation may be completed in Gmsh open-source package [134, 135]. Due to asymmetrical geometry, different geometrical input parameters, and patient-specific transient boundary conditions, the number of mesh elements may not be identical for all cases. In one example simulation, the largest element edge size was always less than 0.62 mm and the number of elements for all 24 cases investigated in an example study (12 patients) ranged between 26,000 and 37,000 tetrahedral elements. All meshes may be generated using quadratic tetrahedral elements (C3D10). The elements may have four points at each tetrahedron vertex and six points in the middle of each of their six edges. Previous literature support that the quadratic (second-order) elements seem to avoid any numerical locking [98, 136, 137]. Similar element choice (one quadratic element though the thickness) for thin cardiac structure like aortic valve leaflet or mitral leaflets have been used in several studies [138-142]. A grid convergence analysis may be performed in which the mesh definition for solid domains was considered acceptable when the major principal stress, mises stress as well as the maximum displacement in each leaflet in successive meshes showed a variation of less than 1%, such that this difference was not significant [141]. Moreover, time step independency had been studied for all models in which the differences in results (e.g., major principal stress, mises stress as well as the maximum displacement) were not significant (less than 0.5%) [141]. The solution marched in time with a time step of 104 s for all 12 cases. Finally, convergence was obtained when the sum of all residuals reached a value lower than $10^{-8}$.

Sensitivity Analyses

Figure 4B:
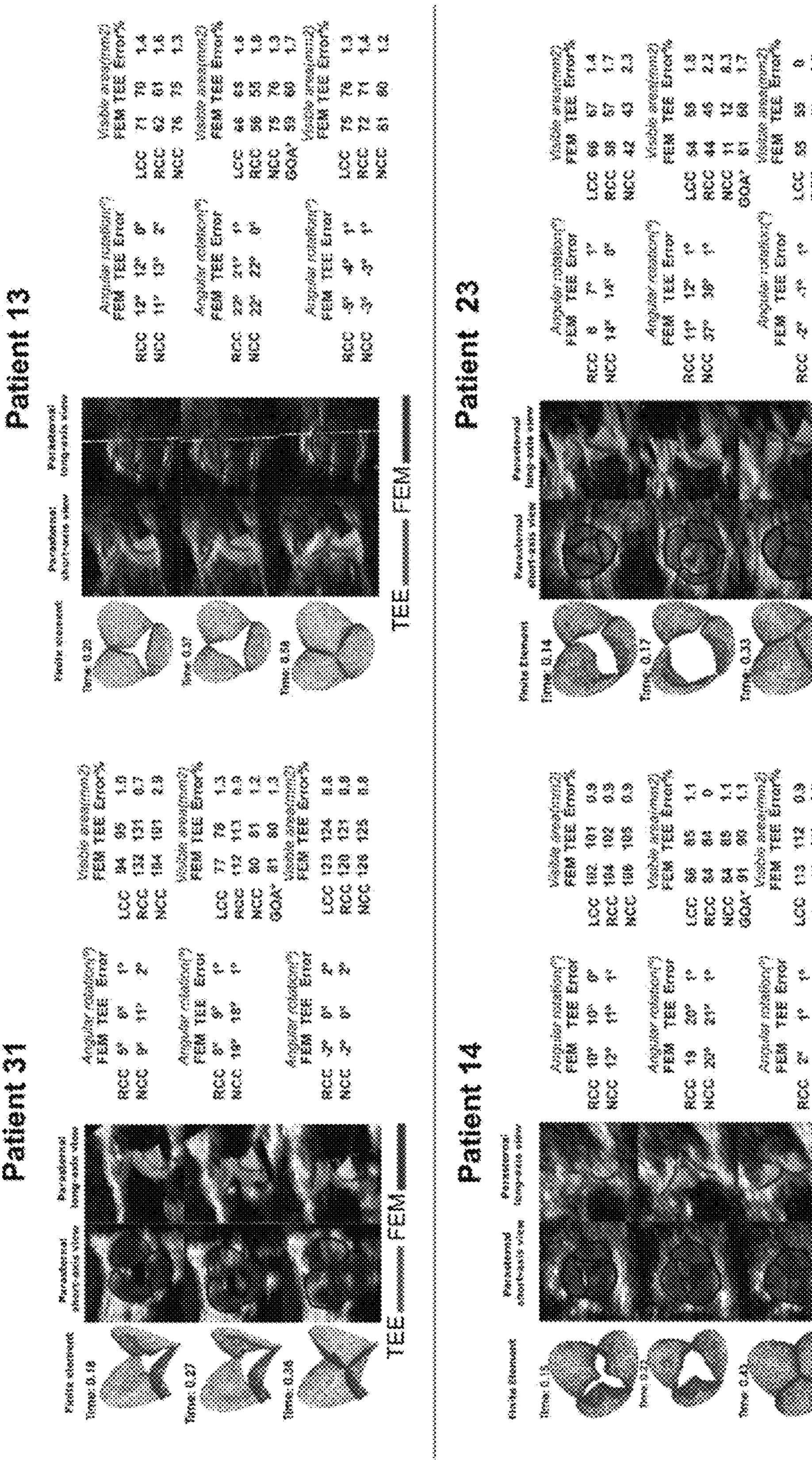

Due to the complex multi-physics nature of the heart valves, the overall estimation of cardiac parameters can be very dependent on the outputs of the lumped-parameter model that can in-turn depend on the parameters used in the lumped-parameter model. The described patient-specific Doppler-based lumped-parameter algorithm, which provided boundary conditions, was validated against clinical catheterization data in forty-nine C3VD patients with a substantial inter- and intra-patient variability with a wide range of disease [43]. In one embodiment, the validated lumped-parameter model [43] was used to obtain time varying left ventricle and aorta pressures as the inputs to the solid model of the aortic valve. Moreover, a comprehensive parameter sensitivity analysis was performed on the outputs of the lumped-parameter model that may be used to find cardiac parameters [143]. In one example, the outputs from the lumped-parameter model were found to be most sensitive to the forward left ventricular outflow tract stroke volume (Forward LVOT-SV, an input parameter to the lumped parameter algorithm): LV pressure: 27%, LV Volume 19% by a ±20% change in the Forward LVOT-SV. The other input parameters affected the output to a much lower degree. It may be pointed out that Forward LVOT-SV can be measured reliably using Doppler echocardiography with high accuracy, and sensitivity of the described model to this parameter may not jeopardize the results obtained from the model. Additionally, in one embodiment, sensitivity analysis revealed negligible effects of changes (±20%) in the free parameters on the model output variables. Indeed, as shown in FIG. 4, the results obtained with Doppler-based 3-D non-linear finite element solver and lumped-parameter algorithm can be validated against clinical Transesophageal echocardiography data in patients. The disclosed results show good agreements between the angular position calculated using the computational framework and the ones measured using clinical Transesophageal echocardiography data in 12 patients investigated in the example study.

The time-dependent pressure boundary conditions (both aorta and LV side) can be calculated using the described patient-specific lumped-parameter algorithm and can be imposed on the surface of the leaflets of both aorta and left ventricle (LV) sides. It may be emphasized that the pressure difference between the LV and aorta can define the dynamic behavior of the aortic valve, not each of these pressures independently. To study the sensitivity of the Doppler-based finite element results (the second step) to the results obtained using the Doppler-based lumped parameter algorithm (the first step), ±10% variations in the aorta pressure (both peak and minimum pressures) and the maximum pressure gradient across the aortic valve during the cardiac cycle (pressure difference between the LV and aorta), can be considered. The calibrated material properties, average Mises stress, and peak Mises stress can be calculated (se e.g., Table 2). It may be observed that the maximum pressure gradient during the cardiac cycle across the aortic valve is the most sensitive parameter and showed up to 7% change in the results due to ±10% variations as described above (see e.g., Table 2). The results may be less sensitive to aorta maximum pressure, and the least sensitive to aorta minimum pressure. It may be noted that the ±10% artificial variations that were defined in the lumped parameters results can be related to changes in the patient condition/pathology if they were to be measured in the real patient. This certainly may have some effects in the finite-element results.

The sensitivity of the calculated angular rotation as well as the leaflets' area to the slight changes (±5% variations) in the estimated material properties can also be investigated. In one embodiment, it was observed that the calculated angular rotation as well as leaflets' area showed up to 4% and 3% changes, respectively.

TABLE 2

The changes in computed calibrated material properties ($C_{10}$), average Mises stress, and peak Mises stress due to ±10% variations in the aorta pressure (both peak and minimum pressures) and the maximum pressure gradient across the aortic valve during the cardiac cycle (pressure difference between the LV and aorta).

| | Left coronary cusp | | | Right coronary cusp | | | Non-coronary cusp | | |
|---|---|---|---|---|---|---|---|---|---|
| | C10 | Mean Mises | Max Mises | C10 | Mean Mises | Max Mises | C10 | Mean Mises | Max Mises |
| | +10% change in maximum aorta pressure | | | | | | | | |
| Patient #31 | −2.80% | −2.40% | −3.40% | −3.65% | −2.60% | −3.20% | −3.65% | −2.53% | −3.40% |
| Patient #29 | −2.40% | −2.80% | −2.90% | −3.10% | −2.10% | −3.70% | −2.90% | −2.45% | −3.00% |
| | +10% change in minimum aorta pressure(mmHg) | | | | | | | | |
| Patient #31 | 0.00% | −0.40% | −0.10% | 0.00% | −0.35% | −0.20% | 0.00% | −0.35% | 0.00% |
| Patient #29 | 0.00% | −1.00% | −0.20% | 0.00% | −0.40% | −0.20% | 0.00% | −0.25% | 0.00% |
| | +10% change in maximum pressure gradient across the aortic valve (pressure difference between the left ventricle and aorta) | | | | | | | | |
| Patient #31 | 5.80% | 5.80% | 7.13% | 6.10% | 5.70% | 5.95% | 5.70% | 6.30% | 5.80% |
| Patient #29 | 5.42% | 4.90% | 6.40% | 7.10% | 6.00% | 6.70% | 4.90% | 6.10% | 6.20% |

| | Left coronary cusp | | | Right coronary cusp | | | Non-coronary cusp | | |
|---|---|---|---|---|---|---|---|---|---|
| | C10 | Mean Mises | Max Mises | C10 | Mean Mises | Max Mises | C10 | Mean Mises | Max Mises |
| | −10% change in maximum aorta pressure | | | | | | | | |
| Patient #31 | 4.10% | 4.10% | 4.90% | 4.20% | 3.95% | 4.90% | 4.00% | 4.00% | 4.90% |
| Patient #29 | 2.84% | 3.40% | 4.45% | 3.66% | 3.41% | 4.10% | 3.40% | 3.45% | 4.11% |

TABLE 2-continued

The changes in computed calibrated material properties ($C_{10}$), average Mises stress, and peak Mises stress due to ±10% variations in the aorta pressure (both peak and minimum pressures) and the maximum pressure gradient across the aortic valve during the cardiac cycle (pressure difference between the LV and aorta).

| | | | | | | | | | |
|---|---|---|---|---|---|---|---|---|---|
| | −10% change in minimum aorta pressure(mmHg) | | | | | | | | |
| Patient #31 | 0.00% | 0.60% | 0.00% | 0.00% | 0.44% | 0.00% | 0.00% | 0.45% | 0.00% |
| Patient #29 | 0.00% | 0.40% | 0.00% | 0.00% | 0.19% | 0.00% | 0.00% | 0.60% | 0.00% |
| | −10% change in maximum pressure gradient across the aortic valve (pressure difference between the left ventricle and aorta) | | | | | | | | |
| Patient #31 | −5.10% | −4.30% | −3.90% | −5.40% | 4.30% | −4.10% | −5.00% | −4.40% | −4.40% |
| Patient #29 | −4.70% | −4.10% | 6.80% | −4.49% | −5.10% | −6.90% | −3.90% | −3.80% | −7.00% |

Numerical Simulation Strategy

Referring next to FIG. 3*a*, shown therein is how different parts of the disclosed framework may function together, including the LPM method, the 3-D image reconstruction module, and the finite element solver. The framework may initially process parasternal long and short-axis DE views to reconstruct the leaflets. Next, the boundary conditions (calculated by patient-specific LPM) and discretized geometry produced by Gmsh may be implemented in CalculiX, as the non-linear finite element solver. The material calibration may be performed using geometrical parameters (angular positions and geometric orifice area) measured at the peak systole time frame in which the aortic valve is in its fully open configuration. For material calibration of non-coronary cusp (NCC) and right-coronary cusps (RCC), peak-systole time frame of parasternal long-axis view from TTE images may be used. The left-coronary cusp (LCC) may not be visible in the parasternal long-axis view. Therefore, parasternal short-axis view may be used.

Figure 3:
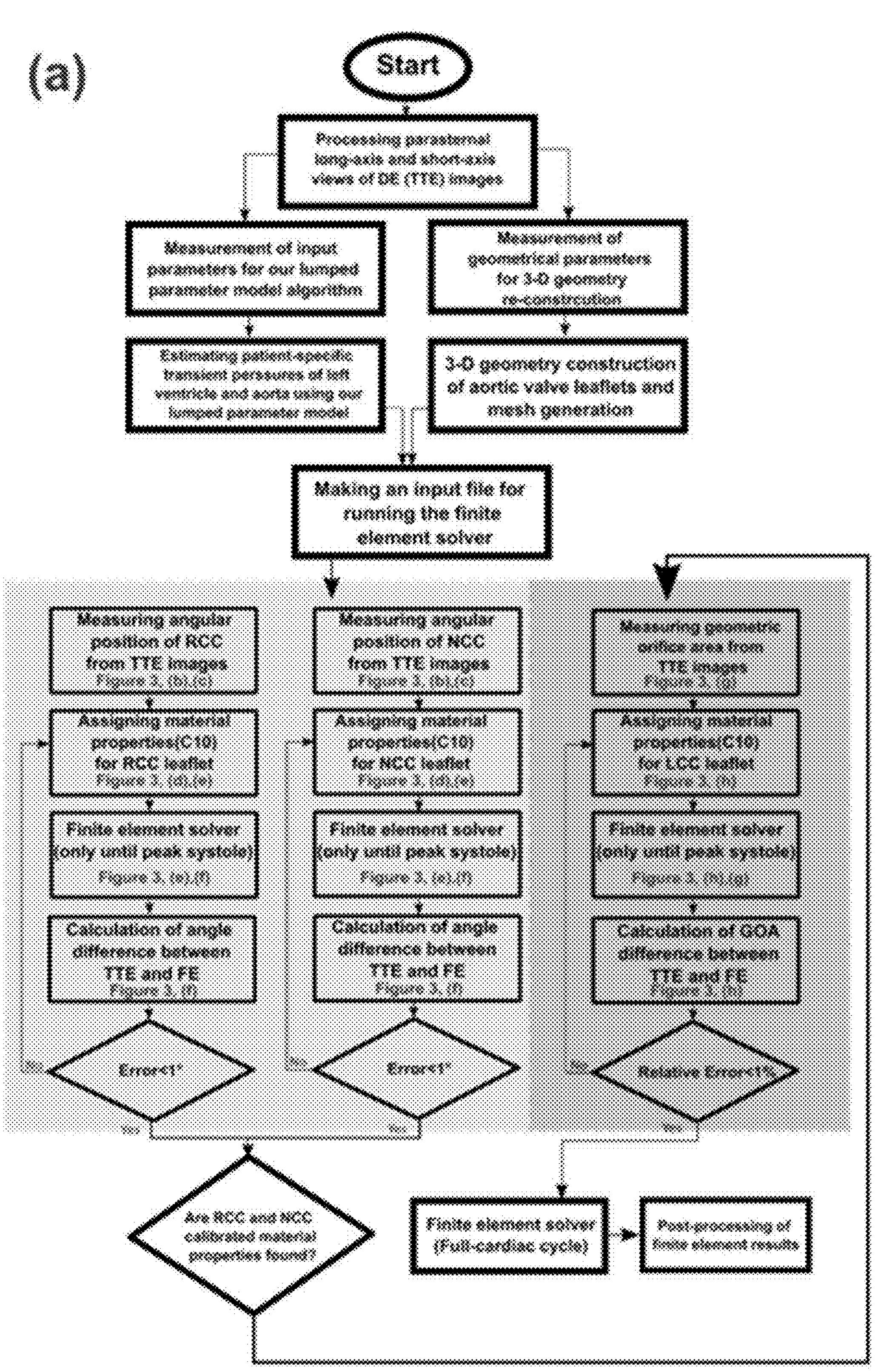
FIG. 3 shows Doppler-based patient-specific lumped parameter algorithm and finite element solver flow chart, in accordance with one or more embodiments.
Figure 3:
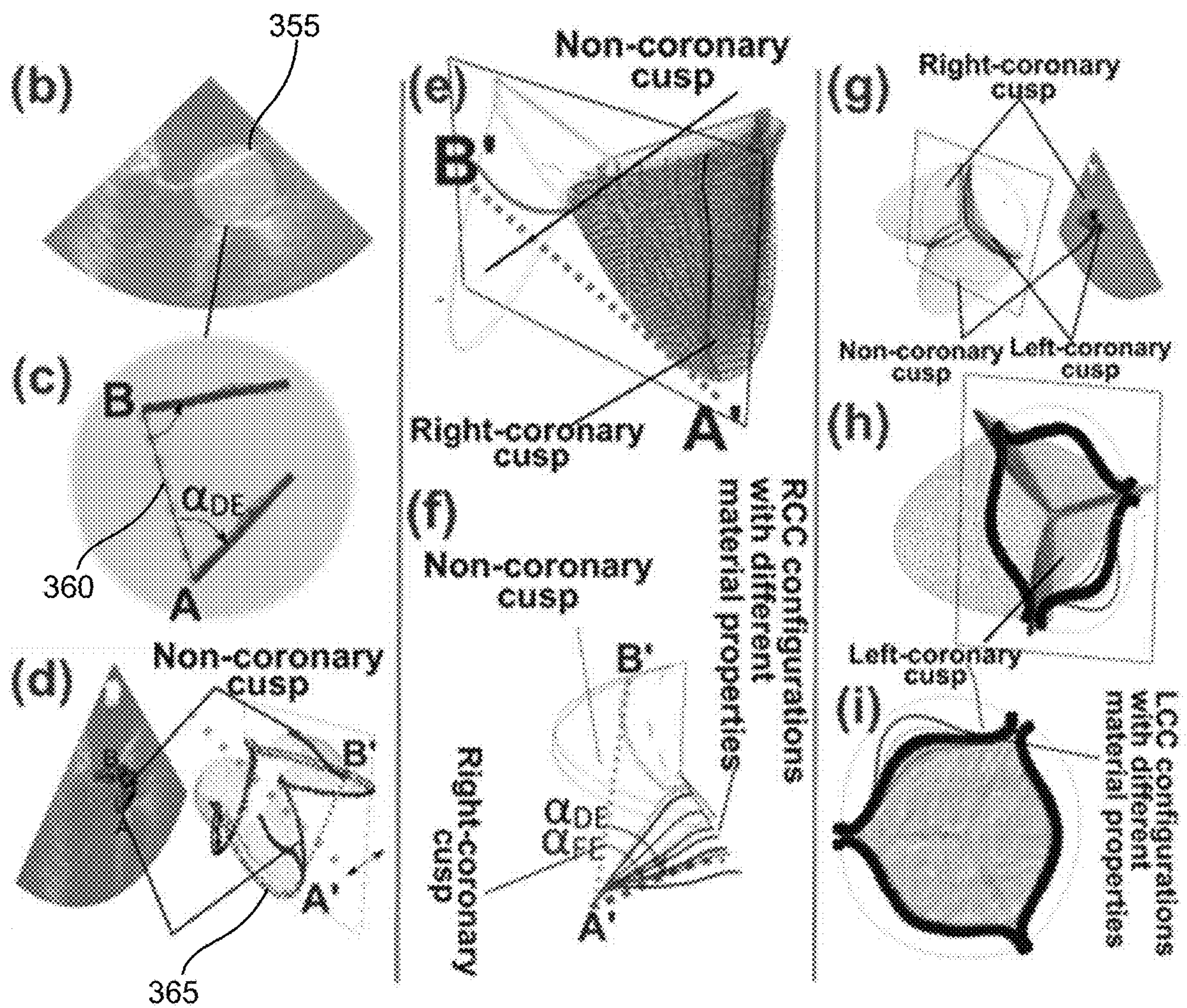

FIG. 3 shows Doppler-based patient-specific lumped parameter algorithm and finite element solver flow chart, in accordance with one or more embodiments. FIG. 3(*a*): As a fully non-invasive framework, all required parameters for LPM algorithm and 3D image construction may be collected non-invasively using Doppler echocardiography images. Having transient pressure loads and 3-D geometry of aortic valve leaflets, a patient-specific finite element simulation may be performed. To have a calibrated material properties for each leaflet, angular position of leaflets and geometric orifice area may be considered. FIGS. 3(*b*) and (*c*): Parasternal long-axis view Doppler echocardiography (TTE) images may be used to manually measure the angular rotation of leaflets using the AB line 360 (drawn between the attachment of the left coronary cusp and non-coronary cups to the aortic root). FIG. 3(*d*): The parasternal long-axis view may be replicated in the computational domain. FIGS. 3(*e*) and (*f*): Angular positions of leaflets (RCC and NCC) in the computational domain may be matched with the measured angular positions in Doppler echocardiography images. FIG. 3(*g*) The geometric orifice area of the aortic valve may be measured in the fully open configuration using parasternal short-axis view. FIGS. 3(*h*) and (*i*): The stiffness of the left coronary cusp may be matched to the geometric orifice area of the aortic valve.

The sub-iteration and details may be as follows:

(1) The right coronary cusp (RCC) and non-coronary cusp (NCC) are highlighted (355) in parasternal long axis echocardiography plane views (TTE) at peak systole (see e.g., FIG. 3(*b*)).

(2) The points denoting the location where leaflets (NCC and RCC) are attached to the root wall are labelled (shown with A and B points in FIG. 3(*c*)). The imaginary line 360 between points A and B may serve as a reference line.

(3) The angle between the leaflets and the line 360 may be measured, where the angles are the angular positions of each leaflet (NCC and RCC) at the fully open configuration (see e.g., FIG. 3(*c*)). This measurement may be performed at the peak systole time point of the parasternal long-axis plane view of Doppler echocardiography (TTE).

(4) Parasternal long-axis plane view intersecting with RCC and NCC may be replicated in the computational domain. The contact points between the long-axis plane and the root attachment edge of the leaflet (shown with blue points 365 in FIG. 3(*d*)) are marked. The intersection of the parasternal long-axis plane view with the root is shown with A' and B' standing for the points A and B discussed in step (2). In the replicated plane drawn in the computational domain (see e.g., FIG. 3(*d*)), the length of line A'B' is matched to the length of the AB line in the TTE images.

(5) In this step, $C_{10}$ parameters of RCC and NCC leaflets may be calibrated by matching the angular position at the peak systole time point of finite element results with angular position of the leaflets at the peak systole time point measured in parasternal long-axis Doppler echocardiography (TTE) in step (3). Based on the initial $C_{10}$ parameter, estimated boundary conditions calculated by the LPM algorithm and the prepared 3D geometry, a finite element simulation may be performed to capture the peak systole time point (fully open configuration) of the RCC (or NCC) leaflet. In each iteration for the guessed $C_{10}$ parameter, the angular positions of the leaflets using A'B' as the reference line may be calculated at the peak systole time frame (see e.g., FIGS. 3(*e*) and 3(*f*)). The error function employed for the material calibration can be defined as the difference between the angular position measured by TTE (step (3)) and the angular position calculated by finite element method. An iterative procedure may be performed for both leaflets (NCC and RCC) with an error of less than one degree.

(6) After the calibration of NCC and RCC leaflets, the geometric orifice area (GOA) may be measured using parasternal short-axis view, only at the peak systole time point. The GOA measured in the parasternal short-axis view (rather than the parasternal long-axis view) may be the geometrical parameter used for LCC material calibration (see e.g., FIG. 3(*g*)).

(7) The parasternal short-axis plane view passing through all three leaflets at the junction point of three leaflets can be replicated in the computational domain. Since the material calibration for RCC and NCC was done in the earlier steps, only the deformation of the LCC leaflet affects the geometric orifice area (see e.g., FIG. 3(*g*)).

(8) In this step, the $C_{10}$ parameter of LCC leaflet may be calibrated by matching the GOA at the peak systole time point of parasternal short axis view in the finite element results with the GOA measured at peak systole time point of parasternal short-axis of Doppler echocardiography (TTE). In each iteration, peak-systole time frame of the finite element results may be captured (see e.g., FIGS. 3(*h*) and 3(*i*)). In this step, the material properties of NCC and RCC may be already known from the earlier steps. Therefore, the only free parameter at this step may be the $C_{10}$ parameter of the LCC leaflet. The error function used for material calibration of the LCC parameter can be defined as the GOA difference calculated in the computational domain and the measured GOA at the peak systole time from the parasternal short-axis view of TTE images. The relative error may be one percent.

(9) Post-calibration, the finite element simulation may be performed on the full cardiac cycle. To reduce computational cost, finite element simulation intended for the calibration of each leaflet's material properties (i.e., steps (5) and (7)) may be performed just to capture the peak systole (i.e., when the aortic valve is fully open).

For calibration, a bisection method was developed using PyCal software, ParaView, and SciPy libraries [144-146]. Specifically, a Python script within ParaView can calculate the geometrical parameters of the finite element results. Multiple iterations update the material's properties (i.e., $C_{10}$) from an initial value of 0.3 [147], by invoking the PyCal library to update the CalculiX input file. Using the SciPy library, the bisection method-based mathematical calculations can be performed.

Patient-Specific Doppler-Based Lumped Parameter Modeling

A non-invasive Doppler-based diagnostic lumped-parameter model has been developed, described in detail elsewhere [43], and includes several sub-models allowing for the analysis of any complex and mixed valvular, ventricular and vascular diseases including: 1) left atrium, 2) left ventricle, 3) aortic valve, 4) mitral valve, 5) systemic circulation, and 6) pulmonary circulation (see e.g., FIG. 1). The algorithm uses the following input parameters that can all be reliably measured using Doppler echocardiography: forward left ventricular outflow tract stroke volume, heart rate, ejection time, ascending aorta area, left ventricular outflow tract area, aortic valve effective orifice area, mitral valve effective orifice area, and grading of aortic and mitral valves regurgitation severity. Other input parameters of the model may be systolic and diastolic blood pressures measured using sphygmomanometers. The calculations of the lumped-parameter model were validated against cardiac catheterization data (the instantaneous pressures in the aorta and LV) in patients with complex valvular, ventricular and vascular diseases with substantial inter- and intra-patient variability with a wide range of disease (N=49) [43, 47, 143]. The model has already been validated against in vivo cardiac catheterization in patients with coarctation (N=40) [148, 149] and some sub-models have been validated against in vivo MRI data (N=57) [150]. In addition, some of the sub-models of the lumped parameter model have been used and validated previously [6, 39, 151-154].

Referring next to FIG. 29, shown therein is a Doppler-based non-invasive method 2900 for determining dynamic behavior of an aortic valve of a subject, in accordance with one or more embodiments. The aortic valve may have multiple asymmetric valve leaflets. The valve leaflets may be native valve leaflets or prosthetic valve leaflets.

Method 2900 may be used for personalized cardiology of subjects. In one or more embodiments, the subjects may be patients with valvular diseases in both pre-intervention and post-intervention status. Method 2900 may be used for monitoring, treatment planning and risk assessment in patients with valvular disease (e.g., AS) in both pre-intervention and post-intervention states. In one or more embodiments, the intervention can be TAVR and method 2900 may be used for monitoring, treatment planning and risk assessment in patients with AS in both pre-TAVR and post-TAVR states.

At 2905, method 2900 may include receiving Doppler echocardiography images of the subject. In one or more embodiments, the Doppler echocardiography images may be parasternal long-axis and parasternal short-axis views.

At 2910, method 2900 may include processing the received images to reconstruct a 3D geometry of the valve leaflets. In one or more embodiments, the 3D geometry of the valve leaflets may be reconstructed by processing parasternal long-axis view and parasternal short-axis view Doppler echocardiography images. For example, the 3D geometry of the valve leaflets may be reconstructed by measuring a base diameter, a diameter of commissures, a valve height and a length of central coaptation from the parasternal long-axis view Doppler echocardiographic image; and by measuring multiple leaflet angles from the parasternal short-axis view Doppler echocardiography image.

At 2915, method 2900 may include determining transient pressure boundary conditions for the valve leaflets using a lumped parameter model specific to the subject. In one or more embodiments, the transient pressure boundary conditions may be a transient pressure difference between a left ventricle of the subject and an aorta of the subject. In one or more embodiments, the lumped parameter model may include one or more of a left ventricle sub-model, a left atrium sub-model, an aortic valve sub-model, a mitral valve sub-model, a pulmonary circulation sub-model, and a systemic circulation sub-model.

At 2920, method 2900 may include performing a first finite element simulation to determine one or more geometrical parameters for the valve leaflets. The first finite element simulation may be based on the reconstructed 3D geometry of the valve leaflets, the determined transient boundary conditions and an initial value of one or more material parameters of the valve leaflets.

At 2925, method 2900 may include iteratively calibrating the initial value of the one or more material parameters for the subject by comparing the determined one or more geometrical parameters with a measured geometrical parameter. In one or more embodiments, the measured geometrical parameter may be an angular position or a geometric orifice area of the valve leaflets. In one or more embodiments, the measured geometrical parameter may be measured from a parasternal long-axis view and a parasternal short-axis view Doppler echocardiographic image at the peak systole time frame in which the aortic valve is in its fully open configuration.

At 2930, method 2900 may include performing a second finite element simulation, based on the calibrated one or more material parameters, to determine an indicator of the dynamic behavior of the aortic valve. In one or more embodiments, the indicator may indicate one or more of a transient 3D distribution of stress and displacement field for the valve leaflets at different time points of a cardiac cycle, a 3D deformed shape of the valve leaflets and a stiffness of the valve leaflets.

In one or more embodiments, method 2900 may further include diagnosing, monitoring or prognosing aortic valve stenosis (AS) in the subject based on the indicator. For example, the indicator indicates dynamic behavior of each of the valve leaflets. The diagnosing, monitoring or prognosing of aortic valve stenosis (AS) may be conducted pre-intervention or post-intervention. In one or more embodiments, the intervention may be a transcatheter aortic valve replacement (TAVR).

Figure 30:
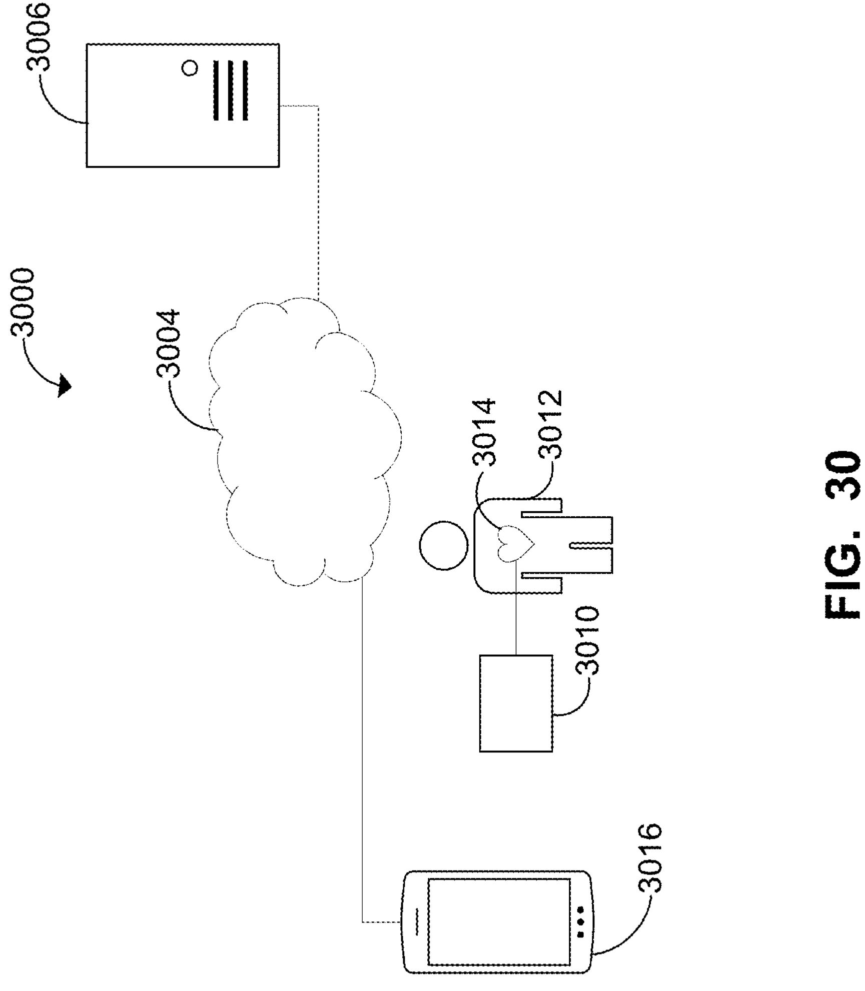
FIG. 30 shows a system for non-invasive determination of dynamic behavior of an aortic valve of a subject, in accordance with one or more embodiments.

Referring next to FIG. 30, shown therein is a system 3000 for determining dynamic behavior of an aortic valve of a subject. The aortic valve may have multiple asymmetric valve leaflets. System 3000 may include one or more user devices 3016, a network 3004, and a server 3006. Also shown is a subject 3012 having a heart 3014 and one or more cardiac monitoring devices 3010.

The one or more user devices 3016 may be used by an end user to access a software application (not shown), either via a web browser or locally at device 3016. The software application may run at server 3006 and be accessible over network 3004 to the web browser at user device 3016. Alternatively, the user of user device 3016 may download an app from an app store such as the Google® Play Store or the Apple App Store. The user device 3016 may be a desktop computer, mobile device, or laptop computer.

The user of user device 3016 may be a medical professional (not shown). Optionally, the user of user device 3016 may be the subject 3012. Each user device 3016 includes and executes a client application, such as a cardiovascular modelling application, which communicates with or otherwise receives data obtained from cardiac monitoring device 3010.

Network 3004 may be any network or network components capable of carrying data including the Internet, Ethernet, fiber optics, satellite, mobile, wireless (e.g. Wi-Fi, WiMAX), SS7 signaling network, fixed line, local area network (LAN), wide area network (WAN), a direct point-to-point connection, mobile data networks (e.g., Universal Mobile Telecommunications System (UMTS), 3GPP Long-Term Evolution Advanced (LTE Advanced), Worldwide Interoperability for Microwave Access (WiMAX), etc.) and others, including any combination of these.

Cardiac monitoring device 3010 may comprise one or more devices for monitoring the subject's heart. For example, in one embodiment the cardiac monitoring device 3010 may be a non-invasive imaging modality, such as a Doppler ultrasonograph. Data from one or more cardiac monitoring devices 3010 may be provided to the user device 3016.

In one embodiment, the functions of the user device 3016 may be performed by the cardiac monitoring device 3010. In this embodiment, the cardiac monitoring device 3010 may provide the software application for determining an indicator of dynamic behavior of an aortic valve.

The server 3006 is in network communication with the user device 3016. The server 3006 may have an application server and a database. The database and the application server may be provided on the same server, may be configured as virtual machines, or may be configured as containers. The server 3006 may run on a cloud provider such as Amazon® Web Services (AWS®).

The server 3006 may host a web application or an Application Programming Interface (API) endpoint that the user device 3016 or cardiac measurement device 3010 may interact with via network 1604. The requests made to the API endpoint of server 3006 may be made in a variety of different formats, such as JavaScript Object Notation (JSON) or eXtensible Markup Language (XML).

The database may store subject information including cardiac measurement data history, lumped parameter model data and indicator data for dynamic behavior of an aortic valve. The database may be a Structured Query Language (SQL) such as PostgreSQL or MySQL or a not only SQL (NoSQL) database such as MongoDB.

In one embodiment, the indicator of dynamic behavior of an aortic valve determined according to the embodiments described herein is communicated to a user. For example, in one or more embodiments, the indicator is communicated to a user by outputting the indicator on a display of user device 3016 or cardiac monitoring device 3010.

Figure 31:
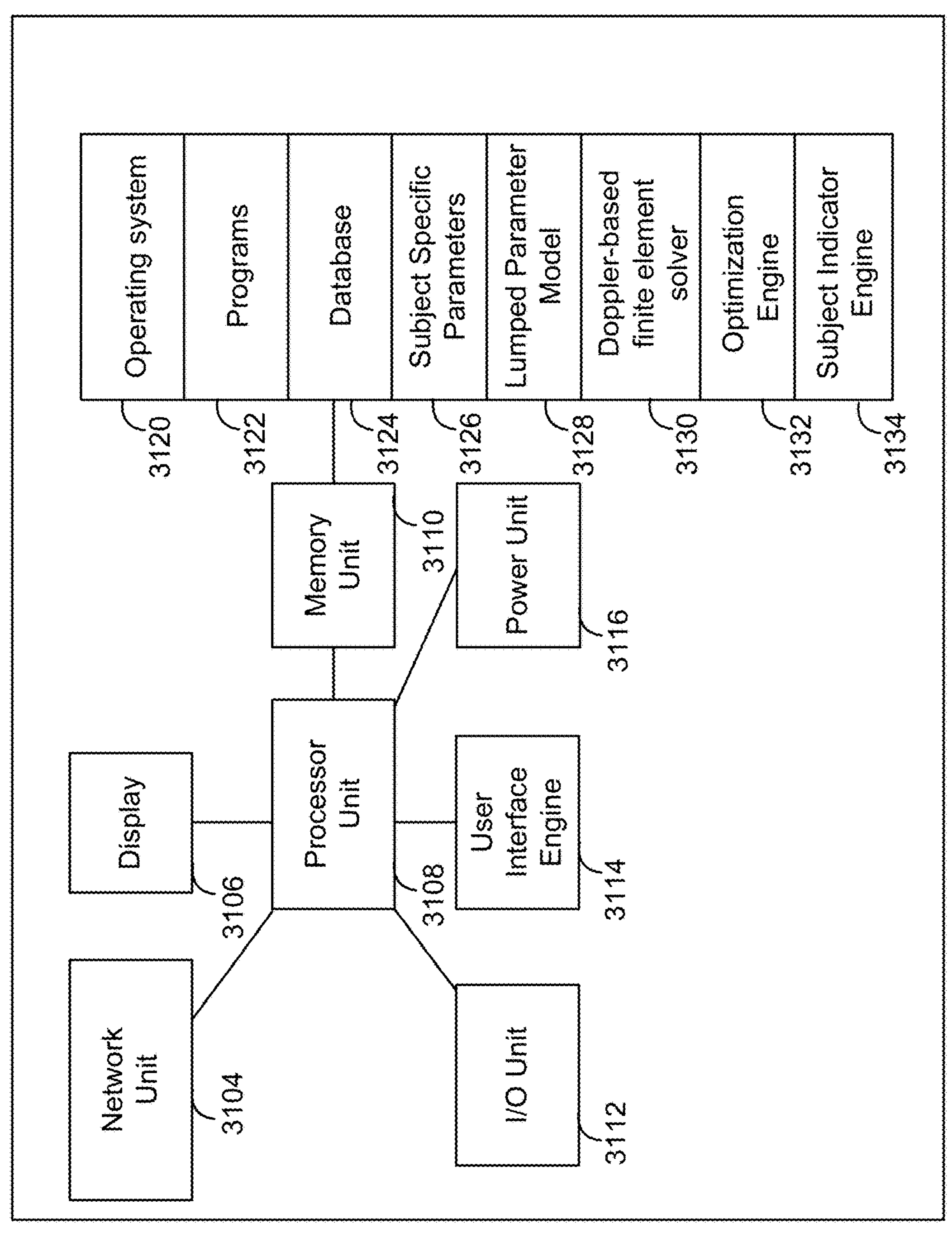
FIG. 31 shows a device for non-invasive determination of dynamic behavior of an aortic valve of a subject, in accordance with one or more embodiments.

Referring now to FIG. 31, shown therein a device 3100 for Doppler-based non-invasive determination of dynamic behavior of an aortic valve of a subject, in accordance with one or more embodiments. Device 3100 may, for example, provide the functionality of user device 3016 or cardiac monitoring device 3010. In one embodiment, the methods described herein may be performed using device 3100.

The user device 3100 includes one or more of a network unit 3104, a display 3106, a processor unit 3108, a memory unit 3110, I/O unit 3112, a user interface engine 3114, a power unit 3116.

The network unit 3104 can include wired or wireless connection capabilities. The network unit 3104 can include a radio that communicates utilizing CDMA, GSM, GPRS or Bluetooth protocol according to standards such as IEEE 802.11a, 802.11b, 802.11g, or 802.11n. The network unit 3104 can be used by the device 3100 to communicate with other devices or computers.

Network unit 3104 may communicate using a wireless transceiver to transmit and receive information via a local wireless connection with the cardiac monitoring device. The network unit 3104 may provide communications over the local wireless network using a protocol such as Bluetooth (BT) or Bluetooth Low Energy (BLE).

The display 3106 may be an LED or LCD based display, and may be a touch sensitive user input device that supports gestures.

The processor unit 3108 controls the operation of the device 3100. The processor unit 3108 can be any suitable processor, controller or digital signal processor that can provide sufficient processing power depending on the configuration, purposes and requirements of the device 3100 as is known by those skilled in the art. For example, the processor unit 3108 may be a high performance general processor. In alternative embodiments, the processor unit 3108 can include more than one processor with each processor being configured to perform different dedicated tasks. In alternative embodiments, it may be possible to use specialized hardware to provide some of the functions provided by the processor unit 3108. For example, the processor unit 3108 may include a standard processor, such as an Intel® processor or an ARM® processor.

The processor unit 3108 can also execute a user interface (UI) engine 3114 that is used to generate various UIs, for example, for reporting an indicator of dynamic behavior of an aortic valve to a user of the device 3100.

The memory unit 3110 comprises software code for implementing an operating system 3120, programs 3122, database 3124, subject specific parameters 3126, lumped parameter model 3128, Doppler-based finite element solver 3130, optimization engine 3132, and subject indicator engine 3134.

The memory unit 3110 can include RAM, ROM, one or more hard drives, one or more flash drives or some other suitable data storage elements such as disk drives, etc. The memory unit 3110 is used to store an operating system 3120 and programs 3122 as is commonly known by those skilled in the art.

The I/O unit 3112 can include at least one of a mouse, a keyboard, a touch screen, a thumbwheel, a track-pad, a track-ball, a card-reader, voice recognition software and the like again depending on the particular implementation of the device 3100. In some cases, some of these components can be integrated with one another.

The user interface engine 3114 is configured to generate interfaces for users to configure cardiac measurements, connect to the cardiac measurement device, view indicators of dynamic behavior of an aortic valve, etc. The various interfaces generated by the user interface engine 3114 are displayed to the user on display 3106.

The power unit 3116 can be any suitable power source that provides power to the device 3100 such as a power adaptor or a rechargeable battery pack depending on the implementation of the device 3100 as is known by those skilled in the art.

The operating system 3120 may provide various basic operational processes for the device 3100. For example, the operating system 3120 may be a mobile operating system such as Google® Android® operating system, or Apple® iOS® operating system, or another operating system.

The programs 3122 include various user programs so that a user can interact with the device 3100 to perform various functions such as, but not limited to, connecting to the cardiac measurement devices and viewing indicators of dynamic behavior of an aortic valve.

The database 3124 may be a database for storing cardiac measurement data from the cardiac measurement device, model parameters, lumped parameter models and determined indicators of one or more subjects. The database 3124 may receive the data from the subject specific parameters 3126 and the subject indicator engine 3134, and may further receive queries for information from the optimization engine 3132.

The database 3124 may be a database for storing initial values of one or more material parameters of the valve leaflets. In one or more embodiments, database 3124 may store subject specific information for the lumped parameter model 3128, including models or sub-model parameters generated by the optimization engine 3132.

The subject specific parameters 3126 are received cardiac measurement data from the cardiac measurement devices, optionally via the wireless transceiver and the network unit 3104. The subject specific parameters 3126 may be received and stored in database 3124. The subject specific parameters 3126 can include the subject specific material parameters described herein. The subject specific parameters 3126 may be sent to a server. The subject specific input parameters 3126 may communicate with the cardiac measurement device wirelessly, using a wired connection, or using a computer readable media such as a flash drive or removable storage device.

The lumped parameter model 3128 may be the lumped parameter model as described herein. The lumped parameter model 3128 may be represented as an electrical circuit model. The lumped parameter model 3128 may including one or more time varying functions describing portions of the model. The lumped parameter model 3128 may include one or more ordinary differential equations corresponding to sub-models or sub-portions.

The Doppler-based finite element solver 3130 may perform finite element simulations to determine one or more geometrical parameters for the valve leaflets. The Doppler-based finite element solver 3130 may perform the finite element simulations using initial values of one or more material parameters of the valve leaflets (e.g., initial values stored in database 3124). In one or more embodiments, the Doppler-based finite element solver 3130 may iteratively calibrate the initial value of the one or more material parameters specifically for the subject by comparing the determined one or more geometrical parameters with a measured geometrical parameter. The Doppler-based finite element solver 3130 may perform further finite element simulations, based on the calibrated material parameters.

The optimization engine 3132 may determine one or more subject specific solutions to the lumped parameter model 3126.

The subject indicator engine 3134 may determine one or more indicators of the dynamic behavior of the aortic valve based on the finite element simulations performed by the Doppler-based finite element solver 3130, as described herein.

In one embodiment, the methods described herein may be performed by executing instructions on computer readable media using a computer processor. Accordingly, in one embodiment there is provided a non-transitory computer readable medium comprising computer-executable instructions for determining an indicator of hemodynamic function for a subject. In one embodiment, the computer-executable instructions when executed cause a processor to determine, based on a pre-determined lumped parameter model and a plurality of input parameters for the subject, at least one sub-model parameter and an indicator of the dynamic behavior of the aortic valve of a subject.

The non-transitory computer readable medium may be stored a local or remote hard disk or hard drive (of any type, including electromechanical magnetic disks and solid-state disks), a memory chip, including, e.g., random-access memory (RAM) and/or read-only memory (ROM), cache(s), buffer(s), flash memory, optical memory such as CD(s) and DVD(s), floppy disks, and any other form of storage medium in or on which information may be stored for any duration. Different implementations of the disclosed method(s) may involve performing some or all the steps described herein in different orders or some or all of the steps substantially in parallel. Different implementations may involve performing some or all of the steps on different processors or the same processor, optionally wherein the processors are in networked communication. The functions or method steps may be implemented in a variety of programming languages known in the art. For example, such code or computer readable or executable instructions may be stored or adapted for storage in one or more machine-readable media, such as described above, which may be accessed by a processor-based system to execute the stored code or computer readable or executable instructions.

Example Results—Set 1

As described herein above, the study population included twelve patients with severe AS who underwent TAVR at St. Paul's Hospital (Vancouver, Canada).

Statistics

Data analysis was carried out offline using custom Python scripts (V.3.8) and GraphPad (V.9). All data are presented as pre-TAVR vs. post-TAVR, mean±one standard deviation (±1 SD) unless otherwise stated. The changes in clinical assessment, global hemodynamics, and valve dynamics between pre- and post-TAVR were compared using paired t-tests or Wilcoxon matched-pairs signed rank test, depending on whether the residuals were Gaussian (i.e., Shapiro-Wilk test). Correlations were calculated using a Pearson rank order test and Spearman rank order correlation test for normally and non-normally distributed data, respectively. An alpha level of <0.05 (two-tailed) was accepted as the criterion for significance.

Validation: Non-Invasive Patient-Specific Diagnostic Framework (Doppler-Based Lumped Parameter Algorithm and Doppler-Based 3-D Non-Linear Finite Element Solver) Vs. Clinical Doppler Echocardiography Data Referring now to FIG. 4, shown therein are example validation results of Doppler-based lumped parameter algorithm and Doppler-based 3-D non-linear finite element solver vs. clinical Transesophageal echocardiography data. The results of the finite element solver and high-quality transesophageal echocardiography (TEE) data have been compared in different time steps. The figures are shown in three time-steps throughout the cardiac cycle. Angular position was calculated using long axis-parasternal plane view and different visible surface areas were determined in parasternal short-axis plane views.

Angular Rotation

FIG. 4 compares the angular rotation of the right coronary cusp (RCC) and the non-coronary cusp (NCC) resulted from the disclosed Doppler-based diagnostic framework (FIG. 1) with transesophageal echocardiographic (TEE) data in 8 sample patients (out of 12 AS patients) at three varying time points in the cardiac cycle. The simulated angular rotation of the leaflets computed by the Doppler-based diagnostic framework correlated well with the ones measured using TEE in all patients (N=12) investigated in this study with angular errors ranging from 0° (minimum) to 2° (maximum).

Area

FIG. 4 investigates the visible area of all three aortic leaflets (left coronary cusp (LCC), RCC, NCC) measured by transesophageal echocardiography (TEE) along with the results from the disclosed Doppler-based diagnostic framework in 8 sample patients at three time points in the cardiac cycle. The results show very good agreements between the Doppler-based diagnostic framework and TEE in all patients (N=12) investigated in this study with errors ranging from 0-8.3%, however, the majority are under 2.0% error.

Current Clinical Assessment for Diagnosis (1) Doppler Pressure Gradient

The transvalvular pressure gradient can provide information about the severity of aortic stenosis [155, 39, 43]. The maximum observed Doppler pressure gradient on a group-level basis was 52.2±20.4 [mmHg]. Among the 12 patients evaluated, maximum recorded pressure gradients ranged from 22 [mmHg] (Patient #3) to 89 [mmHg] (Patient #16).

(2) Ejection Fraction

Ejection fraction (EF) measures the ability of the left ventricle to pump blood with each heartbeat. Normal EF in healthy individuals with proper cardiac function resides above 41% (Lang et al., 2015). Group-level statistical analysis of the example results revealed a mean EF of 0.36±0.14 for the 12 patients. Of the 12 patients, the left ventricular EF ranged from 0.08 (Patient #16) to 0.55 (Patient #13). 7 out of the 12 patients exhibited an EF lower than 0.41.

(3) Ejection Time and Acceleration Time

Acceleration time (AT) is a parameter that represents the time it takes for the aortic valve to open and reach peak aortic jet velocity, while the ejection time (ET) is the amount of time between the opening and closing of the aortic valve [157]. These parameters explaining ejection dynamics provide a viable alternative when there are discrepancies between the aortic valve area and pressure gradient during systole, both of which are commonly used to evaluate AS severity [158]. Values of AT >0.094 [s] and AT/ET >0.35 are often indicative of severe aortic stenosis in native aortic valves [158]. All 12 patients in this study exhibited values of greater than 0.094 [s] (0.144±0.021 [s]) for acceleration time. Furthermore, 11 of the 12 patients evaluated had an AT/ET value above 0.35 (0.433±0.057 [s]).

(4) Diastolic Dysfunction

Diastolic dysfunction grades ranged from 1-3 in the example group of 12 patients with an average grade of 2.25. 3 out of the 12 patients had a grade of 1, 3 patients with a grade of 2, and the rest of the patients graded a 3. As recommended by ASE guidelines [159], the E wave to A wave (E/A) ratio ≥2 could independently be considered a Grade 3 diastolic dysfunction with increased left atrium pressure and E/A ratio ≤0.8 (E ≤50 cm/s) as Grade 1 diastolic dysfunction with normal left atrium pressure. Indeed, most patients in the example study (9 out of 12) had either E/A ratio ≥2 or E/A ratio ≤0.8 and therefore, considered as Grade 3 and 1 diastolic dysfunction (for all the patients, E/e' ratio, tricuspid regurgitation velocity and left atrium volume index were also assessed). For the other 3 patients in the example study with 0.8≤E/A ratio s 2, the decision for Grade 2 diastolic dysfunction was made based on the availability of at least two of the following conditions: average E/e' ratio >14, tricuspid regurgitation velocity >2.8 m/s and left atrium (LA) volume index >34 ml/$m^2$ [159].

Figure 5:
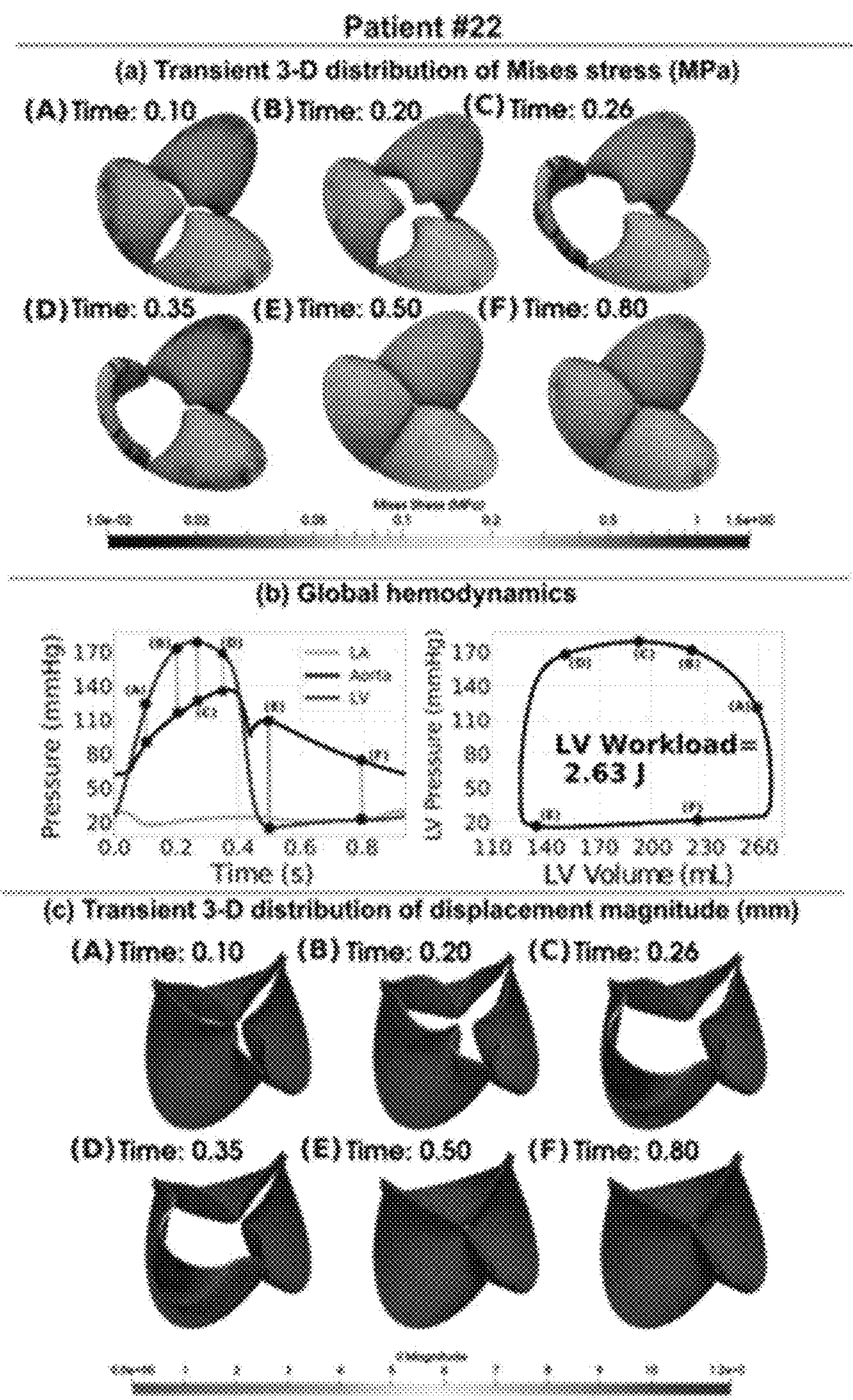
FIG. 5 shows valve dynamics and global hemodynamics in an example patient in pre-intervention status.

Global Hemodynamics Computed by Doppler-Based Diagnostic Lumped Parameter Algorithm Reference is next made to FIGS. 5-10. FIG. 5 shows valve dynamics and global hemodynamics in an example patient #22 in pre-intervention status—(a) transient distribution of the mises stress over the full cardiac cycle; (b) global hemodynamics: LV workload; aorta, left atrium, and LV pressures; (c) transient 3-D distribution of displacement magnitude over the entire cardiac cycle illustrating each point of the aortic valve and its movement along the computational domain. Patient #22: severe aortic stenosis (EOA=0.8 $cm^2$), moderate aortic regurgitation, moderate mitral regurgitation, hypertension, ejection fraction: 34%, brachial pressures: 63 and 136 mmHg. FIG. 6 shows Doppler-based patient-specific material properties for the example patient #22 of FIG. 5. (a) Doppler echocardiographic images compared against the results of the doppler-based finite element solver; (b) Doppler-based calibrated material properties with individual leaflet stiffness calculated based on parameter $C_{10}$ which represents the isotropic portion of the energy density function (Equation 4); (c) Computed tomographic images of the aortic valve along with the described calcific regions of individual leaflets.

Figure 7:
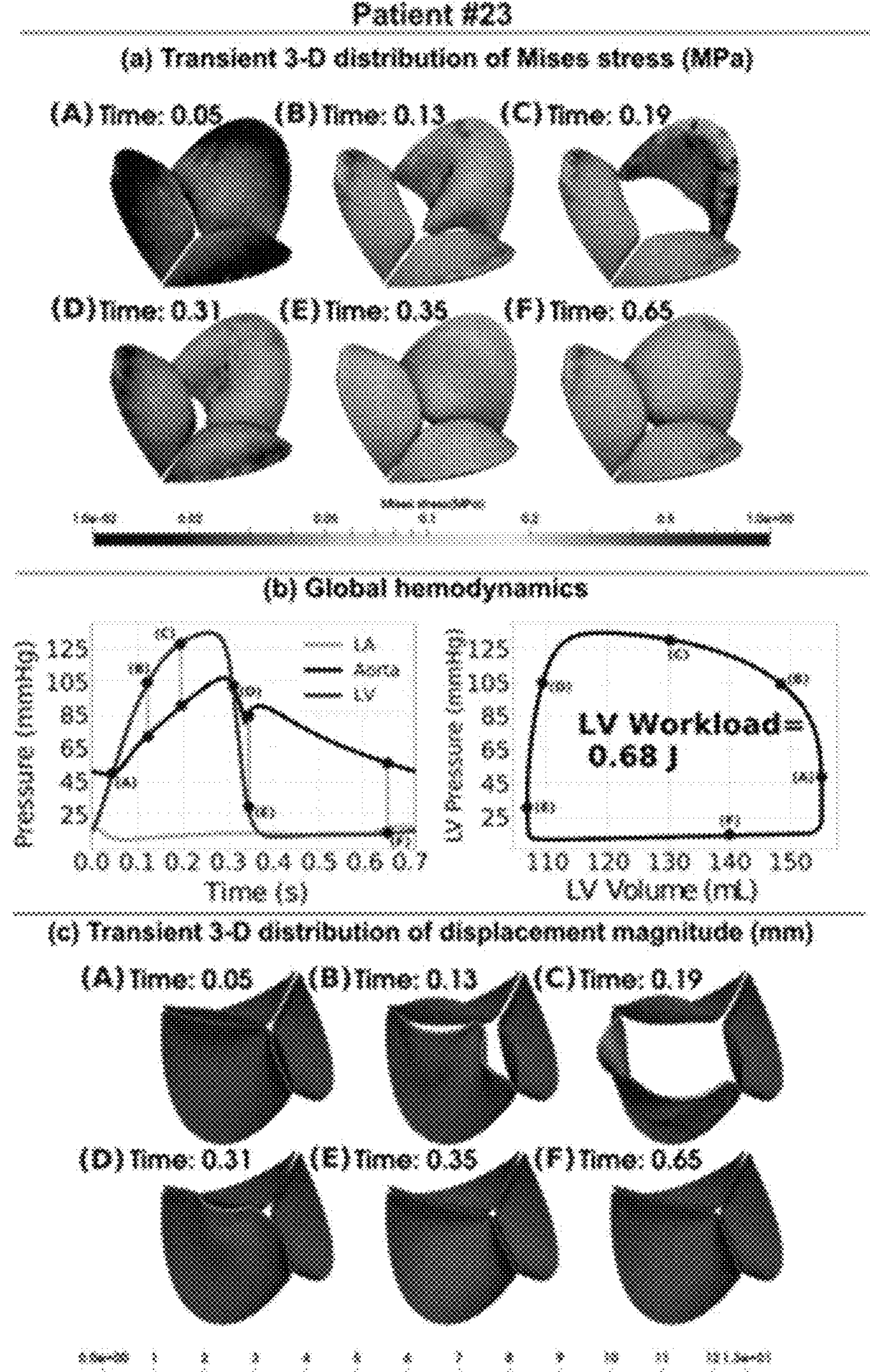
FIG. 7 shows valve dynamics and global hemodynamics in another example patient in pre-intervention status.

FIG. 7 shows valve dynamics and global hemodynamics in another example patient #23 in pre-intervention status. (a) Transient distribution of the mises stress over the full cardiac cycle; (b) Global hemodynamics: LV workload; aorta, left atrium, and LV pressures; (c) Transient 3-D distribution of displacement magnitude over the entire cardiac cycle illustrating each point of the aortic valve and its movement along the computational domain. Patient #23: severe aortic stenosis (EOA=0.6 $cm^2$), dyslipidemia, mild mitral regurgitation, coronary artery disease, ejection fraction: 42%, brachial pressures: 51 and 107 mmHg. FIG. 8 shows Doppler-based patient-specific material properties in the example patient #23 of FIG. 7. (a) Doppler echocardiographic images compared against the results of the doppler-based finite element solver; (b) Doppler-based calibrated material properties with individual leaflet stiffness calculated based on parameter $C_{10}$ which represents the isotropic portion of the energy density function (Equation 4); (c) Computed tomographic images of the aortic valve along with the described calcific regions of individual leaflets.

Figure 9:
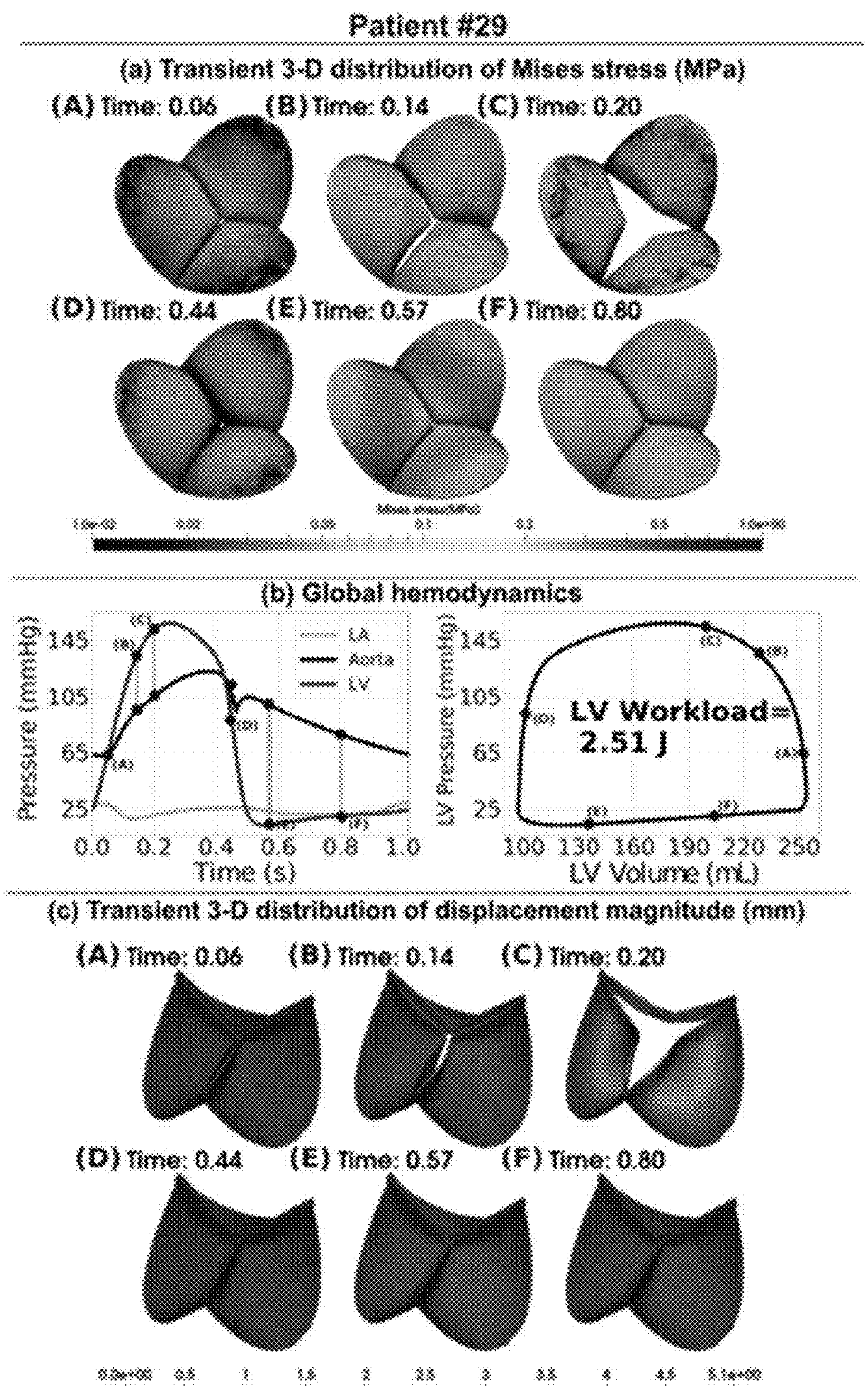
FIG. 9 shows valve dynamics and global hemodynamics in another example patient in pre-intervention status.

FIG. 9 shows valve dynamics and global hemodynamics in another example patient #29 in pre-intervention status. (a) Transient distribution of the mises stress over the full cardiac cycle; (b) Global hemodynamics: LV workload; aorta, left atrium, and LV pressures; (c) Transient 3-D distribution of displacement magnitude over the entire cardiac cycle illustrating each point of the aortic valve and its movement along the computational domain. Patient #29: severe aortic stenosis (EOA=0.8 $cm^2$), coronary artery disease, moderate to severe mitral regurgitation, mild aortic regurgitation, ejection fraction: 28%, brachial pressures: 62 and 123 mmHg. FIG. 10 shows Doppler-based patient-specific material properties in the example patient #29 of FIG. 9. (a) Doppler echocardiographic images compared against the results of the doppler-based finite element solver; (b) Doppler-based calibrated material properties with individual leaflet stiffness calculated based on parameter $C_{10}$ which represents the isotropic portion of the energy density function (Equation 4); (c) Computed tomographic images of the aortic valve along with the described calcific regions of individual leaflets.

In the presence of AS, the heart is overloaded since the healthy instantaneous LV pressure and/or volume are altered. Metrics of cardiac function computed by the disclosed Doppler-based lumped parameter algorithm (FIG. 1, Panel a) were investigated as follows:

(1) Workload

LV workload is calculated as the area encompassed by the LV pressure and volume loop. The ideal LV workload is less than 1 [J] in healthy individuals with proper cardiac function [43, 47, 154]. FIGS. 5*b*, 7*b*, and 9*b* exhibits extremely high LV workload with values of 2.63 [J] and 2.51 [J] in patients #22 and #29 and 0.68 [J] in Patient #23. Such high values of LV workload, specifically in sample patients #22 and #29, are critical as they are expended approximately 100,000 times a day resulting in an extreme loss. The results from the disclosed Doppler-based lumped parameter algorithm exhibit an increased group level LV workload compared to healthy individuals (1.8±0.8 [J]) where 10 of the 12 patients had an LV workload greater than 1 [J].

(2) Normalized Workload

Normalized LV workload to stroke volume is the energy required to eject 1 ml of blood through the valvulo-arterial system [47, 150]. Group level statistical analysis revealed similar results to the LV workload computed by the disclosed Doppler-based diagnostic framework. The normalized LV workload for patients #22, #23, and #29 was calculated to be 0.019 [J/ml], 0.014 [J/ml], and 0.016 [J/ml], respectively. Of the 12 patients, the group level average was calculated as 0.017±0.003 [J/ml].

(3) LV Pressure

LV pressure is a crucial metric to assess cardiac function as LV hypertrophy and failure is often a result of pressure overload. Maximum LV pressure observed in healthy is below 120 [mmHg] [160]. FIGS. 5*b*, 7*b*, and 9*b* illustrate maximum LV pressure magnitudes of 178 [mmHg], 134.4 [mmHg], and 156 [mmHg] for patients #22, #23 and #29, respectively. Similar to LV workload, these simulated values using the disclosed Doppler-based lumped parameter algorithm show the correlation between AS severity and elevated LV pressure gradient. Group level statistical analysis revealed similar trends, as 10 of the 12 patients exhibited elevated maximum LV pressure measurements with a mean value of 166±32 [mmHg]. Increased LV pressure contributes to elevated LV workload and is a leading factor to LV hypertrophy and cardiac failure.

(4) Systemic Arterial Compliance

Arterial stiffening reduces the compliance of the systemic arterial system and is commonly linked to the development and progression of hypertension, increased LV afterload, decreased coronary flow, increased myocardial demand and development of LV dysfunction [161]. Systemic arterial compliance (stroke volume index/pulse pressure, SAC), indicative of arterial hemodynamics, is inversely related to aortic stenosis morbidity risk [162], where higher risk is correlated with a lower SAC value (less than 0.64 ml/$m^2$/mmHg). 5 of the 12 patients in the example study had a SAC value below 0.64 ml/$m^2$/mmHg (0.80±0.30 [ml/$m^2$/mmHg]; N=12). The simulated values of SAC across all patients ranged from 0.40 [ml/$m^2$/mmHg] (Patient 12) to 1.29 [ml/$m^2$/mmHg] (Patient #29).

Valve Dynamics Computed by Non-Invasive Diagnostic Framework (Doppler-Based Lumped Parameter Algorithm and 3-D Non-Linear Finite Element Solver)

Mechanical stresses play an important role in the development of calcification and deterioration of aortic valve leaflets [7, 17, 24, 26, 27]. In following, 3-D the Mises stress (the deviatoric format of principle stress, i.e., $$\left(\sqrt{\frac{(\sigma_1-\sigma_2)^2+(\sigma_2-\sigma_3)^2+(\sigma_3-\sigma_1)^2}{2}}\right),$$

3-D major principal stress (the maximum value of the three principal stresses, i.e., maximum values of $\sigma_1$, $\sigma_2$ and $\sigma_3$) as well as displacement resulted from the disclosed Doppler-based computational framework (Doppler-based lumped parameter algorithm and 3-D non-linear finite element solver; FIG. 1) are described.

(1) 3-D Mises Stress

FIGS. 5*a*, 7*a*, and 9*a* illustrate the transient 3-D distribution of Mises stress over the aortic valve leaflets throughout the entire cardiac cycle. All 3 sample patients (#22, #23, #29) exhibited similar stress patterns throughout the phases of the cardiac cycle. At the start of both systole and start of diastole, when aortic and LV pressures are nearly equal, stress across the leaflets is minimized. Mises stress across the leaflets is greatly increased at peak systole as well as peak diastole which both occur when the difference in aortic and LV pressure is the greatest. When the aortic valve is closed, the stress appears to be evenly distributed across all leaflets, however, at peak systole when the valve is open, the leaflets that do function and provide a path for blood flow appear to have more concentrated stress contours. Stress distribution across the aortic valve leaflets for each patient is a function of the leaflet 3-D geometry and stiffness, as well as patient-specific transvalvular loads. Given that during pathological conditions, these parameters differ across leaflets, the local stress distributions of each leaflet will vary significantly at each time point during the cardiac cycle. Additionally, due to the differences between material properties of a healthy vs. pathological leaflet, stress distribution abnormalities (e.g., regions with unexpected higher concentrated stress) are more prone to emerge in presence of pathological conditions such as calcification [17, 72, 163-165]. In the example study, this increase in localized stress is observed in the functioning leaflet of patients #22 and #23 (FIGS. 5*a* and 7*a*). For a healthy valve with functioning leaflets at the fully open configuration, a flexion occurs at the root of the leaflet followed by higher stress distribution [72, 105, 166]. Several studies suggest that high stress at the region of the leaflet close to the root is linked to the calcification initiation [27, 133, 167]. However, after calcification progression from the root to the tip of the leaflet, this stress pattern changes drastically which is associated with various high stress regions across the leaflets [168]. Taken together, calcification progression does not seem to be confined to any specific local area of a leaflet. Such alterations in stress distribution are distinguishable in stiffer leaflets, in which the concentrated stress areas are more prevalent than in healthy leaflets, as well as occurring in more random regions the leaflet. As shown in FIGS. 5*a*,7*a* and 9*a*, the example results show that the regions with higher stress appear in different regions of leaflets rather than only the root. As such, the example results partly support the observation that calcification patterns could significantly differ for each patient after its initiation. Patient #22 exhibited maximum measured Mises stress of 5.0 [MPa] and 1.4 [MPa] in systole and diastole, respectively, both present on the NCC. Similar to patient #22, patient #23 also recorded maximum Mises stress on the NCC in both systole and diastole with values of 7.7 [MPa] and 1.3 [MPa], respectively. Moreover, patient #29 also displayed maximum Mises stress over the NCC with values of 5.9 [MPa] and 1.4 [MPa] during systole and diastole, respectively. The computed mean Mises stress over all leaflets, NCC leaflets, LCC leaflets and RCC leaflets throughout the entire cardiac cycle for sample patients #22, #23, and #29 are reported in Table 3.

TABLE 3

Mean Mises stress over full-cardiac cycle in patients

| | Mean Mises stress over all leaflets [Mpa] | Mean Mises stress Left coronary cusp [Mpa] | Mean Mises stress Right coronary cusp [Mpa] | Mean major principal stress Non-coronary cusp [Mpa] |
|---|---|---|---|---|
| Patient #22 | 0.123 | 0.113 | 0.107 | 0.149 |
| Patient #23 | 0.109 | 0.0945 | 0.088 | 0.145 |
| Patient #29 | 0.157 | 0.161 | 0.143 | 0.168 |
| All 12 patients | 0.138 ± 0.033 | 0.141 ± 0.028 | 0.131 ± 0.043 | 0.146 ± 0.050 |

(2) 3-D Principal Stress

The computed mean major principal stress over all leaflets, NCC leaflets, LCC leaflets and RCC leaflets throughout the entire cardiac cycle for sample patients #22, #23, and #29 are reported in Table 4. The mean major principal stresses in all 12 AS patients through the full cardiac cycle are as follows: over all leaflets: 0.122±0.043 [MPa], over LCC leaflets: 0.125±0.061 [MPa], over RCC leaflets: 0.114±0.044 [MPa], and over NCC leaflets: 0.125±0.041 [MPa].

TABLE 4

Mean major principal stress over full-cardiac cycle in patients

| | Mean major principal stress over all leaflets [Mpa] | Mean major principal stress Left coronary cusp [Mpa] | Mean major principal stress Right coronary cusp [Mpa] | Mean major principal stress Non-coronary cusp [Mpa] |
|---|---|---|---|---|
| Patient #22 | 0.079 | 0.075 | 0.07 | 0.093 |
| Patient #23 | 0.072 | 0.063 | 0.058 | 0.096 |
| Patient #29 | 0.11 | 0.113 | 0.1 | 0.117 |
| All 12 patients | 0.122 ± 0.043 | 0.125 ± 0.061 | 0.114 ± 0.044 | 0.125 ± 0.041 |

(3) Displacement Magnitude

The displacement vector represents the various components of each point of the aortic valve and its movement along the computational domain and could be a useful tool for monitoring aortic valve movements [169]. FIGS. 5*c*, 7*c*, and 9*c* illustrate the displacement magnitude of the aortic valve leaflets in 3 (of 12) sample patients. The maximum displacement magnitudes in these figures are 12.0 [mm] (NCC), 15.0 [mm](NCC), and 5.5 [mm] (LCC) for patients #22, #23, and #29, respectively. It is evident through these figures which leaflets of the aortic valve are preventing adequate blood flow as displacement values are minimal across the majority of the valve. The open area between the leaflets is known as the geometric orifice area (GOA) while the effective orifice area (EOA) is the area in which blood flows through the valve, which is slightly smaller than EOA [170]. The stiffness and mechanical properties of the diseased aortic valve prevents the valve from opening properly and thus GOA and EOA are substantially reduced. The results from the disclosed computational framework demonstrate a mean maximum displacement of 4.30±2.23 [mm], 4.03±1.81 [mm], and 7.19±3.71 [mm] in all 12 AS patients for the LCC, RCC, and NCC, respectively.

(4) Patient-Specific Doppler-Based Material Properties of the Valve Leaflets

FIGS. 6*b*, 8*b* and 10*b* illustrate the patient-specific material properties of patients #22, #23, and #29, respectively. Leaflet stiffness was evaluated by parameter $C_{10}$ for all three aortic valve leaflets for each patient. The isotropic portion of the energy density function is represented by the $C_{10}$ parameter (Equation 4). The greater the $C_{10}$ value, the more resistant the leaflets are to opening when the left ventricle pressure exceeds the aorta pressure during systole [171, 172]. Doppler images were used to calibrate each leaflet separately in the described framework. As a result, each leaflet has a specific $C_{10}$ parameter. Leaflet stiffness ranged from 0.8-1.0 [MPa] with an average of 0.93 [MPa], 0.45-1.2 [MPa] with an average of 0.98 [MPa], and 0.75-1.04 [MPa] with an average of 0.88 [MPa], for patients #22, #23, and #29, respectively. Furthermore, on a group level basis, average stiffness among all aortic valve leaflets had similar values (LCC=0.90±0.37 [MPa], RCC=1.03±0.26 [MPa], NCC=0.88±0.43 [MPa]), however, certain patients exhibited wide ranges of stiffness among their leaflets (e.g., Patient #12 ranged between 0.39 [MPa] (NCC)-1.2 [MPa] (LCC)). Furthermore, there were wide variations in stiffness among patients (LCC: 0.4-1.66 [MPa], RCC: 0.72-1.48 [MPa], NCC: 0.39-1.60 [MPa]).

Prognosis Value of Pre-TAVR Global Hemodynamic and Valve Dynamic Parameters

Figure 11:
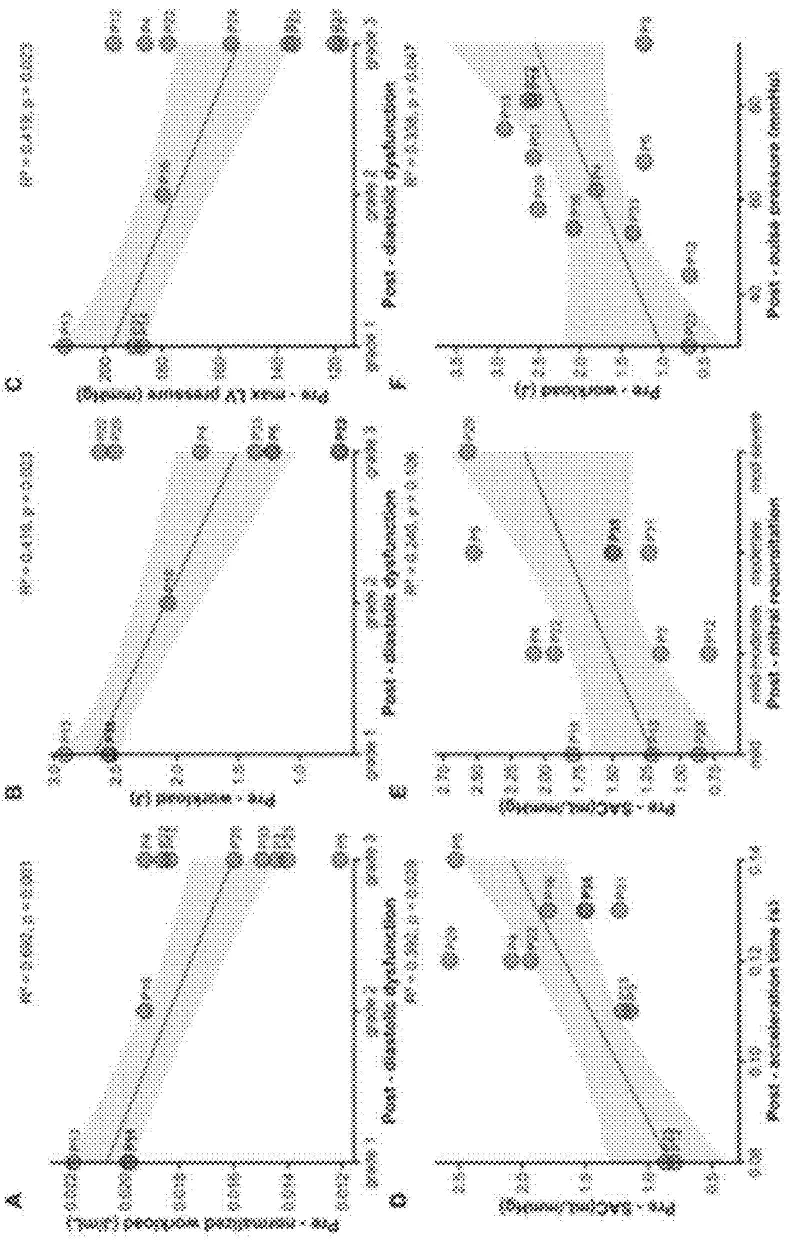
FIG. 11 shows Spearman's correlation between pre-TAVR global hemodynamics computed by Doppler-based patient-specific lumped parameter algorithm and post-TAVR clinical metrics to assess outcome of the patients (n=12), in accordance with one or more embodiments.
Figures 12A, 12B, 12C, 12D, 12E, 12F, 12G, 12H, 12I, 12J:
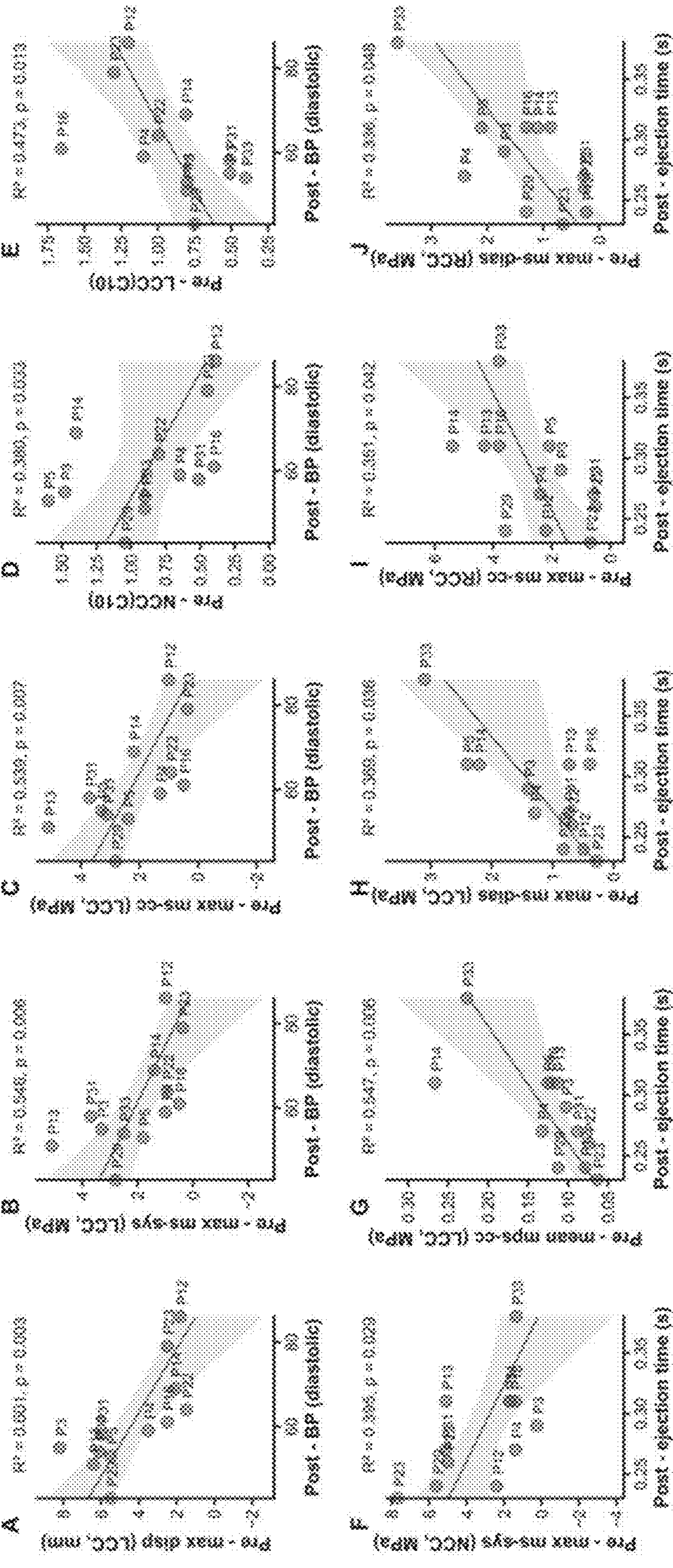
FIGS. 12A-12T (collectively referred to herein as FIG. 12) show Spearman's correlation between pre-TAVR valve dynamics computed by Doppler-based patient-specific lumped parameter algorithm and 3-D non-linear finite element solver and post-TAVR clinical metrics to assess outcome of the patients as well as post-TAVR global hemodynamics computed by Doppler-based patient-specific lumped parameter algorithm (n=12), in accordance with one or more embodiments.
Figures 12K, 12L, 12M, 12N, 12O, 12P, 12Q, 12R, 12S, 12T:
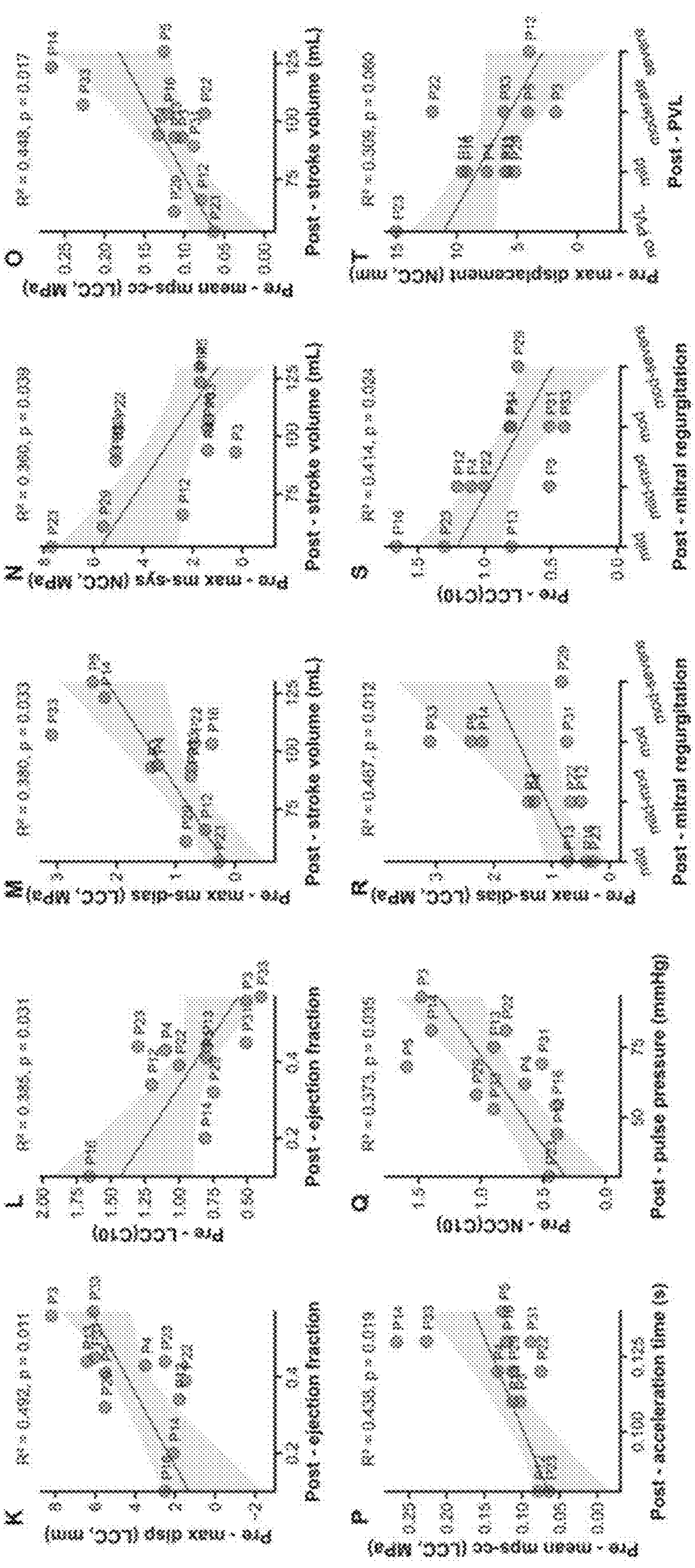

Reference is next made to FIGS. 11 and 12. FIG. 11 shows Spearman's correlation between pre-TAVR global hemodynamics computed by Doppler-based patient-specific lumped parameter algorithm and post-TAVR clinical metrics to assess outcome of the patients (n=12), in accordance with one or more embodiments. FIG. 11—A. Scatter plot of post-TAVR diastolic dysfunction versus pre-TAVR normalized workload; B. Scatter plot of post-TAVR diastolic dysfunction versus pre-TAVR workload; C. Scatter plot of post-TAVR diastolic dysfunction versus pre-TAVR max LV pressure; D. Scatter plot of post-TAVR acceleration time versus pre-TAVR systemic arterial compliance; E. Scatter plot of post-TAVR mitral regurgitation versus pre-TAVR systemic arterial compliance; F. Scatter plot of post-TAVR pulse pressure versus pre-TAVR workload.

FIG. 12 shows Spearman's correlation between pre-TAVR valve dynamics computed by Doppler-based patient-specific lumped parameter algorithm and 3-D non-linear finite element solver and post-TAVR clinical metrics to assess outcome of the patients as well as post-TAVR global hemodynamics computed by Doppler-based patient-specific lumped parameter algorithm (n=12), in accordance with one or more embodiments. FIG. 12—A. Scatter plot of post-TAVR diastolic arterial pressure versus pre-TAVR LCC maximum displacement; B. Scatter plot of post-TAVR diastolic arterial pressure versus pre-TAVR LCC maximum Mises stress during systole; C. Scatter plot of post-TAVR diastolic arterial pressure versus pre-TAVR LCC maximum Mises stress during the full cardiac cycle; D. Scatter plot of post-TAVR diastolic arterial pressure versus pre-TAVR NCC stiffness; E. Scatter plot of post-TAVR diastolic arterial pressure versus pre-TAVR LCC stiffness; F. Scatter plot of post-TAVR ejection time versus pre-TAVR NCC maximum Mises stress during systole; G. Scatter plot of post-TAVR ejection time versus pre-TAVR LCC mean major principal stress during the full cardiac cycle; H. Scatter plot of post-TAVR ejection time versus pre-TAVR LCC maximum Mises stress during diastole; I. Scatter plot of post-TAVR ejection time versus pre-TAVR RCC maximum Mises stress during the full cardiac cycle; J. Scatter plot of post-TAVR ejection time versus pre-TAVR RCC maximum Mises stress during diastole; K. Scatter plot of post-TAVR ejection fraction versus pre-TAVR LCC maximum displacement; L. Scatter plot of post-TAVR ejection fraction versus pre-TAVR LCC stiffness; M. Scatter plots of post-TAVR stroke volume versus pre-TAVR LCC maximum Mises Stress during diastole; N. Scatter plots of post-TAVR stroke volume versus pre-TAVR NCC maximum Mises stress during systole; O. Scatter plots of post-TAVR stroke volume versus pre-TAVR LCC mean major principal stress during the full cardiac cycle; P. Scatter plot of post-TAVR acceleration time versus pre-TAVR LCC mean major principal stress during the full cardiac cycle; Q. Scatter plot of post-TAVR pulse pressure versus pre-TAVR NCC stiffness. R. Scatter plot of post-TAVR mitral regurgitation versus pre-TAVR LCC maximum Mises stress during diastole; S. Scatter plot of post-TAVR mitral regurgitation versus pre-TAVR LCC stiffness; T. Scatter plot of post-TAVR paravalvular leakage versus pre-TAVR NCC maximum displacement. Note: ms—mises stress, mps—major principal stress, disp—displacement, cc—during full cardiac cycle, sys—during systole, dias—during diastole, LCC—left coronary cusp, RCC—right coronary cusp, NCC—non-coronary cusp.

Spearman's correlations were computed to assess the degree of association between pre-TAVR global hemodynamics & valve dynamics and post-TAVR parameters, e.g., clinical metrics to assess outcome of the patients, which may help predicting the post-TAVR complications when pre-TAVR valve dynamics/global hemodynamics are known. From the Spearman's correlations (n=12), the strongest correlations (r>0.5) were plotted: (1) for post-TAVR clinical metrics to assess the outcomes of the patients with pre-TAVR global hemodynamics (FIG. 11; via the disclosed Doppler-based patient-specific lumped parameter algorithm) and (2) for post-TAVR clinical metrics to assess the outcomes of the patients with pre-TAVR valve dynamics (FIG. 12; via the disclosed Doppler-based patient-specific lumped parameter algorithm and 3-D non-linear finite element solvers).

Pre-TAVR normalized workload (FIG. 11, panel A), workload (FIG. 11, panel B), and max LV pressure (FIG. 11, panel C) were negatively correlated with diastolic arterial pressure post-TAVR. Pre-TAVR systemic arterial compliance positively correlated with acceleration time (FIG. 11, panel D) and mitral regurgitation (FIG. 11, panel E) post-TAVR. Post-TAVR pulse pressure was positively correlated with pre-TAVR workload (FIG. 11, panel F).

FIG. 12, panels A-D show strong negative correlations between post-TAVR diastolic arterial pressure and pre-TAVR LCC maximum displacement (FIG. 12, panel A), LCC maximum Mises stress during systole (FIG. 12, panel B), LCC maximum Mises stress during the full cardiac cycle (FIG. 12, panel C), NCC stiffness (FIG. 12, panel D). While pre-TAVR LCC stiffness correlated negatively with diastolic arterial pressure post-TAVR (FIG. 12, panel E). Post-TAVR ejection time negatively correlated with pre-TAVR NCC maximum Mises stress during systole (FIG. 12, panel F), and positively correlated with pre-TAVR LCC mean major principal stress during the full cardiac cycle (FIG. 12, panel G, LCC maximum Mises stress during diastole (FIG. 12, panel H, RCC maximum Mises stress during the full cardiac cycle (FIG. 12, panel I) and RCC maximum Mises stress during diastole (FIG. 12, panel J). Post-TAVR ejection fraction positively correlated with pre-TAVR LCC maximum displacement (FIG. 12, panel K) and negatively correlated with pre-TAVR LCC stiffness (FIG. 12, panel L). Post-TAVR, stroke volume positively correlated with pre-TAVR LCC maximum Mises Stress during diastole (FIG. 12, panel M) and pre-TAVR LCC mean major principal stress during the full cardiac cycle (FIG. 12, panel O), and negatively correlated with pre-TAVR NCC maximum Mises stress during systole (FIG. 12, panel N). Post-TAVR acceleration time positively correlated with pre-TAVR LCC mean major principal stress during the full cardiac cycle (FIG. 12, panel P). Post-TAVR pulse pressure positively correlated with pre-TAVR NCC stiffness (FIG. 12, panel Q). Similarly, pre-TAVR LCC maximum Mises stress during diastole positively correlated with mitral regurgitation post-TAVR (FIG. 12, panel R). Pre-TAVR LCC stiffness negatively correlated with mitral regurgitation post-TAVR (FIG. 12, panel S). Post-TAVR paravalvular leakage negatively correlated with pre-TAVR NCC maximum displacement.

(1) Discussion

The proper function of the aortic valve relies on the interaction between the structural properties of the valve itself and the surrounding hemodynamic and mechanical environment [17, 89]. The aortic valve experiences structural deformations due to the pressure loads imposed on the leaflets caused by ventricular and ascending aortic pressures. Abnormal pressure loads lead to abnormal mechanical strain and stresses on the aortic valve leaflets which has been shown to promote calcification on the aortic valve [60, 72, 173]. Cardiovascular events, coronary disease and all-cause mortality are associated with valvular calcification [52, 174, 175]. When calcification occurs in the heart valves, the disease may progress from sclerosis to stenosis, in which the valvular area is reduced, and the valve leaflet function is impaired [174, 176]. Indeed, the calcification process is complex and is divided into two phases: initiation and propagation [55, 177, 178] in which the increased mechanical stresses on the valve are the main driving force [55]. Mechanical stresses on the valves: (1) cause endothelial damage and start the initiation phase, which involves inflammation and the infiltration of lipids [55, 177, 178]; (2) cause transforming the valvular interstitial cells into an osteoblastic phenotype, which triggers the propagation phase of calcification and accelerates calcification and fibrosis [55, 177-179]. Abnormal valve dynamics are associated with adverse outcomes, and therefore must be quantified correctly to allow for accurate risk stratification and to potentially improve patient outcomes.

To effectively diagnose and treat aortic stenosis, the relationship between transient pressure loads and valve dynamics must be closely considered to understand the function of the valve and progression of the disease [17, 76, 171]. Although it is clear that the proper diagnosis and evaluation of AS severity does not rely on a single value for aortic velocity, transaortic pressure gradient or valve area, the basis of many clinical decisions including diagnosis and evaluation of AS often involves the evaluation of single anatomical features [180]. More comprehensive measurements and calculations are crucial for the accurate evaluation of disease severity, which can better lead to the prediction of optimal intervention timing [39]. Indeed, detailed valve dynamics are required for a patient-specific treatment approach [70]. Often used for intervention timing is the emergence of symptoms [181]. Calcification patterns often occur non-uniformly on leaflets and each leaflet may have a different level of calcification [55]. Consequently, these patterns have significant effects on the outcome of treatment, including transcatheter aortic valve replacement (TAVR) [73, 53]. Using valve biomechanics, symptom emergence and disease progression can be predicted before symptoms appear [39]. Operative mortality has been shown to occur in 8-33% of patients due to the diagnostic challenges and limited access to valve dynamics [182]. This demonstrates the need for tools to accurately quantify the valve dynamics for the effective diagnosis and treatment of AS [17, 89].

Despite incredible advancements in medical imaging, imaging on its own cannot assess valve dynamics and biomechanical force information nor it is predictive [43, 171]. Cardiac catheterization has commonly been used as the standard method for obtaining features such as pressure and flow, however, it is invasive, expensive and has high risk [43, 183, 184]. Doppler echocardiography is a non-invasive, risk free and versatile tool for evaluating valve structure, function, and hemodynamics [175]. However, it is limited to aortic valvular velocity, pressure gradients and color Doppler imaging [172]. Computed tomography has great applications for dimensional measurements for components that are flexible, difficult to reach or have internal geometry [185]. Despite the advantages CT possesses, it has a poor temporal resolution, uses contrast agents and emits ionizing radiation which has several risks, including the development of cancer [186, 187]. Magnetic resonance imagining is also a powerful tool that can provide valuable information regarding valve motion, structure and flow from various orientations, however, it has poor temporal resolution, is lengthy and cannot be used in patients that have implanted metallic devices or pacemakers [187, 188]. Despite all the advantages that catheterization, DE, CT and MRI offer, none of these tools can quantify valvular dynamics. Imaging techniques alone cannot accurately quantify the valve structure, motion or distribution of stress and strain on each leaflet of the aortic valve [38, 183, 189].

Persistent monitoring and early diagnosis of aortic valve stenosis is key in the prevention and treatment of patients [173]. Herein is provided, a highly innovative non-invasive Doppler-based computational-mechanics framework that can function as a diagnostic tool for patients with AS in both pre and post intervention states. This Doppler-based diagnostic framework may be based on an innovative Doppler-based patient-specific lumped parameter algorithm, 3-D non-linear finite element solver and 3-D Doppler-based geometry reconstruction that satisfies all 6 requirements for developing a clinically effective computational diagnostic framework to quantify valve dynamics (e.g., transient 3-D distribution of stress or displacement, 3-D deformed shape of leaflets, geometric orifice area and angular positions of leaflets).

Calcification in the cardiovascular system is frequently associated with adverse outcomes and is a common cause of aortic stenosis [23, 168, 169]. Aortic valve calcification scoring can be used as a diagnostic method to confirm disease severity as well as for intervention planning and prediction [56, 170]. As one example, the success of valve intervention (e.g., TAVR) is strongly influenced by presence of the asymmetric calcification pattern [54]. As a result, clinical decision-making and surgical planning require a thorough understanding of material properties and asymmetric physical features of native aortic valve leaflets. Doppler echocardiography is limited for analyzing calcification, however, calcium evaluation can be effectively performed using contrast CT imaging [52, 55, 35]. Herein is provided, a Doppler-based lumped parameter algorithm and a finite element solver which can calculate the stiffness and material properties of individual leaflets. The individual leaflet stiffness calculated using this Doppler-based computational framework show a strong correspondence with the degree of calcification obtained from the CT images: the more flexible the leaflet, the less calcified it is. For example, the leaflets with lower degrees of calcification measured using CT (FIGS. 6*c*, 8*c* and 10*c*), indeed, showed lower stiffnesses as calculated by the disclosed Doppler-based computational framework (FIGS. 6*b*, 8*b* and 10*b*). The asymmetric leaflet openings in FIGS. 6*a* (Patient #22), 8*a* (Patient #23), and 10*a* (patient #29) show correspondence between the leaflet stiffness and the degree of calcification in CT images. The described computational framework, while is safe and non-invasive, can analyze valve dynamics for finding probable valve calcification locations and hint for further and closer investigations with other methods. It may be emphasized that contrast computed tomography imaging can provide 3-D patterns of calcification on aortic valve leaflets to a degree of specificity that may not be possible with the described Doppler-based computational framework, and as such emphasizes the importance and value of existing calcium scoring methods [54-56, 190].

In addition, the Spearman's correlations presented herein explain the predictability of post-TAVR outcomes from computationally acquired pre-TAVR valve dynamics and global hemodynamics using the described Doppler-based computational framework. For the significant monotonically associated variables in the single-site retrospective sample, the knowledge of the pre-TAVR parameter tells us something in predicting the probability of the post-TAVR parameter. The coefficient of determination ($R^2$) explains the proportion of variability in a post-TAVR parameter accounted for by a pre-TAVR parameter. Specifically, the results highlight the importance of computational acquired global hemodynamics pre-TAVR, such as normalized workload, maximum LV pressure, and systemic arterial compliance in predicting post-TAVR outcomes such as mitral regurgitation, diastolic dysfunction, and clinical measures such as acceleration time and pulse pressure. Moreover, the Spearman's correlations indicate that pre-TAVR valve dynamics (leaflet and cardiac cycle specific displacement, Mises stress, stiffness, and major principal stress) predict changes in post-TAVR clinical outcomes (i.e., diastolic arterial pressure, ejection time, ejection fraction, pulse pressure, acceleration time) and global hemodynamics (stroke volume).

It may be important to note that lack of evidence for an association (i.e., $p>0.05$) should not be considered as no association (evidence for the null hypothesis), but uninformative. Significant associations yield evidence for an association deviating from zero, and not the strength of association or practical/clinical significance. The possibility of potential measurement errors in the medical records and laboratory tests is also acknowledged. In lieu of increasing type II error for these associations, non-corrected results are presented (i.e., no corrections for multiple comparison were done). These comparisons were complementary and consistent with the planned investigation to compare pre- and post-TAVR outcomes. These associations likely increase with age (upward bias) as elder individuals are over-sampled (because of data acquired from a primary care setting). Further, false associations can occur because of the multifaceted nature of aortic stenosis as a common cause between the variables and introduce spurious association, as many unfavorable conditions may be related. Due to the low sample size, adjustment for confounders (e.g., age, sex) could not be performed. Larger samples and further study may help to explain these associations and investigate causality, generality, and identify expectations in which some of these variables do not correlate.

(2) Limitations

Due to the low sample size in the example study, the preliminary and exploratory nature of these data is acknowledged. Future work may include sufficiently powered, multisite collaborative studies to further explore and stabilize these associations. Future studies may consider further validation of the computational framework in a large population of patients with aortic stenosis. In addition, robustness of the method may be further investigated in future studies Example Results—Set 2

As described herein above, the study population included twelve patients with severe AS who underwent TAVR at St. Paul's Hospital (Vancouver, Canada).

Statistics

Statistical analysis was performed using Jamovi v.1.8.0. Continuous variables were expressed as mean±SD or median (interquartile range) as appropriate. Categorical data were presented as number (percentage). Correlations between continuous variables were assessed with Pearson r or Spearman p. Comparisons between pre and post paired continuous variables was performed using Paired Student's or Wilcoxon signed rank tests depending on normality. Statistical significance was considered when the p-value was less than 0.05.

Figure 13A:
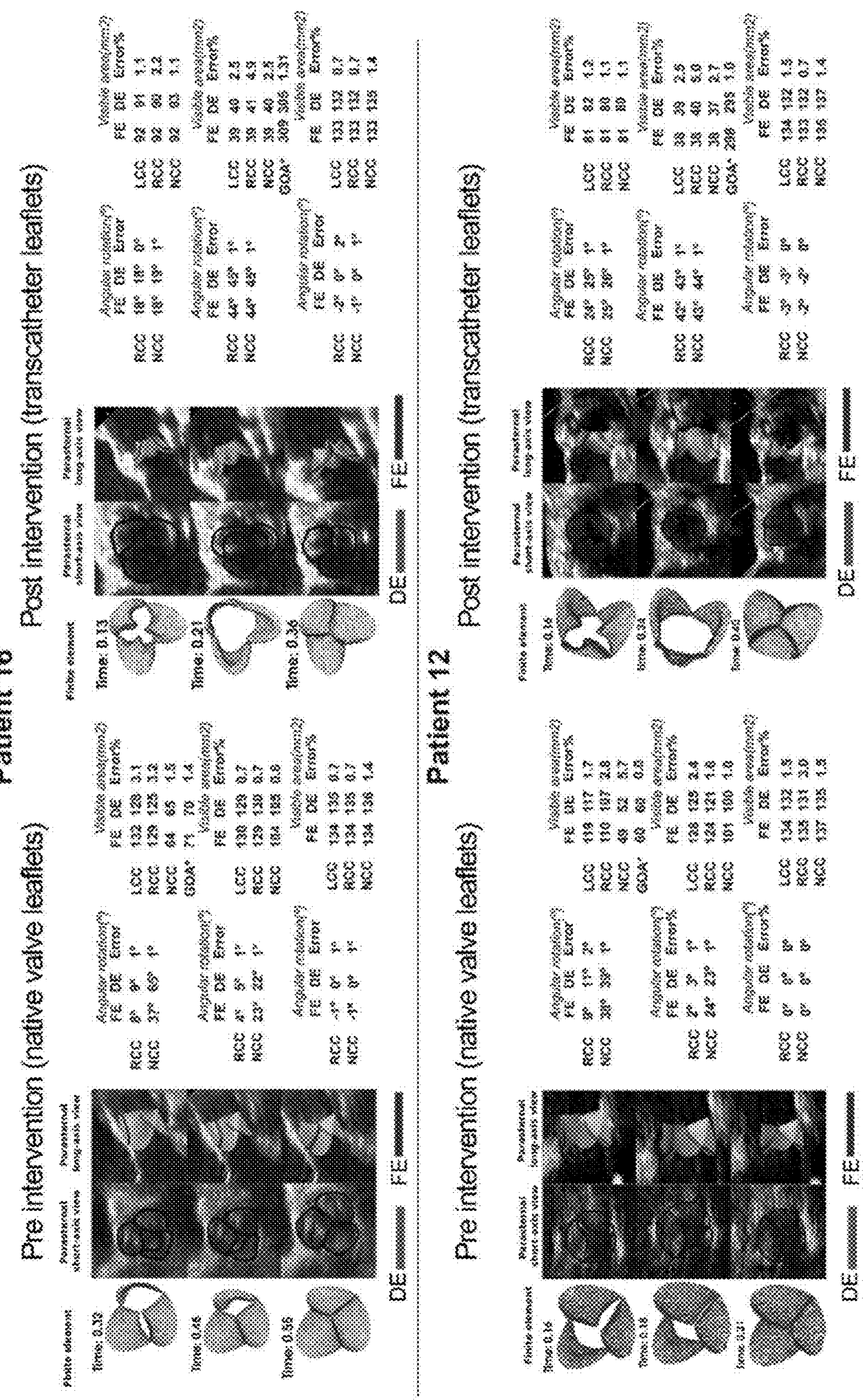

Validation: Non-Invasive Patient-Specific Diagnostic Framework (Doppler-Based Lumped Parameter Algorithm and Doppler-Based 3-D Non-Linear Finite Element Solver) Vs. Clinical Doppler Echocardiography Data Referring now to FIG. 13, shown therein are example validation results of Doppler-based lumped parameter algorithm and Doppler-based 3-D non-linear finite element solver vs. clinical Transesophageal echocardiography echocardiography data in pre-intervention and post-intervention status. The results of the finite element solver and high-quality TEE images have been compared geometrically in different time steps. The figures are shown in three time-steps throughout the cardiac cycle. Angular position was calculated using long axis-parasternal plane view and different visible surface areas were determined in parasternal short-axis plane views. The mentioned quantitative values achieved through TEE are compared to the results of the disclosed doppler-based framework both pre- and post-TAVR for patients #16, #12, #31, and #3.

Angular Rotation

FIG. 4 compares the angular rotation of the right coronary cusp (RCC) with the non-coronary cusp (NCC) using transesophageal echocardiographic data pre- and post-TAVR with the results from the disclosed Doppler-based diagnostic framework (Doppler-based lumped parameter algorithm coupled with finite element solver; FIG. 1) in 4 sample patients (out of 12 AS patients) at three varying time points throughout the cardiac cycle. The measured angular rotation using transesophageal echocardiography correlated well with the simulated results computed by the disclosed Doppler-based diagnostic framework in all patients (N=12) investigated in this example study with angular errors ranging from 0° (minimum) to 2° (maximum) in both pre- and post-TAVR.

Visible Area

The visible area of all three aortic leaflets (LCC, RCC, NCC) is investigated in FIG. 4 based on the results from the disclosed Doppler-based diagnostic framework along with the measurements acquired by transesophageal echocardiography in 4 sample patients at three time points in the cardiac cycle, both pre- and post-TAVR. Based on the results, very strong agreements are shown between the disclosed Doppler-based diagnostic framework and transesophageal echocardiography in all patients (N=12) investigated in this example study with errors ranging from 0-5.7%, however, the majority are under 3.0% error.

Current Clinical Assessment

Figure 26:
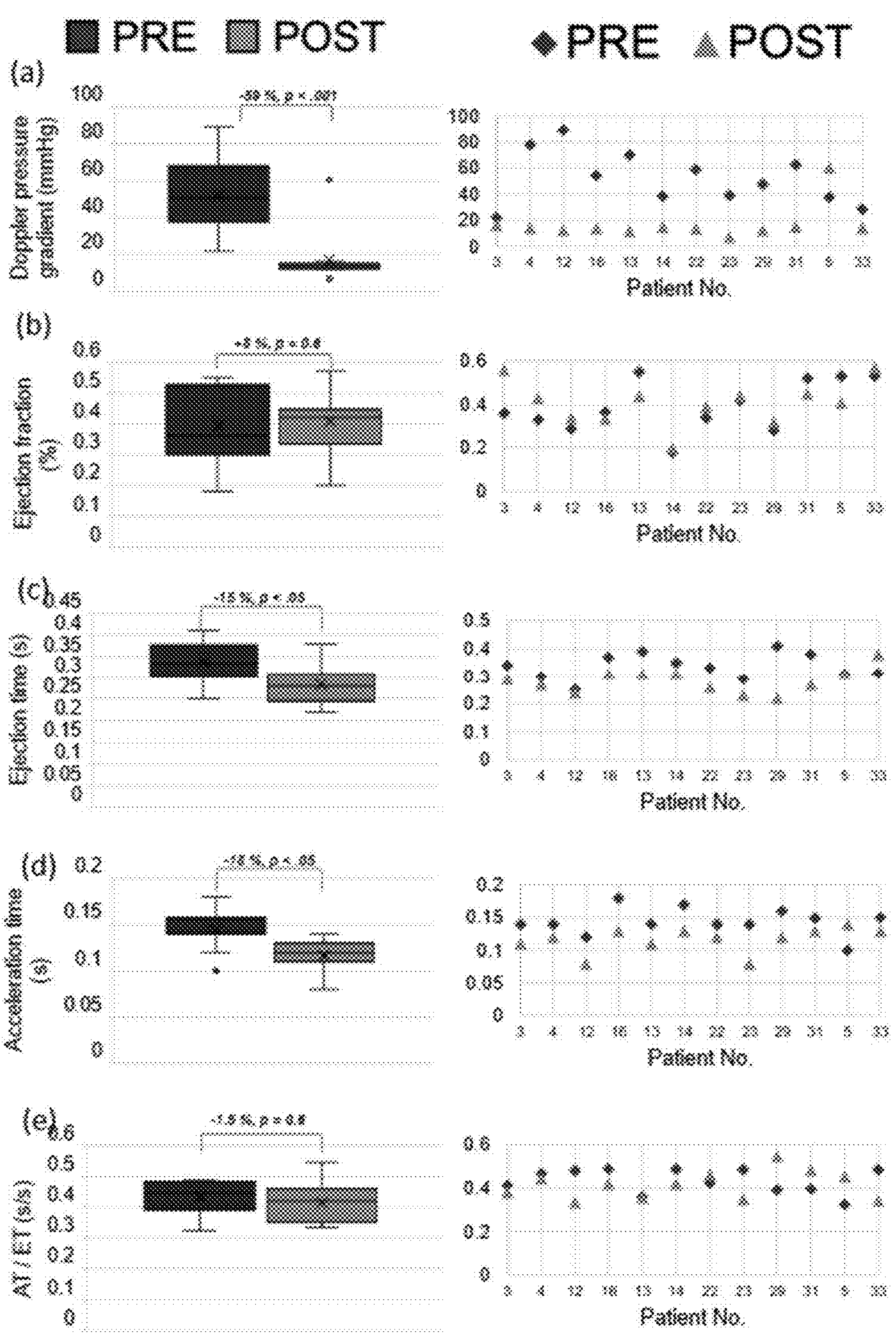
FIG. 26 shows example results of clinical assessment of hemodynamics.

Referring now to FIG. 26, shown therein are example results of clinical assessment of hemodynamics. Changes in clinical assessment of patients' hemodynamics before and 90 days following TAVR (n=12). Column 1 of FIG. 26 shows pre-TAVR and post-TAVR hemodynamic measures (n=12) for—(a) Doppler pressure gradient; (b) Ejection fraction; (c) Ejection time; (d) Acceleration time, (e) AT/ET. Where statistical significance occurs, p-values are indicated between paired variables in the box plot). Column 2 of FIG. 26 shows individual data points (n=12) comparing pre-TAVR and post-TAVR measures for the same variable in column 1.

(1) Doppler Pressure Gradient

Clinical assessment of AS for management and intervention decisions is performed based on the symptoms and hemodynamics metrics that focus locally and only on the aortic valve [39, 43, 155]. Based on the transvalvular pressure gradient, diagnosis and clinical decisions can be made [155]. According to the documented clinical Doppler echocardiography data, TAVR significantly decreased the pressure gradient across the aortic valve (FIG. 26(*a*), 52.2±20.4 vs. 17.3±13.8 [mmHg], p<0.001). Individual data points reveal that, with the exception of Patient #5 whose pressure gradient during systole post-TAVR increased by 59%, all other patient pressure gradients (11 out of the 12 patients (91%)) returned to a normal range (i.e., <25 mmHg; reductions ranged from 25% to 86%).

(2) Ejection Fraction

Ejection fraction (EF), indicative of left ventricle contractility, measures the ability of the LV to pump blood with each heartbeat and is defined as EF=(EDV−ESV)/EDV; where EDV and ESV are end-diastolic volume and end-systolic volume, respectively [47]. Normal EF values reside above 41% for individuals with proper cardiac function [156]. Reduced left ventricular ejection fraction and low aortic valve pressure gradient during systole have been linked to poor long-term outcomes in patients with AS who undergo transcatheter aortic valve replacement [191]. A significant increase in EF post-TAVR (FIG. 26(*b*), 0.39±0.11 vs. 0.41±0.1, p=0.6) was not observed, three of the patients (Patients #5, #31 & #13) showed worsening EF. Patient #5's ejection fraction worsened by 29% post-TAVR (41%), compared to pre-TAVR (53%) while Patient #13's and Patient #31's EFs post-TAVR were within the normal range (i.e., 41%) at 44% and 45%, respectively. Both Patient #13 and #31 experienced a reduction of 25% and 16%, respectively, compared to pre-TAVR values. TAVR did not raise EF values to normal levels for 5 out of 12 patients.

(3) Ejection Time and Acceleration Time

Few studies have considered ejection dynamic parameters such as ejection time (ET), acceleration time (AT) and ET/AT [157, 158, 192, 193]. The ejection time (ET) is the time between the opening and closing of the aortic valve, while the acceleration time (AT) is the time it takes for an aortic valve to open and reach peak aortic jet velocity [157]. The parameters explaining ejection dynamics may be considered diagnostic parameters when there are inconsistencies between the aortic valve area and pressure gradient over the aortic valve during systole, which are used as common standards for evaluating aortic valve severity [158]. For prosthetic valves, acceleration time of greater than 100 ms is abnormal and AT/ET greater than 0.4 is indicative of an obstruction [194]. For native aortic valves, AT>0.094 s and AT/ET>0.35 might indicate severe aortic stenosis [158].

Reference is now made to FIGS. 16, 19, 22, and 25. FIG. 16 shows comparison of doppler-based finite element results with computed tomography; leaflet-specific time-averaged major principal stress; and Doppler-based calibrated material properties for an example patient #3, in accordance with one or more example embodiments. FIG. 16(*a*) shows computed tomographic and doppler echocardiographic images compared to the results of the doppler-based finite element solver; FIG. 16(*b*) shows the time-averaged maximum principal stress on all native aortic valve leaflets pre-intervention and all transcatheter valve leaflets post-intervention; and FIG. 16(*c*) shows results of the doppler-based framework illustrating the material properties and leaflet stiffness as well as performance features such as ejection time and cardiac cycle duration.

FIG. 19 shows comparison of doppler-based finite element results with computed tomography; leaflet-specific time-averaged major principal stress; and Doppler-based calibrated material properties for an example patient #12, in accordance with one or more example embodiments. FIG. 19(*a*) shows computed tomographic and doppler echocardiographic images compared to the results of the doppler-based finite element solver; FIG. 19(*b*) shows the time-averaged maximum principal stress on all native aortic valve leaflets pre-intervention and all transcatheter valve leaflets post-intervention; and FIG. 19(*c*) shows results of the doppler-based framework illustrating the material properties and leaflet stiffness as well as performance features such as ejection time and cardiac cycle duration.

FIG. 22 shows comparison of doppler-based finite element results with computed tomography; leaflet-specific time-averaged major principal stress; and Doppler-based calibrated material properties for an example patient #16, in accordance with one or more example embodiments. FIG. 22(*a*) shows computed tomographic and doppler echocardiographic images compared to the results of the doppler-based finite element solver; FIG. 22(*b*) shows the time-averaged maximum principal stress on all native aortic valve leaflets pre-intervention and all transcatheter valve leaflets post-intervention; and FIG. 22(*c*) shows results of the doppler-based framework illustrating the material properties and leaflet stiffness as well as performance features such as ejection time and cardiac cycle duration.

FIG. 25 shows comparison of doppler-based finite element results with computed tomography; leaflet-specific time-averaged major principal stress; and Doppler-based calibrated material properties for an example patient #31, in accordance with one or more example embodiments. FIG. 25(*a*) shows computed tomographic and doppler echocardiographic images compared to the results of the doppler-based finite element solver; FIG. 25(*b*) shows the time-averaged maximum principal stress on all native aortic valve leaflets pre-intervention and all transcatheter valve leaflets post-intervention; and FIG. 25(*c*) shows results of the doppler-based framework illustrating the material properties and leaflet stiffness as well as performance features such as ejection time and cardiac cycle duration.

FIGS. 16, 19, 22, and 25, panel C illustrate the change in ejection time and total cardiac duration between pre- and post-TAVR for patients #3, #12, #16, and #31, respectively. Patients #3, #16, and #31 exhibited improved ET and total cardiac duration, however, patient #12 exhibited a negligible improvement in ET and worsened cardiac duration post-TAVR. Following TAVR, there was a significant 16% reduction in ejection time (~91% of patients, FIG. 26(*c*), 0.34±0.04 vs. 0.29±0.04 [s], $p<0.05$). Despite this reduction in ejection time, two of the patients (Patients #5 and #12) showed a negligible change in ejection time post-TAVR. In one patient (Patient #33), ejection time worsened (increased by 22%) post-TAVR. Similarly, following TAVR we observed a significant 18% reduction in acceleration time (~91% of patients, FIG. 26(*d*), 0.14±0.02 vs 0.12±0.02 [s], $p<0.05$). However, Patient #5 showed an increase in acceleration time post-TAVR, relative to pre-TAVR. AT/ET did not significantly change following TAVR (FIG. 26(*e*), 0.43±0.06 vs. 0.42±0.06, p=0.6).

(4) Diastolic Dysfunction

The impaired relaxation of the left ventricle is often referred to as diastolic dysfunction [47,195]. In this example study, the diastolic dysfunction was classified from Grade I to III based on the E wave to A wave ratio (E/A) from mitral inflow. In the example group, diastolic dysfunction ranged from grade 1-3 in both pre- and post-intervention cases. The average grade for the 12-patient group increased from 2.25 pre-intervention to 2.42 post-TAVR. The condition for 3 (Patients #5, #22, #23) of the 12 patients worsened whereas only 1 patient (Patient #13) exhibited an improvement in diastolic dysfunction.

(5) Paravalvular Leakage

Paravalvular leakage is common post-operative complication following TAVR, due to imperfect sealing between the stent and the native aortic root. Almost all patients were diagnosed with some degree of PVL following procedure ([6/12] mild, [4/12] moderate and 1 severe).

Global Hemodynamics Computed by Doppler-Based Diagnostic Lumped Parameter Algorithm In patients with aortic stenosis, the healthy instantaneous LV pressure and/or volume are altered which ultimately overloads the heart. Metrics of cardiac function computed by the disclosed Doppler-based lumped parameter algorithm were investigated to determine the effects of TAVR on patient condition (FIG. 1, Panel a). The impacts of the TAVR on the aortic valve pressure gradient were not always accompanied by reduction in LV function parameter, e.g., LV workload, normalized LV workload to stroke volume and maximum LV pressure.

(1) LV Workload

LV workload represents the amount of energy delivered to the blood by the left ventricle in each cardiac cycle, plus the energy required to overcome the left ventricle's viscoelastic qualities, and is an effective metric for determining cardiac function [47]. The ideal LV workload is less than 1 [J] in healthy individuals with proper cardiac function [47,154, 196].

Figure 15:
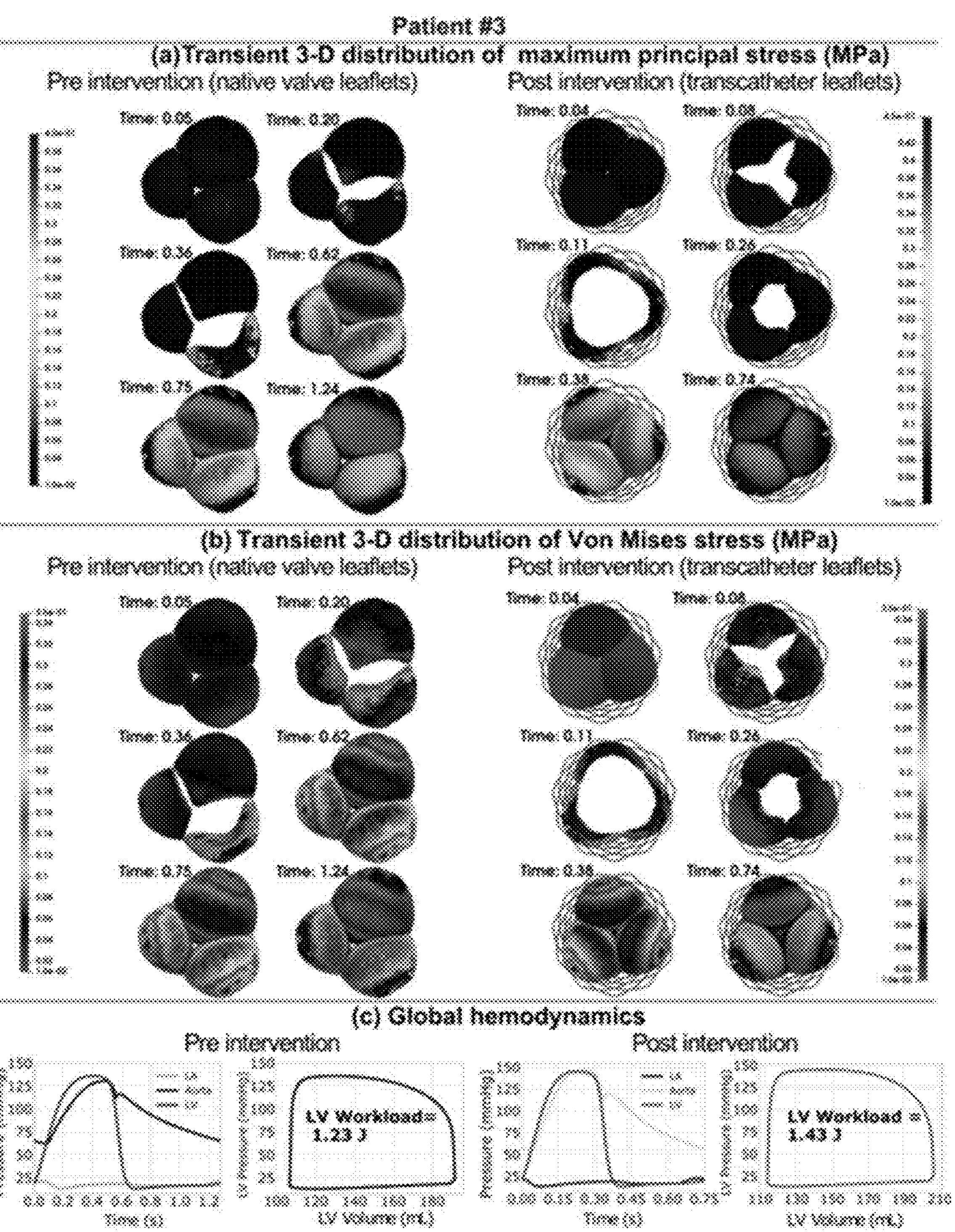
FIG. 15 shows changes in valve dynamics and global hemodynamics between baseline and 90-day post-TAVR for the example patient of FIG. 14.

Reference is now made to FIGS. 15, 18, 21, 24. FIG. 15 shows changes in valve dynamics and global hemodynamics in example patient #3 between baseline and 90-day post-TAVR. FIG. 15(*a*) shows transient distribution of major principal stress over the full cardiac cycle; FIG. 15(*b*) shows transient distribution of the von-mises stress over the full cardiac cycle; and FIG. 15(*c*) shows global hemodynamics: LV workload; aorta and LV pressures in both pre- and post-intervention states. Patient #3: Pre-TAVR: severe aortic stenosis (EOA=0.9 $cm^2$), type 2 diabetes mellitus, coronary artery disease and hypertension, chronic AF, ejection fraction: 36%, brachial pressures: 58 and 132 mmHg; Post-TAVR: aortic valve (EOA=2.0 $cm^2$), hypertension, type 2 diabetes mellitus, coronary artery disease, paravalvular leakage, chronic AF, mild-moderate mitral regurgitation, ejection fraction: 56%, brachial pressures: 55 and 148 mmHg.

FIG. 18 shows changes in valve dynamics and global hemodynamics in example patient #12 between baseline and 90-day post-TAVR. FIG. 18(*a*) shows transient distribution of major principal stress over the full cardiac cycle; FIG. 18(*b*) shows transient distribution of the von-mises stress over the full cardiac cycle; and FIG. 18(*c*) shows global hemodynamics: LV workload; aorta and LV pressures in both pre- and post-intervention states. Patient #12: Pre-TAVR: severe aortic stenosis (EOA=0.6 $cm^2$), dyslipidemia, coronary artery disease, mild to moderate mitral regurgitation and chronic AF, ejection fraction: 29%, brachial pressures: 61 and 107 mmHg; Post-TAVR: aortic valve (EOA=2.0 $cm^2$), mild mitral regurgitation and dyslipidemia, ejection fraction: 34%, brachial pressures: 86 and 130 mmHg.

Figure 21:
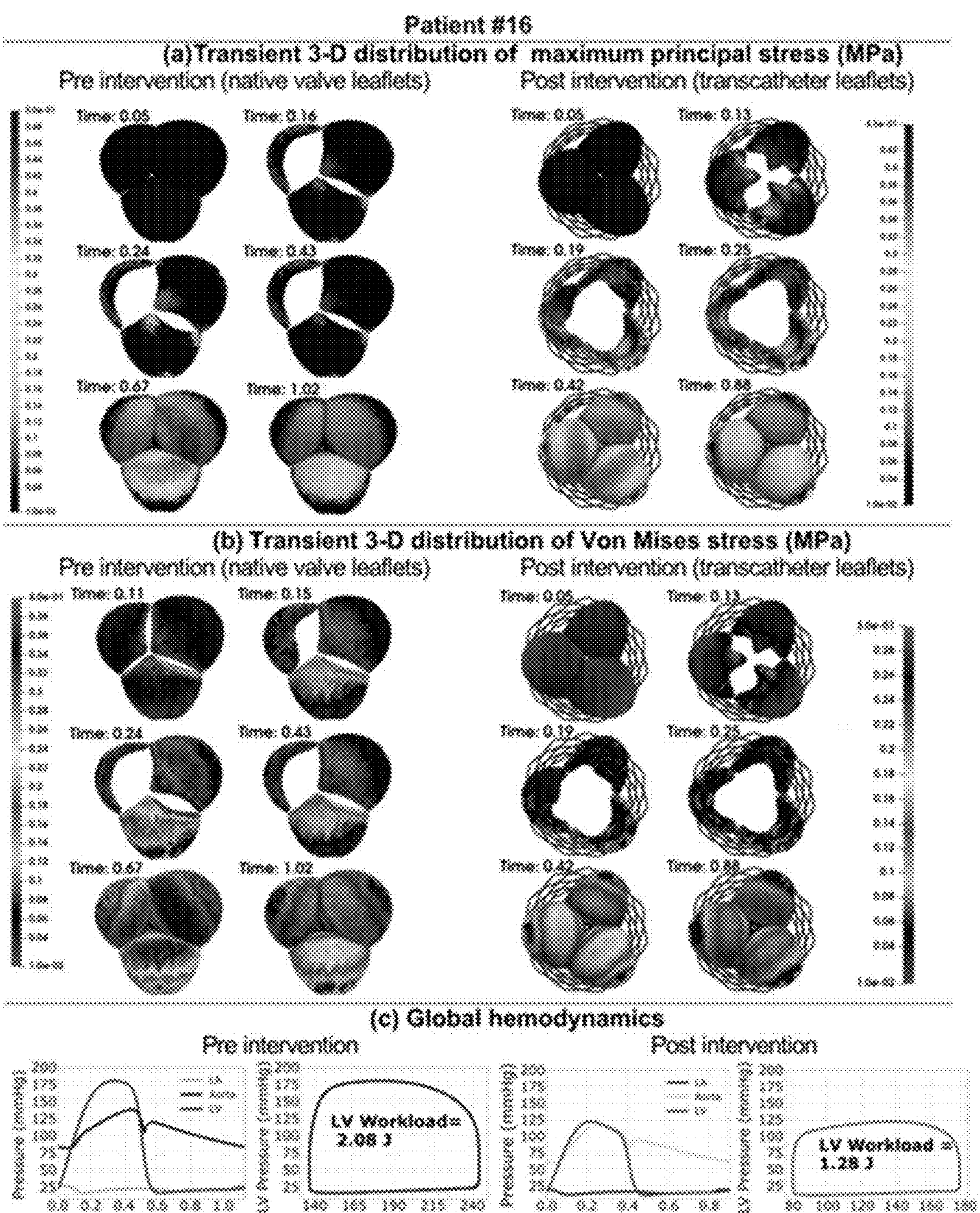
FIG. 21 shows changes in valve dynamics and global hemodynamics between baseline and 90-day post-TAVR for the example patient of FIG. 20.

FIG. 21 shows changes in valve dynamics and global hemodynamics in example patient #16 between baseline and 90-day post-TAVR. FIG. 21(*a*) shows transient distribution of major principal stress over the full cardiac cycle; FIG. 21(*b*) shows transient distribution of the von-mises stress over the full cardiac cycle; and FIG. 21(*c*) shows global hemodynamics: LV workload; aorta and LV pressures in both pre- and post-intervention states. Patient #16: Pre-TAVR: severe aortic stenosis (EOA=0.7 $cm^2$), coronary artery disease and hypertension, mild mitral regurgitation, mild aortic regurgitation, ejection fraction: 10%, brachial pressures: 80 and 140 mmHg; Post-TAVR: aortic valve (EOA=2.0 $cm^2$), mild aortic regurgitation, ejection fraction: 8%, brachial pressures: 61 and 115 mm Hg.

FIG. 24 shows changes in valve dynamics and global hemodynamics in example patient #31 between baseline and 90-day post-TAVR. FIG. 24(*a*) shows transient distribution of major principal stress over the full cardiac cycle; FIG. 24(*b*) shows transient distribution of the von-mises stress over the full cardiac cycle; and FIG. 24(*c*) shows global hemodynamics: LV workload; aorta and LV pressures in both pre- and post-intervention states. Patient #31: Pre-TAVR: severe aortic stenosis (EOA=0.8 $cm^2$), type 2 diabetes mellitus, moderate aortic regurgitation, coronary artery disease and hypertension, ejection fraction: 52%, brachial pressures: 59 and 164 mmHg; Post-TAVR: aortic valve (EOA=2.0 $cm^2$), type 2 diabetes mellitus, ejection fraction: 45%, brachial pressures: 58 and 127 mmHg.

LV workload was calculated as the area encompassed by the LV volume and LV pressure curves (see e.g., FIGS. 15, 18, 21, 24, panel C). TAVR is intended to reduce the LV workload by removing the severe aortic stenosis [6, 39, 43]. As shown in FIGS. 21 and 24, panel C, the LV workload drastically improved from 2.08-1.28 [J] and 2.57-1.26 [J] for patients #16 and #31, respectively. In contrast, FIGS. 15 and 18, panel C show the worsened conditions with respect to LV workload for patients #3 and #12 whose workload increased from 1.23-1.43 [J] and 0.67-0.99 [J], respectively.

Figure 27:
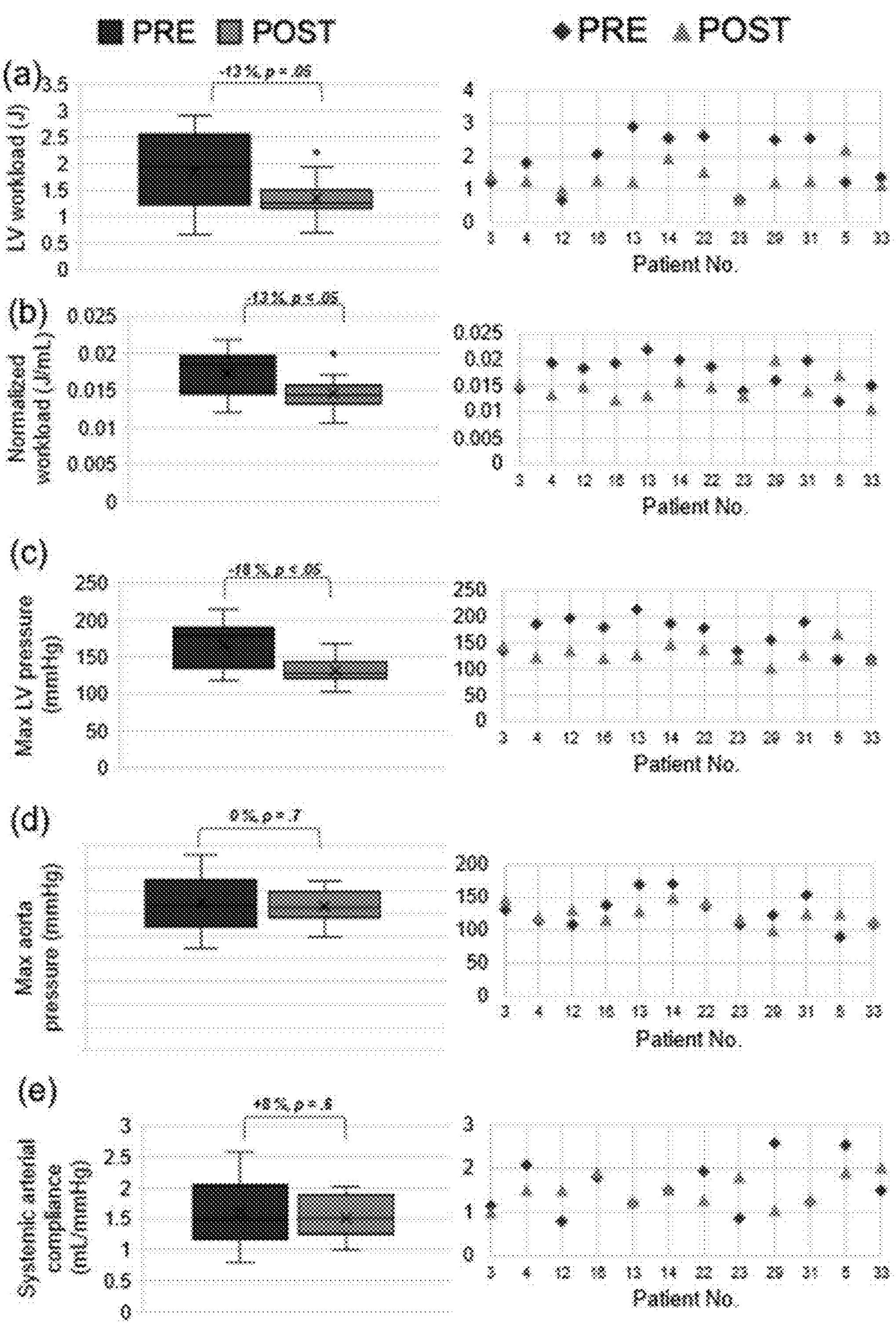
FIG. 27 shows example global hemodynamics data, in accordance with one or more embodiments.

Referring next to FIG. 27, shown therein is example global hemodynamics data, in accordance with one or more embodiments. Changes in predicted global hemodynamics before and 90 days following TAVR (n=12). Column 1 of FIG. 27 shows pre-TAVR and post-TAVR hemodynamic measures (n=12) for—(a) LV Workload; (b) Normalized workload; (c) Maximum left ventricle pressure; (d) Maximum aorta pressure; (e) Systemic arterial compliance. Where statistical significance occurs, p-values are indicated between paired variables in the box plot. Column 2 of FIG. 27 shows individual data points (n=12) comparing pre-TAVR and post-TAVR measures for the same variable in column 1.

The simulation results demonstrated that, despite a group level 13% reduction in LV workload (FIG. 27(*a*), 1.8±0.8 vs. 1.4±0.4 [J], p=0.05), only 8 of the 12 patients (~58%) had a reduction in LV workload post-TAVR. In four patients (Patients #3, #5, #12, #23) LV workload was not significantly reduced (improved) post-TAVR (<5% reduction). In one patient (Patient #5), LV workload increased (worsened) by 54% post-TAVR.

(2) Normalized LV Workload

Normalized LV workload to stroke volume is the energy required to eject 1 ml of blood through the valvular-arterial system [47,150]. A significant 13% reduction was observed in normalized LV workload post-TAVR; as 9 out of the 12 patients (75%) showed an improvement in normalized LV workload post TAVR (FIG. 27(*b*), 0.017±0.003 vs. 0.015±0.002 [J/mL], p<0.05). However, 3 patients (#3, #29 & #5) exhibited an increased normalized workload post-procedurally.

(3) LV Pressure

LV pressure is an important metric to measure and monitor when analyzing cardiac function as LV pressure overload can result in various cardiac diseases such as LV hypertrophy and failure. Maximum LV pressure observed in healthy individuals with proper cardiac function is below 120 [mmHg] [160]. FIGS. 15, 18, 21, and 24, panel C, show the LV pressure over the course of the cardiac cycle and have peaks of 136 [mmHg], 197 [mmHg], 179.8 [mmHg], and 190 [mmHg] pre-TAVR for patients #3, #12, #16, and #31, respectively. Post-TAVR, the maximum LV pressure observed in these patients were 144.96 [mmHg], 135.5 [mmHg], 121.7 [mmHg], and 127.76 [mmHg], respectively. It is evident through these results that the maximum LV pressure for patients #12, #16, and #31 significantly improved, however, Patient #3 had a worsened condition post-TAVR. Although, 9 of the 12 patients had a significant 18% reduction in maximum LV pressure and there was an overall group-level decrease (FIG. 27(*c*), 166.4±32.2 vs 131.4±16.9 [mmHg]) post-TAVR, Patient #33 showed a negligible difference (<1%), while Patient #3 and Patient #5 had an increase in LV pressure (an increase of 6.6% and 42%, respectively). Despite the group level improvements in maximum LV pressure, only 5 of the 12 patients (41%) had a decrease in maximum aortic pressure (FIG. 18*d*).

(4) Systemic Arterial Compliance

Arterial stiffening reduces the compliance of the systemic arterial system and is commonly linked to the development and progression of vascular and ventricular diseases [161]. Systemic arterial compliance (SAC=stroke volume index/pulse pressure) is an effective metric indicative of arterial hemodynamics and is inversely related to aortic stenosis morbidity risk [162], where higher risk is correlated with a lower SAC value (less than 0.64 ml/m$^2$/mmHg). There were minimal group-level changes in SAC following TAVR (FIG. 27(*e*), 0.80±0.30 vs. 0.75±0.17 [ml/m$^2$/mmHg], p=0.6). While 7 of the 12 patients had a SAC value above 0.64 ml/m$^2$/mmHg pre-TAVR, the simulation predicted that only 5 (patients #4, #12, #16, #23, #31) of the 12 patients would have had an improved SAC post-TAVR and 3 patients would have a negligible change (patients #13, #14, #31). The simulated change in SAC between pre- and post-TAVR states across all patients ranged from −59% (Patient #29) to +108% (Patient #23).

Valve Dynamics Computed by Non-Invasive Diagnostic Framework (Doppler-Based Lumped Parameter Algorithm and Doppler-Based 3-D Non-Linear Finite Element Solver)

Aortic valve tissues experience time-dependent stress and displacement distributions as a result of transient loads. It is well known that stress can be a trigger for calcification and inflammation of native aortic valve tissues, and they can also cause failure and degeneration of transcatheter leaflets intensified by the immune system response and cyclic loadings [197]. Even though transcatheter leaflets are shown to have better compatibility with the immune and circulatory system, there is a remaining issue with their longevity which is far less than classical bioprosthetic valves [198]. Biomechanical factors resulting from hemodynamic loads are a common dominator of a variety of vascular diseases. Various mechanical metrics including 3-D Mises stress (the derivative format of principle stress), 3-D major principal stress (the maximum value of the three principal stresses), as well as displacement magnitude resulted from the disclosed Doppler-based computational framework (Doppler-based lumped parameter algorithm coupled with Doppler-based 3-D non-linear finite element solver; FIG. 1) are described as follows:

(1) 3-D Mises Stress

Mises stress refers to the derivative form of principal stress [199, 200]. Reference is next made to FIGS. 14, 17, 20, and 23. FIG. 14 shows 3D motion and 3D distribution contours of Mises stress in example patient #3 at six time points throughout the cardiac cycle in both pre- and post-intervention states, in accordance with one or more embodiments. Using the disclosed framework, 3D deformation of aortic valve leaflet during full cardiac cycle as well as the Von Mises stress distribution were estimated. The regions covered with white points are representing the calcified areas visualized manually by using multi-slice CT images.

FIG. 17 shows 3D motion and 3D distribution contours of Mises stress in example patient #12 at six time points throughout the cardiac cycle in both pre- and post-intervention states, in accordance with one or more embodiments. Using the disclosed framework, 3D deformation of aortic valve leaflet during full cardiac cycle as well as the Von Mises stress distribution were estimated.

Figure 20:
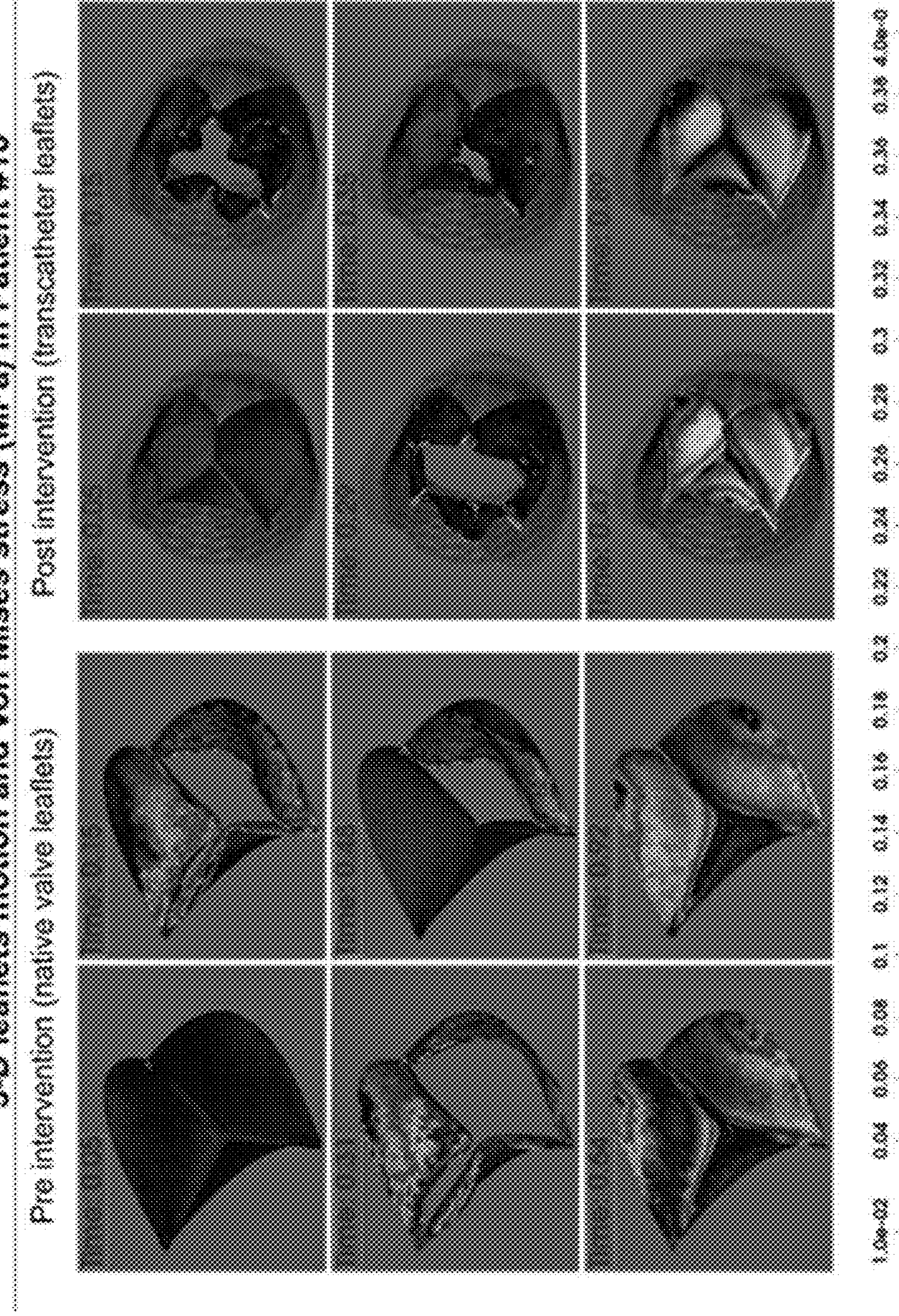
FIG. 20 shows 3D motion and 3D distribution contours of Mises stress in another example patient at six time points throughout the cardiac cycle in both pre- and post-intervention states, in accordance with one or more embodiments.

FIG. 20 shows 3D motion and 3D distribution contours of Mises stress in example patient #16 at six time points throughout the cardiac cycle in both pre- and post-intervention states, in accordance with one or more embodiments. Using the disclosed framework, 3D deformation of aortic valve leaflet during full cardiac cycle as well as the Von Mises stress distribution were estimated.

FIG. 23 shows 3D motion and 3D distribution contours of Mises stress in example patient #31 at six time points throughout the cardiac cycle in both pre- and post-intervention states, in accordance with one or more embodiments. Using the disclosed framework, 3D deformation of aortic valve leaflet during full cardiac cycle as well as the Von Mises stress distribution were estimated. The regions covered with white points are representing the calcified areas visualized manually by using multi-slice CT images.

FIGS. 14, 17, 20, and 23 illustrate the 3-D motion of the valve throughout the entire cardiac cycle while displaying von-mises stress across all leaflets in both pre- and post-TAVR. FIGS. 15, 18, 21, and 24, panel A, show the transient 3-D distribution of Mises stress over the aortic valve leaflets throughout the entire cardiac cycle for patients #3, #12, #16, and #31, respectively, in both pre- and post-TAVR states. Patient #3 (FIG. 15(*b*)) displayed elevated Mises stress over the aortic valve specifically at the start of diastole when the valve is first closed, in both pre- and post-TAVR states. Patients #12, #16, and #31 all exhibited similar Mises stress contours as there were elevated levels at both peak systole (open valve) and peak diastole (closed valve) pre-TAVR, however, post-TAVR Mises stress contours displayed elevated levels solely in diastole (closed valve). The mean mises stress for all sample patients, with the exception of Patient #12, improved following the TAVR procedure.

Figure 28:
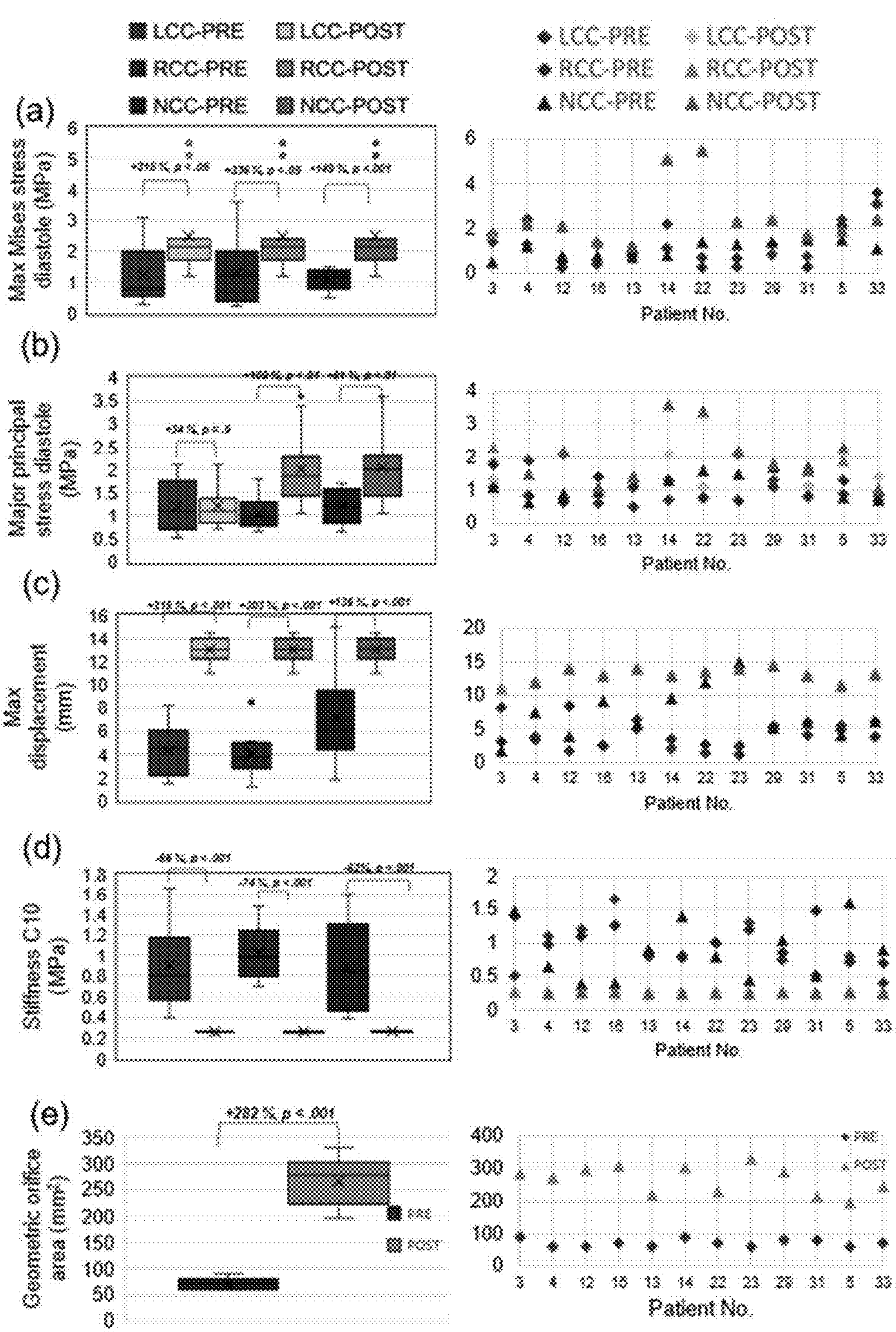
FIG. 28 shows example valve dynamics data, in accordance with one or more embodiments.

Referring next to FIG. 28, shown therein is example valve dynamics data, in accordance with one or more embodiments. FIG. 28 shows changes in patients' predicted valve dynamics before and 90 days following TAVR during the full cardiac cycle. Column 1 of FIG. 28 shows pre-TAVR and Post-TAVR hemodynamic measures (n=12) for—(a) Maximum Mises stress at diastole; (b) Major principal stress at diastole; (c) Maximum displacement; (d) Stiffness; and (e) Geometric orifice area. Where statistical significance occurs, p-values are indicated p-values are indicated between paired variables in the box plot for each leaflet. Column 2 of FIG. 28 shows individual data points (n=12) comparing pre-TAVR and post-TAVR measures for the same variable in that column as Column 1.

Post-TAVR, there was a significant 1 to 3-fold increase for each leaflet in group level maximum Mises stress (at diastole; FIG. 28(*a*)).

(2) 3-D Major Principal Stress

As previously mentioned, it is hypothesized that abnormal stresses are a driving force behind the development of calcification and progression of aortic stenosis [7, 17, 24, 26, 35]. Stress components have different values depending on the desired coordinate system. When the area elements are considered such that the shear stress is eliminated, each element is solely loaded by normal stresses, known as principal stresses, which includes major principal stress, median principal stress, and minor principal stress [33, 107]. In the example study, the major principal stress was focused on, which is the maximum of the three principal stress components. FIGS. 16, 19, 22, and 25, panel B, illustrate the specific regions of time-averaged (over the full cardiac cycle) major principal stress of the individual leaflets in pre- and post-TAVR for patients #3, #12, #16, and #31, respectively. Overall, the major principal stress increased significantly post TAVR particularly for leaflets near the right and non-coronary cusps by (100%, p<0.01) and (81%, p<0.01) respectively (FIG. 28(*b*)).

(3) Displacement Magnitude

In contrast to stress, which has long-term consequences, aortic valve tissue displacement could be a useful tool for monitoring aortic valve movements. Displacement is a vector that depicts the various components of each point's movement on the computational domain (leaflets of aortic valves) and could be a powerful tool for monitoring aortic valve movements [169]. All four sample patients showed a significant improvement in leaflet mobility as all leaflets increased in maximum displacement. The mean maximum displacement across all leaflets increased from 4.37 [mm] to 11.0 [mm], 4.77 [mm] to 14.0 [mm], 4.77 [mm] to 13.0 [mm], and 5.37 [mm] to 13.0 [mm] in patients #3, #12, #16, and #31, respectively. The results from the disclosed Doppler-based framework showed the maximum displacement (in the full cardiac cycle) increased for all leaflets by up to 3 times for leaflets near the left and right coronaries and by almost 1.36 times for the leaflet near the non-coronary cusp following TAVR on a group level basis (FIG. 28(*c*), [4.3±2.1, 4±1.7, 7±3.6] vs [13±0.1.02, 13±1.03, 13±1.03], p<0.001).

Patient-Specific Doppler-Based Material Properties of the Valve Leaflets

The stiffness or mechanical material properties of aortic valve leaflets describe the relationship between the displacement vector and stress tensor. Aortic stenosis is a condition in which the leaflets stiffen, resulting in less opening during ejection time. The TAVR procedure involves replacing stiff native aortic valve leaflets with prosthetic leaflets that have improved elasticity. The disclosed framework can provide the dynamic behaviour of aortic valve leaflets in addition to the asymmetric material properties of leaflets. Leaflet stiffness is illustrated in FIGS. 16, 19, 22, and 25, panel C, which shows the patient-specific material properties for patients #3, #12, #16, and #31, respectively. Parameter $C_{10}$ was used to evaluate leaflet stiffness which was evaluated for all aortic valve leaflets and represents the isotropic portion of the energy density function (equation 4). Increased $C_{10}$ values represent an increased resistance of the leaflets to open when the left ventricle pressure exceeds the aorta pressure during systole [171, 172]. Doppler images were used to calibrate each leaflet separately in the disclosed framework resulting in a specific $C_{10}$ parameter for each leaflet. Pre-TAVR leaflet stiffness ranged from 0.51-1.48 [MPa] with a mean of 1.31 [MPa] for Patient #3 (FIG. 16(*c*)) which significantly reduced to range between 0.26-0.27 [MPa]. Similar results were observed for Patient #12 (FIG. 19(*c*)), pre-TAVR simulated results computed a range of 0.39-1.2 [MPa] with a mean of 0.90 [MPa] which improved to a range of 0.26-0.27 [MPa] across all leaflets. Furthermore, Patient #16 (FIG. 22(*c*)) experienced a leaflet stiffness reduction from 0.4-1.66 [MPa] with a mean of 1.11 [MPa] pre-TAVR, to a range of 0.26-0.27 [MPa] post-TAVR. Finally, stiffness values of 0.51-1.48 [MPa] with a mean of 0.83 [MPa] were computed pre-TAVR for Patient #31 (FIG. 25(*c*)), which significantly decreased to 0.25-0.26 [MPa] across all leaflets post-TAVR. Moreover, on a group level basis, average stiffness among leaflets were calculated to be 0.90±0.37 [MPa] (LCC), 1.03±0.26 [MPa](RCC), and 0.88±0.43 [MPa] (NCC), pre-TAVR, and reduced to 0.26±0.005 [MPa] (LCC), 0.26±0.006 [MPa] (RCC), and 0.26±0.008 [MPa] (NCC), post-TAVR. For all patients, as shown in FIG. 28(*d*), stiffness among all leaflets was significantly reduced following TAVR, with 66, 74 and 52% mean reduction for each leaflet respectively. Subsequently, this relates to an almost 3-fold increase in geometric orifice area (FIG. 28(*e*), 70.8±11.6 vs 266±43.8 [$mm^2$], p<0.001), and reduced the pressure gradient across the aortic valve (FIG. 26(*a*)). The open area between leaflets is known as the geometric orifice area (GOA) [170]. While effective orifice area (EOA) is a flow parameter, GOA which represents the available area for blood flow, which is slightly larger than EOA and is expected to increase post-TAVR [201].

Aortic Valve Calcification

Aortic valve calcification is the most common cause of aortic stenosis [23, 202, 203]. Calcification evaluation and quantification can be used as a tool for diagnosis and monitoring of aortic valve disease [56, 204]. The success of valvular intervention, such as TAVR, is strongly influenced by the presence of asymmetric calcification patterns [54]. Doppler echocardiography is limited in its use for calcification analysis, however, contrast CT imaging is a more powerful tool when evaluating calcium deposits [35, 52, 55]. The disclosed Doppler-based lumped parameter algorithm coupled with a finite element solver can accurately quantify the stiffness and material properties of aortic valve leaflets. Despite the limitations of doppler-echocardiography when analyzing calcification, the disclosed framework has shown a strong relationship between the stiffness measured with calcification of the valve. For instance, the more calcification present on the valve, the stiffer it will be. FIGS. 16, 19, 22, and 25, panel A, show the calcification as obtained from CT images which show a strong correspondence with the stiffness of the leaflets in FIGS. 16, 19, 22, and 25, panel C, respectively. As shown in these figures, the new prosthetic valve structure mimics the healthy non-calcified native valve and we therefore greatly decreased stiffness levels after device implantation is observed.

Discussion

As an emerging alternative treatment strategy to surgery in patients with AS, transcatheter aortic valve replacement possesses several benefits, as well as risks [6]. The optimal function of the aortic valve is heavily influenced by the interaction between the blood flow and the structural properties of the valve [17, 89]. Indeed, abnormal valve dynamics and abnormal hemodynamics are associated with adverse outcomes and must be quantified accurately to allow for accurate risk analysis and to potentially improve patient outcomes [32].

Although medical imaging has made remarkable advancements and possess several benefits, however, none of these tools can quantify valve dynamics and (local and global) hemodynamics [43, 205]. (1) Doppler echocardiography (DE): DE provides functional, real-time information regarding cardiac geometry, instantaneous flow and pressure gradient [206]. DE cannot evaluate local hemodynamics precisely and cannot measure global hemodynamics and valve dynamics [207]; (2) Phase-contrast magnetic resonance imaging (MRI): MRI can provide local hemodynamics. However, MRI cannot measure any global hemodynamic and valve dynamics parameters and its use is limited in patients with implanted medical devices as they remain a major risk during the examination [143, 188]; (3) Computed tomography (CT): Cardiac CT can evaluate valve calcification leaflet-specifically [208]. CT cannot measure any (local and global) hemodynamic parameters and cannot measure valve dynamics. Such information has a high clinical importance for planning advanced treatments for patients with AS and TAVR.

A Doppler-based computational-mechanics framework (Doppler-based patient-specific lumped parameter algorithm, 3-D non-linear finite element solver and 3-D Doppler-based geometry reconstruction) is provided herein that can function as a diagnostic and monitoring tool for patients with AS in both pre and post intervention states at no risk to the patient. The following insights are provided herein:

(1) Doppler Echocardiography Pressure Gradient is a Poor Indicator of Aortic Valve Severity Clinical assessment of AS for management and intervention decisions is performed based on the symptoms and hemodynamics metrics that focus locally and only on the aortic valve [39, 43, 155]. Based on the transvalvular pressure gradient, diagnosis and clinical decisions can be made [155]. According to the documented clinical Doppler echocardiography data, TAVR universally and significantly decreased the pressure gradient across the aortic valve. However, it is critically notable that reductions in transvalvular pressure gradient were not always accompanied by improvements in: (1) clinical metrics such as ejection fraction, ejection time, acceleration time and diastolic dysfunction classification; (2) LV hemodynamics metrics such LV workload, normalized LV workload and maximum LV pressure; (3) valve dynamics such as stress, distensibility and stiffness.

(2) TAVR does not Always Improve Cardiac Function Metrics

Some patients, who underwent TAVR, experienced a significant improvement in terms of pronounced reverse LV remodeling and less congestive heart failure symptoms. However, the situation in some other patients worsened. In patients with aortic stenosis, the healthy instantaneous LV pressure and/or volume are altered which ultimately overloads the heart. Metrics of cardiac function computed by the disclosed Doppler-based lumped parameter algorithm were investigated to determine the effects of TAVR on patient condition. The impacts of the TAVR on the aortic valve pressure gradient were not always associated with reduction in LV function parameters, e.g., LV workload, normalized LV workload to stroke volume and maximum LV pressure. LV hemodynamics metrics worsened in some patients, and they were not significantly improved in the others. Furthermore, the presence of PVL particularly at the moderate and severe category may explain the reduction in EF in some cases and the increase in LV loads following procedure. Indeed, the global hemodynamic metrics could have a prognostic value for predicting and optimizing procedural outcomes and clinical decision support for managing patients post procedurally.

(3) TAVR does not Always Improve Valve Dynamics Metrics

Aortic valve tissues experience time-dependent stress and displacement distributions as a result of transient loads. It is well known that stress can be a trigger for calcification and inflammation of native aortic valve tissues, and they can also cause failure and degeneration of transcatheter leaflets intensified by the immune system response and cyclic loadings [197]. Even though transcatheter leaflets are shown to have better compatibility with the immune and circulatory system, there is a remaining issue with their longevity which is far less than classical bioprosthetic valves [198]. Biomechanical factors resulting from hemodynamic loads are a common dominator of a variety of vascular diseases. Various mechanical metrics including 3-D Mises stress (the derivative format of principle stress), 3-D major principal stress (the maximum value of the three principal stresses), as well as displacement magnitude resulted from the disclosed Doppler-based computational framework. Interestingly the described early investigation implies that despite a marked improvement in the systolic function of the valve through improved leaflet mobility and increase in geometric orifice area, diastolic stresses post TAVR elevated drastically. Indeed, biomechanical forces are the driving force behind the degeneration and failure of prosthetic heart valves and can be measured through the disclosed non-invasive framework, which could indicate deterioration of the replacement valve [31].

(4) Aortic Valve Calcification

Persistent monitoring and early diagnosis of aortic valve stenosis is key in the prevention and proper treatment planning for patients [173]. As the most common cause of AS, calcification in cardiovascular pathologies is commonly associated with adverse outcomes [23, 202, 203]. Aortic valve calcification scoring can be used as a diagnostic method to confirm disease severity as well as for intervention planning and prediction [56, 204]. As a result, understanding the material properties and asymmetric physical features of native aortic valve leaflets can heavily influence and benefit clinical decision-making and surgical planning. Doppler echocardiography is limited in its applicability for analyzing calcification and cannot quantify valve calcification. However, CT calcification scoring is only indicated for patients with discordant echocardiographic diagnosis [55, 155] and even then the bulk CT score cannot directly describe valve biomechanics [55]. Therefore, using the disclosed non-invasive Doppler-based computational framework, the stiffness and material properties for patients for whom CT is not indicated can be quantified. This may have important clinical impacts regarding severe and non-severe calcific aortic stenosis and therefore a reclassification criterion for optimal intervention time [209].

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

[1] Amato, M. C. M., Moffa, P. J., Werner, K. E., Ramires, J. a. F., 2001. Treatment decision in asymptomatic aortic valve stenosis: role of exercise testing. Heart 86, 381-386. https://doi.org/10.1136/heart.86.4.381.

[2] Eveborn, G. W., Schirmer, H., Heggelund, G., Lunde, P., Rasmussen, K., 2013. The evolving epidemiology of valvular aortic stenosis. The Tromsø Study. Heart 99, 396-400. https://doi.org/10.1136/heartjnl-2012-302265.

[3] Carabello, B. A., Paulus, W. J., 2009. Aortic stenosis. The Lancet 373, 956-966. https://doi.org/10.1016/SO140-6736(09)60211-7.

[4] Malouf, J. F., Enriquez-Sarano, M., Pellikka, P. A., Oh, J. K., Bailey, K. R., Chandrasekaran, K., Mullany, C. J., Tajik, A. J., 2002. Severe pulmonary hypertension in patients with severe aortic valve stenosis: clinical profile and prognostic implications. J. Am. Coll. Cardiol. 40, 789-795. https://doi.org/10.1016/SO735-1097(02)02002-8.

[5] Otto, C. M., 2006. Valvular Aortic Stenosis: Disease Severity and Timing of Intervention. J. Am. Coll. Cardiol. 47, 2141-2151. https://doi.org/10.1016/j.jacc.2006.03.002.

[6] Keshavarz-Motamed Zahra, Khodaei Seyedvahid, Rikhtegar Nezami Farhad, Amrute Junedh M., Lee Suk Joon, Brown Jonathan, et al. Mixed Valvular Disease Following Transcatheter Aortic Valve Replacement: Quantification and Systematic Differentiation Using Clinical Measurements and Image-Based Patient-Specific In Silico Modeling. Journal of the American Heart Association 2020; 9:e015063. https://doi.org/10.1161/JAHA.119.015063.

[7] Abbasi M, Azadani A N. Leaflet stress and strain distributions following incomplete transcatheter aortic valve expansion. Journal of Biomechanics 2015; 48:3663-71. https://doi.org/10.1016/j.jbiomech.2015.08.012.

[8] Adams D H, Popma J J, Reardon M J, Yakubov S J, Coselli J S, Deeb G M, et al. Transcatheter Aortic-Valve Replacement with a Self-Expanding Prosthesis. Http://DxDoiOrg/101056/NEJMoa1400590 2014. https://doi.org/10.1056/NEJMoa1400590.

[9] Reardon M J, Van Mieghem N M, Popma J J, Kleiman N S, Søndergaard L, Mumtaz M, et al. Surgical or Transcatheter Aortic-Valve Replacement in Intermediate-Risk Patients. New England Journal of Medicine 2017; 376:1321-31. https://doi.org/10.1056/NEJMoa1700456.

[10] Leon M B, Smith C R, Mack M, Miller D C, Moses J W, Svensson L G, et al. Transcatheter Aortic-Valve Implantation for Aortic Stenosis in Patients Who Cannot Undergo Surgery. New England Journal of Medicine 2010; 363:1597-607. https://doi.org/10.1056/NEJMoa1008232.

[11] Bach David S., Siao Derrick, Girard Steven E., Duvernoy Claire, McCallister Benjamin D., Gualano Sarah K. Evaluation of Patients With Severe Symptomatic Aortic Stenosis Who Do Not Undergo Aortic Valve Replacement. Circulation: Cardiovascular Quality and Outcomes 2009; 2:533-9. https://doi.org/10.1161/CIRCOUTCOMES.109.848259.

[12] Varadarajan P, Kapoor N, Bansal R C, Pai R G. Clinical Profile and Natural History of 453 Nonsurgically Managed Patients With Severe Aortic Stenosis. The Annals of Thoracic Surgery 2006; 82:2111-5. https://doi.org/10.1016/j.athoracsur.2006.07.048.

[13] Ong G, Annabi M-S, Clavel M-A, Guzzetti E, Salaun E, Toubal O, et al. Paravalvular Regurgitation After Transcatheter Aortic Valve Replacement. Interventional Cardiology Clinics 2018; 7:445-58. https://doi.org/10.1016/j.iccl.2018.06.005.

[14] Pibarot P. Paravalvular Regurgitation Following Transcatheter Aortic Valve Replacement: Is it Still an Issue in 2018? Structural Heart 2019; 3:31-3. https://doi.org/10.1080/24748706.2018.1547467.

[15] Sannino A, Stoler R C, Vallabhan R, Potluri S, Pollock B, Filardo G, et al. Assessment of the Severity of Paravalvular Regurgitation and its Role on Survival After Transcatheter Aortic Valve Replacement. Structural Heart 2019; 3:24-30. https://doi.org/10.1080/24748706.2018.1547466.

[16] Ben-Assa E, Biner S, Banai S, Arbel Y, Laufer-Perl M, Kramarz J, et al. Clinical impact of post procedural mitral regurgitation after transcatheter aortic valve replacement. International Journal of Cardiology 2020; 299:215-21. https://doi.org/10.1016/j.ijcard.2019.07.092.

[17] Balachandran K, Sucosky P, Yoganathan A P. Hemodynamics and Mechanobiology of Aortic Valve Inflammation and Calcification. International Journal of Inflammation 2011; 2011:e263870. https://doi.org/10.4061/2011/263870.

[18] Luraghi G, Wu W, De Gaetano F, Rodriguez Matas J F, Moggridge G D, Serrani M, et al. Evaluation of an aortic valve prosthesis: Fluid-structure interaction or structural simulation? Journal of Biomechanics 2017; 58:45-51. https://doi.org/10.1016/j.jbiomech.2017.04.004.

[19] Carmody C J, Burriesci G, Howard I C, Patterson E A. An approach to the simulation of fluid-structure interaction in the aortic valve. Journal of Biomechanics 2006; 39:158-69. https://doi.org/10.1016/j.jbiomech.2004.10.038.

[20] Taraballi F, Sushnitha M, Tsao C, Bauza G, Liverani C, Shi A, et al. Biomimetic Tissue Engineering: Tuning the Immune and Inflammatory Response to Implantable Biomaterials. Advanced Healthcare Materials 2018; 7:1800490. https://doi.org/10.1002/adhm.201800490.

[21] Ge L, Sotiropoulos F. Direction and Magnitude of Blood Flow Shear Stresses on the Leaflets of Aortic Valves: Is There a Link With Valve Calcification? Journal of Biomechanical Engineering 2009; 132:014505. https://doi.org/10.1115/1.4000162.

[22] Otto Catherine M., Burwash Ian G., Legget Malcolm E., Munt Brad I., Fujioka Michelle, Healy Nancy L., et al. Prospective Study of Asymptomatic Valvular Aortic Stenosis. Circulation 1997; 95:2262-70. https://doi.org/10.1161/01.CIR.95.9.2262.

[23] Carabello B A, Paulus W J. Aortic stenosis. The Lancet 2009; 373:956-66. https://doi.org/10.1016/S0140-6736(09)60211-7.

[24] Fisher C I, Chen J, Merryman W D. Calcific nodule morphogenesis by heart valve interstitial cells is strain dependent. Biomech Model Mechanobiol 2013; 12:5-17. https://doi.org/10.1007/s10237-012-0377-8.

[25] Hsu J J, Lim J, Tintut Y, Demer L L. Cell-matrix mechanics and pattern formation in inflammatory cardiovascular calcification. Heart 2016; 102:1710-5. https://doi.org/10.1136/heartjnl-2016-309667.

[26] Hutcheson J D, Venkataraman R, Baudenbacher F J, David Merryman W. Intracellular Ca2+ accumulation is strain-dependent and correlates with apoptosis in aortic valve fibroblasts. Journal of Biomechanics 2012; 45:888-94. https://doi.org/10.1016/j.jbiomech.2011.11.031.

[27] Pawade T A, Newby D E, Dweck M R. Calcification in Aortic Stenosis: The Skeleton Key. Journal of the American College of Cardiology 2015; 66:561-77. https://doi.org/10.1016/j.jacc.2015.05.066.

[28] Corden J, David T, Fisher J. In Vitro Determination of the Curvatures and Bending Strains Acting on the Leaflets of Polyurethane Trileaflet Heart Valves During Leaflet Motion. Proc Inst Mech Eng H 1995; 209:243-53. https://doi.org/10.1243/PIME_PROC_1995_209_351_02.

[29] Yap C H, Saikrishnan N, Tamilselvan G, Yoganathan A P. Experimental measurement of dynamic fluid shear stress on the aortic surface of the aortic valve leaflet. Biomech Model Mechanobiol 2012; 11:171-82. https://doi.org/10.1007/s10237-011-0301-7.

[30] Yap C H, Kim H-S, Balachandran K, Weiler M, Haj-Ali R, Yoganathan A P. Dynamic deformation characteristics of porcine aortic valve leaflet under normal and hypertensive conditions. American Journal of Physiology-Heart and Circulatory Physiology 2009; 298:H395-405. https://doi.org/10.1152/ajpheart.00040.2009.

[31] Li J, Luo X Y, Kuang Z B. A nonlinear anisotropic model for porcine aortic heart valves. Journal of Biomechanics 2001; 34:1279-89. https://doi.org/10.1016/S0021-9290(01)00092-6.

[32] Yao J, Liu G R, Narmoneva D A, Hinton R B, Zhang Z-Q. Immersed smoothed finite element method for fluid-structure interaction simulation of aortic valves. Comput Mech 2012; 50:789-804. https://doi.org/10.1007/s00466-012-0781-z.

[33] Bäck M, Gasser T C, Michel J-B, Caligiuri G. Biomechanical factors in the biology of aortic wall and aortic valve diseases. Cardiovascular Research 2013; 99:232-41. https://doi.org/10.1093/cvr/cvt040.

[34] Yap C H, Saikrishnan N, Yoganathan A P. Experimental measurement of dynamic fluid shear stress on the ventricular surface of the aortic valve leaflet. Biomech Model Mechanobiol 2012; 11:231-44. https://doi.org/10.1007/s10237-011-0306-2.

[35] Pawade Tania, Clavel Marie-Annick, Tribouilloy Christophe, Dreyfus Julien, Mathieu Tiffany, Tastet Lionel, et al. Computed Tomography Aortic Valve Calcium Scoring in Patients With Aortic Stenosis. Circulation: Cardiovascular Imaging 2018; 11:e007146. https://doi.org/10.1161/CIRCIMAGING.117.007146.

[36] Kheradvar A, editor. Principles of heart valve engineering. 1st ed. Cambridge: Elsevier Inc; 2019.

[37] Wu M C H, Zakerzadeh R, Kamensky D, Kiendl J, Sacks M S, Hsu M-C. An anisotropic constitutive model for immersogeometric fluid-structure interaction analysis of bioprosthetic heart valves. Journal of Biomechanics 2018; 74:23-31. https://doi.org/10.1016/j.jbiomech.2018.04.012.

[38] Zakerzadeh R, Hsu M-C, Sacks M S. Computational Methods for the Aortic Heart Valve and its Replacements. Expert Rev Med Devices 2017; 14:849-66. https://doi.org/10.1080/17434440.2017.1389274.

[39] Ben-Assa E, Brown J, Keshavarz-Motamed Z, de la Torre Hernandez J M, Leiden B, Olender M, et al. Ventricular stroke work and vascular impedance refine the characterization of patients with aortic stenosis. Sci Transl Med 2019; 11. https://doi.org/10.1126/scitranslmed.aaw0181.

[40] Borlaug B A, Kass D A. Ventricular-Vascular Interaction in Heart Failure. Heart Failure Clinics 2008; 4:23-36. https://doi.org/10.1016/j.hfc.2007.10.001.

[41] Dweck M R, Boon N A, Newby D E. Calcific Aortic Stenosis: A Disease of the Valve and the Myocardium. Journal of the American College of Cardiology 2012; 60:1854-63. https://doi.org/10.1016/j.jacc.2012.02.093.

[42] Ikonomidis I, Aboyans V, Blacher J, Brodmann M, Brutsaert D L, Chirinos J A, et al. The role of ventricular-arterial coupling in cardiac disease and heart failure: assessment, clinical implications and therapeutic interventions. A consensus document of the European Society of Cardiology Working Group on Aorta & Peripheral Vascular Diseases, European Association of Cardiovascular Imaging, and Heart Failure Association. European Journal of Heart Failure 2019; 21:402-24. https://doi.org/10.1002/ejhf.1436.

[43] Keshavarz-Motamed Z. A diagnostic, monitoring, and predictive tool for patients with complex valvular, vascular and ventricular diseases. Sci Rep 2020; 10:1-19. https://doi.org/10.1038/s41598-020-63728-8.

[44] Pibarot P, Dumesnil J G. Improving Assessment of Aortic Stenosis. Journal of the American College of Cardiology 2012; 60:169-80. https://doi.org/10.1016/j.jacc.2011.11.078.

[45] Garber L, Khodaei S, Keshavarz-Motamed Z. The Critical Role of Lumped Parameter Models in Patient-Specific Cardiovascular Simulations. Arch Computat Methods Eng 2021. https://doi.org/10.1007/s11831-021-09685-5.

[46] Kadem M, Garber L, Abdelkhalek M, K. A I-Khazraji B, Keshavarz-Motamed Z. Hemodynamic modeling, medical imaging, and machine learning and their applications to cardiovascular interventions. IEEE Reviews in Biomedical Engineering 2022:1-1. https://doi.org/10.1109/RBME.2022.3142058.

[47] Khodaei S, Henstock A, Sadeghi R, Sellers S, Blanke P, Leipsic J, et al. Personalized intervention cardiology with transcatheter aortic valve replacement made possible with a non-invasive monitoring and diagnostic framework. Sci Rep 2021; 11:10888. https://doi.org/10.1038/s41598-021-85500-2.

[48] Khodaei S, Sadeghi R, Blanke P, Leipsic J, Emadi A, Keshavarz-Motamed Z. Towards a non-invasive computational diagnostic framework for personalized cardiology of transcatheter aortic valve replacement in interactions with complex valvular, ventricular and vascular disease. International Journal of Mechanical Sciences 2021; 202-203:106506. https://doi.org/10.1016/j.ijmecsci.2021.106506.

[48] Amindari A, Saltik L, Kirkkopru K, Yacoub M, Yalcin H C. Assessment of calcified aortic valve leaflet deformations and blood flow dynamics using fluid-structure interaction modeling. Informatics in Medicine Unlocked 2017; 9:191-9. https://doi.org/10.1016/j.imu.2017.09.001.

[50] Dabiri Y, Sack K L, Rebelo N, Wang P, Wang Y, Choy J S, et al. Method for Calibration of Left Ventricle Material Properties Using Three-Dimensional Echocardiography Endocardial Strains. Journal of Biomechanical Engineering 2019; 141. https://doi.org/10.1115/1.4044215.

[51] Liogky A, Karavaikin P, Salamatova V. Impact of Material Stiffness and Anisotropy on Coaptation Characteristics for Aortic Valve Cusps Reconstructed from Pericardium. Mathematics 2021; 9:2193. https://doi.org/10.3390/math9182193.

[52] Alqahtani A M, Boczar K E, Kansal V, Chan K, Dwivedi G, Chow B J W. Quantifying Aortic Valve Calcification using Coronary Computed Tomography Angiography. Journal of Cardiovascular Computed Tomography 2017; 11:99-104. https://doi.org/10.1016/j.jcct.2017.01.007.

[53] Dimasi A, Stevanella M, Votta E, Sturla F, Burriesci G, Redaelli A. Finite Element Analysis of Transcatheter Aortic Valve Implantation in the Presence of Aortic Leaflet Calcifications. In: Lenarz T, Wriggers P, editors. Biomedical Technology, Cham: Springer International Publishing; 2015, p. 101-15. https://doi.org/10.1007/978-3-319-10981-7_7.

[54] Luraghi G, Matas J F R, Beretta M, Chiozzi N, Iannetti L, Migliavacca F. The impact of calcification patterns in transcatheter aortic valve performance: a fluid-structure interaction analysis. Computer Methods in Biomechanics and Biomedical Engineering 2021; 24:375-83. https://doi.org/10.1080/10255842.2020.1817409.

[55] Pawade T, Sheth T, Guzzetti E, Dweck M R, Clavel M-A. Why and How to Measure Aortic Valve Calcification in Patients With Aortic Stenosis. JACC: Cardiovascular Imaging 2019; 12:1835-48. https://doi.org/10.1016/j.jcmg.2019.01.045.

[56] Blanke P, Weir-McCall J R, Achenbach S, Delgado V, Hausleiter J, Jilaihawi H, et al. Computed Tomography Imaging in the Context of Transcatheter Aortic Valve Implantation (TAVI)/Transcatheter Aortic Valve Replacement (TAVR): An Expert Consensus Document of the Society of Cardiovascular Computed Tomography. JACC: Cardiovascular Imaging 2019; 12:1-24. https://doi.org/10.1016/j.jcmg.2018.12.003.

[57] Fassa A-A, Himbert D, Vahanian A. Mechanisms and management of TAVR-related complications. Nat Rev Cardiol 2013; 10:685-95. https://doi.org/10.1038/nrcardio.2013.156.

[58] Pislaru S V, Nkomo V T, Sandhu G S. Assessment of Prosthetic Valve Function After TAVR. JACC: Cardiovascular Imaging 2016; 9:193-206. https://doi.org/10.1016/j.jcmg.2015.11.010.

[59] Schäfers H-J, Schmied W, Marom G, Aicher D. Cusp height in aortic valves. The Journal of Thoracic and Cardiovascular Surgery 2013; 146:269-74. https://doi.org/10.1016/j.jtcvs.2012.06.053.

[60] Jermihov P N, Jia L, Sacks M S, Gorman R C, Gorman J H, Chandran K B. Effect of Geometry on the Leaflet Stresses in Simulated Models of Congenital Bicuspid Aortic Valves. Cardiovasc Eng Tech 2011; 2:48-56. https://doi.org/10.1007/s13239-011-0035-9.

[61] Gray R A, Pathmanathan P. Patient-Specific Cardiovascular Computational Modeling: Diversity of Personalization and Challenges. J of Cardiovasc Trans Res 2018; 11:80-8. https://doi.org/10.1007/s12265-018-9792-2.

[62] Kaboudian A, Cherry E M, Fenton F H. Real-time interactive simulations of large-scale systems on personal computers and cell phones: Toward patient-specific heart modeling and other applications. Science Advances 2019; 5:eaav6019. https://doi.org/10.1126/sciadv.aav6019.

[63] Kheradvar A, Groves E M, Goergen C J, Alavi S H, Tranquillo R, Simmons C A, et al. Emerging Trends in Heart Valve Engineering: Part I I. Novel and Standard Technologies for Aortic Valve Replacement. Ann Biomed Eng 2015; 43:844-57. https://doi.org/10.1007/s10439-014-1191-5.

[64] Arzani A, Wang J-X, Sacks M S, Shadden S C. Machine Learning for Cardiovascular Biomechanics Modeling: Challenges and Beyond. Ann Biomed Eng 2022; 50:615-27. https://doi.org/10.1007/s10439-022-02967-4.

[65] Baek S, Arzani A. Current state-of-the-art and utilities of machine learning for detection, monitoring, growth prediction, rupture risk assessment, and post-surgical management of abdominal aortic aneurysms. Applications in Engineering Science 2022; 10:100097. https://doi.org/10.1016/j.apples.2022.100097.

[66] Hicks J L, Uchida T K, Seth A, Rajagopal A, Delp S L. Is My Model Good Enough? Best Practices for Verification and Validation of Musculoskeletal Models and Simulations of Movement. Journal of Biomechanical Engineering 2015; 137. https://doi.org/10.1115/1.4029304.

[67] Land S, Gurev V, Arens S, Augustin C M, Baron L, Blake R, et al. Verification of cardiac mechanics software: benchmark problems and solutions for testing active and passive material behaviour. Proceedings of the Royal Society A: Mathematical, Physical and Engineering Science 2015; 471:20150641. https://doi.org/10.1098/rspa.2015.0641.

[68] Steinman D A, Migliavacca F. Editorial: Special Issue on Verification, Validation, and Uncertainty Quantification of Cardiovascular Models: Towards Effective VVUQ for Translating Cardiovascular Modelling to Clinical Utility. Cardiovasc Eng Tech 2018; 9:539-43. https://doi.org/10.1007/s13239-018-00393-z.

[69] Sun W, Mao W, Griffith B E. Computer modeling and simulation of heart valve function and intervention. Principles of Heart Valve Engineering, Elsevier; 2019, p. 177-211. https://doi.org/10.1016/B978-0-12-814661-3.00007-1.

[70] Taylor C A, Steinman D A. Image-Based Modeling of Blood Flow and Vessel Wall Dynamics: Applications, Methods and Future Directions. Ann Biomed Eng 2010; 38:1188-203. https://doi.org/10.1007/s10439-010-9901-0.

[71] Annerel S, Claessens T, Degroote J, Segers P, Vierendeels J. Validation of a numerical FSI simulation of an aortic BMHV by in vitro PIV experiments. Medical Engineering & Physics 2014; 36:1014-23. https://doi.org/10.1016/j.medengphy.2014.05.004.

[72] Arzani A, Mofrad M R K. A strain-based finite element model for calcification progression in aortic valves. Journal of Biomechanics 2017; 65:216-20. https://doi.org/10.1016/j.jbiomech.2017.10.014.

[73] Auricchio F, Conti M, Morganti S, Reali A. Simulation of transcatheter aortic valve implantation: a patient-specific finite element approach. Comput Methods Biomech Biomed Engin 2014; 17:1347-57. https://doi.org/10.1080/10255842.2012.746676.

[74] Cao K, Atkins S K, McNally A, Liu J, Sucosky P. Simulations of morphotype-dependent hemodynamics in non-dilated bicuspid aortic valve aortas. Journal of Biomechanics 2017; 50:63-70. https://doi.org/10.1016/j.jbiomech.2016.11.024.

[75] Cao K, Sucosky P. Computational comparison of regional stress and deformation characteristics in tricuspid and bicuspid aortic valve leaflets: Tricuspid and Bicuspid Aortic Valve Mechanics. Int J Numer Meth Biomed Engng 2017; 33:e02798. https://doi.org/10.1002/cnm.2798.

[76] Chen Y, Luo H. A computational study of the three-dimensional fluid-structure interaction of aortic valve. Journal of Fluids and Structures 2018; 80:332-49. https://doi.org/10.1016/j.jfluidstructs.2018.04.009.

[77] De Vita F, de Tullio M D, Verzicco R. Numerical simulation of the non-Newtonian blood flow through a mechanical aortic valve: Non-Newtonian blood flow in the aortic root. Theor Comput Fluid Dyn 2016; 30:129-38. https://doi.org/10.1007/s00162-015-0369-2.

[78] Grande K J, Cochran R P, Reinhall P G, Kunzelman K S. Mechanisms of aortic valve incompetence: finite element modeling of aortic root dilatation. The Annals of Thoracic Surgery 2000; 69:1851-7. https://doi.org/10.1016/S0003-4975(00)01307-2.

[79] Grande-Allen K J, Cochran R P, Reinhall P G, Kunzelman K S. Mechanisms of aortic valve incompetence: Finite-element modeling of Marfan syndrome. The Journal of Thoracic and Cardiovascular Surgery 2001; 122: 946-54. https://doi.org/10.1067/mtc.2001.116314.

[80] Haj-Ali R, Dasi L P, Kim H-S, Choi J, Leo H W, Yoganathan A P. Structural simulations of prosthetic tri-leaflet aortic heart valves. Journal of Biomechanics 2008; 41:1510-9. https://doi.org/10.1016/j.jbiomech.2008.02.026.

[81] Katayama S, Umetani N, Hisada T, Sugiura S. Bicuspid aortic valves undergo excessive strain during opening: A simulation study. The Journal of Thoracic and Cardiovascular Surgery 2013; 145:1570-6. https://doi.org/10.1016/j.jtcvs.2012.05.032.

[82] Kulp S, Qian Z, Vannan M, Rinehart S, Metaxas D. Patient-specific aortic valve blood flow simulations. 2014 IEEE 11th International Symposium on Biomedical Imaging (ISBI), 2014, p. 939-42. https://doi.org/10.1109/ISBI.2014.6868026.

[83] Li K, Sun W. Simulated transcatheter aortic valve deformation: A parametric study on the impact of leaflet geometry on valve peak stress. International Journal for Numerical Methods in Biomedical Engineering 2017; 33:e02814. https://doi.org/10.1002/cnm.2814.

[84] Mao W, Li K, Sun W. Fluid-Structure Interaction Study of Transcatheter Aortic Valve Dynamics Using Smoothed Particle Hydrodynamics. Cardiovasc Eng Tech 2016; 7:374-88. https://doi.org/10.1007/s13239-016-0285-7.

[85] Marom G, Haj-Ali R, Raanani E, Schäfers H-J, Rosenfeld M. A fluid-structure interaction model of the aortic valve with coaptation and compliant aortic root. Medical & Biological Engineering & Computing 2012; 50:173-82. https://doi.org/10.1007/s11517-011-0849-5.

[86] Martin C, Sun W. Comparison of transcatheter aortic valve and surgical bioprosthetic valve durability: a fatigue simulation study. J Biomech 2015; 48:3026-34. https://doi.org/10.1016/j.jbiomech.2015.07.031.

[87] Morganti S, Auricchio F, Benson D J, Gambarin F I, Hartmann S, Hughes T J R, et al. Patient-specific isogeometric structural analysis of aortic valve closure. Computer Methods in Applied Mechanics and Engineering 2015; 284:508-20. https://doi.org/10.1016/j.cma.2014.10.010.

[88] Smuts A N, Blaine D C, Scheffer C, Weich H, Doubell A F, Dellimore K H. Application of finite element analysis to the design of tissue leaflets for a percutaneous aortic valve. Journal of the Mechanical Behavior of Biomedical Materials 2011; 4:85-98. https://doi.org/10.1016/j.jmbbm.2010.09.009.

[89] Spühler J H, Jansson J, Jansson N, Hoffman J. 3D Fluid-Structure Interaction Simulation of Aortic Valves Using a Unified Continuum ALE FEM Model. Front Physiol 2018; 9. https://doi.org/10.3389/fphys.2018.00363.

[90] Sun W, Abad A, Sacks M S. Simulated Bioprosthetic Heart Valve Deformation under Quasi-Static Loading. J Biomech Eng 2005; 127:905-14. https://doi.org/10.1115/1.2049337.

[91] Weinberg E J, Kaazempur Mofrad M R. A multiscale computational comparison of the bicuspid and tricuspid aortic valves in relation to calcific aortic stenosis. J Biomech 2008; 41:3482-7. https://doi.org/10.1016/j.jbiomech.2008.08.006.

[92] Weinberg E J, Kaazempur-Mofrad M R. On the Constitutive Models for Heart Valve Leaflet Mechanics. Cardiovasc Eng 2005; 5:37-43. https://doi.org/10.1007/s10558-005-3072-x.

[93] Joda A, Jin Z, Haverich A, Summers J, Korossis S. Multiphysics simulation of the effect of leaflet thickness inhomogeneity and material anisotropy on the stress-strain distribution on the aortic valve. Journal of Biomechanics 2016; 49:2502-12. https://doi.org/10.1016/j.jbiomech.2016.02.041.

[98] Dhondt G. The Finite Element Method for Three-Dimensional Thermomechanical Applications: Dhondt/Three-Dimensional Thermomechanical Applications. Chichester, U K: John Wiley & Sons, Ltd; 2004. https://doi.org/10.1002/0470021217.

[99] Haj-Ali R, Marom G, Ben Zekry S, Rosenfeld M, Raanani E. A general three-dimensional parametric geometry of the native aortic valve and root for biomechanical modeling. Journal of Biomechanics 2012; 45:2392-7. https://doi.org/10.1016/j.jbiomech.2012.07.017.

[100] Thubrikar M. The aortic valve. Boca Raton, Fla: CRC Press; 1990.

[101] Labrosse M R, Beller C J, Robicsek F, Thubrikar M J. Geometric modeling of functional trileaflet aortic valves: Development and clinical applications. Journal of Biomechanics 2006; 39:2665-72. https://doi.org/10.1016/j.jbiomech.2005.08.012.

[102] Morganti S. Finite Element Analysis of Aortic Valve Surgery. PhD Thesis. Doctoral thesis, Universita degli Studi di Pavia, Italy, 2011.

[103] Jaskulski A. Autodesk Inventor Professional 2016P L/2016/Fusion 360+ metodyka projektowania. vol. 1. Wydawnictwo Naukowe PWN; 2015.

[104] Grande K J, Cochran R P, Reinhall P G, Kunzelman K S. Mechanisms of aortic valve incompetence: finite element modeling of aortic root dilatation. Ann Thorac Surg 2000; 69:1851-7. https://doi.org/10.1016/s0003-4975(00)01307-2.

[105] Labrosse M R, Beller C J, Boodhwani M, Hudson C, Sohmer B. Subject-specific finite-element modeling of normal aortic valve biomechanics from 3D+t TEE images. Medical Image Analysis 2015; 20:162-72. https://doi.org/10.1016/j.media.2014.11.003.

[106] Marom G, Hee-Sun Kim, Rosenfeld M, Raanani E, Haj-Ali R. Effect of asymmetry on hemodynamics in fluid-structure interaction model of congenital bicuspid aortic valves. 2012 Annual International Conference of the IEEE Engineering in Medicine and Biology Society, San Diego, C A: IEEE; 2012, p. 637-40. https://doi.org/10.1109/EMBC.2012.6346012.

[107] Bathe K-J. Finite element procedures. 2nd ed. Englewood Cliffs, N. J: Prentice-Hall; 2014.

[108] Miranda I, Ferencz R M, Hughes T J. An improved implicit-explicit time integration method for structural dynamics. Earthquake Engineering & Structural Dynamics 1989; 18:643-53.

[109] Ashcraft C, Grimes R G. SPOOLES: An Object-Oriented Sparse Matrix Library. PPSC, 1999.

[110] Van de Vosse F N, de Hart J, van Oijen CHGA, Bessems D, Gunther T W M, Segal A, et al. Finite-element-based computational methods for cardiovascular fluid-structure interaction. Journal of Engineering Mathematics 2003; 47:335-68. https://doi.org/10.1023/B:ENGI.0000007985.17625.43.

[111] Marom G. Numerical Methods for Fluid-Structure Interaction Models of Aortic Valves. Archives of Computational Methods in Engineering 2015; 22:595-620. https://doi.org/10.1007/s11831-014-9133-9.

[112] Abbasi M, Barakat M S, Vahidkhah K, Azadani A N. Characterization of three-dimensional anisotropic heart valve tissue mechanical properties using inverse finite element analysis. Journal of the Mechanical Behavior of Biomedical Materials 2016; 62:33-44. https://doi.org/10.1016/j.jmbbm.2016.04.031.

[113] Anssari-Benam A, Bader D L, Screen H R C. Anisotropic time-dependant behaviour of the aortic valve. Journal of the Mechanical Behavior of Biomedical Materials 2011; 4:1603-10. https://doi.org/10.1016/j.jmbbm.2011.02.010.

[114] Deck J D, Thubrikar M J, Schneider P J, Nolan S P. Structure, stress, and tissue repair in aortic valve leaflets. Cardiovasc Res 1988; 22:7-16. https://doi.org/10.1093/cvr/22.1.7.

[115] Koch T M, Reddy B D, Zilla P, Franz T. Aortic valve leaflet mechanical properties facilitate diastolic valve function. Computer Methods in Biomechanics and Biomedical Engineering 2010; 13:225-34. https://doi.org/10.1080/10255840903120160.

[116] Amindari A, Kırkköprü K, Saltık �, Sünbüloğlu E. Effect of non-linear leaflet material properties on aortic valve dynamics—A coupled fluid-structure approach. Engineering Solid Mechanics 2021; 9:123-36.

[117] Kim H S. Nonlinear multi-scale anisotropic material and structural models for prosthetic and native aortic heart valves. PhD Thesis. Georgia Institute of Technology, 2009.

[118] Billiar K L, Sacks M S. Biaxial Mechanical Properties of the Native and Glutaraldehyde-Treated Aortic Valve Cusp: Part II—A Structural Constitutive Model. J Biomech Eng 2000; 122:327-35. https://doi.org/10.1115/1.1287158.

[119] Aguilera H M, Urheim S, Skallerud B, Prot V. Influence of Annular Dynamics and Material Behavior in Finite Element Analysis of Barlow's Mitral Valve Disease. J Elast 2021; 145:163-90. https://doi.org/10.1007/s10659-021-09829-5.

[120] Karabelas E, Gsell M A F, Haase G, Plank G, Augustin C M. An accurate, robust, and efficient finite element framework for anisotropic, nearly and fully incompressible elasticity. ArXiv:211100612 [Physics] 2021.

[121] Kong F, Pham T, Martin C, Elefteriades J, McKay R, Primiano C, et al. Finite element analysis of annuloplasty and papillary muscle relocation on a patient-specific mitral regurgitation model. PLOS ONE 2018; 13:e0198331. https://doi.org/10.1371/journal.pone.0198331.

[122] Lally C, Dolan F, Prendergast P J. Cardiovascular stent design and vessel stresses: a finite element analysis. Journal of Biomechanics 2005; 38:1574-81. https://doi.org/10.1016/j.jbiomech.2004.07.022.

[123] Humphrey J D. Cardiovascular Solid Mechanics: Cells, Tissues, and Organs. Springer Science & Business Media; 2013.

[124] Humphrey J D, Yin F C P. On Constitutive Relations and Finite Deformations of Passive Cardiac Tissue: I. A Pseudostrain-Energy Function. J Biomech Eng 1987; 109:298-304. https://doi.org/10.1115/1.3138684.

[125] Holzapfel G A, Sommer G, Gasser C T, Regitnig P. Determination of layer-specific mechanical properties of human coronary arteries with nonatherosclerotic intimal thickening and related constitutive modeling. Am J Physiol Heart Circ Physiol 2005; 289:H2048-2058. https://doi.org/10.1152/ajpheart.00934.2004.

[126] Marom G, Kim H-S, Rosenfeld M, Raanani E, Haj-Ali R. Fully coupled fluid-structure interaction model of congenital bicuspid aortic valves: effect of asymmetry on hemodynamics. Med Biol Eng Comput 2013; 51:839-48. https://doi.org/10.1007/s11517-013-1055-4.

[127] Bohbot Yohann, Renard Cédric, Manrique Alain, Levy Franck, Maréchaux Sylvestre, Gerber Bernhard L., et al. Usefulness of Cardiac Magnetic Resonance Imaging in Aortic Stenosis. Circulation: Cardiovascular Imaging 2020; 13:e010356. https://doi.org/10.1161/CIRCIMAGING.119.010356.

[128] Martin C, Pham T, Sun W. Significant differences in the material properties between aged human and porcine aortic tissues. Eur J Cardiothorac Surg 2011; 40:28-34. https://doi.org/10.1016/j.ejcts.2010.08.056.

[129] Maleki H, Shahriari S, Durand L G, Labrosse M R, Kadem L. A metric for the stiffness of calcified aortic valves using a combined computational and experimental approach. Med Biol Eng Comput 2014; 52:1-8. https://doi.org/10.1007/s11517-013-1113-y.

[130] Saikrishnan N, Kumar G, Sawaya F J, Lerakis S, Yoganathan A P. Accurate Assessment of Aortic Stenosis. Circulation 2014; 129:244-53. https://doi.org/10.1161/CIRCULATIONAHA.113.002310.

[131] Adda J, Stanova V, Habib G, Rieu R. In vitro correlation between the effective and geometric orifice area in aortic stenosis. J Cardiol 2021; 77:334-40. https://doi.org/10.1016/j.jjcc.2020.08.003.

[132] Garcia D, Pibarot P, Landry C, Allard A, Chayer B, Dumesnil J G, et al. Estimation of aortic valve effective orifice area by Doppler echocardiography: effects of valve inflow shape and flow rate. J Am Soc Echocardiogr 2004; 17:756-65. https://doi.org/10.1016/j.echo.2004.03.030.

[133] Halevi R, Hamdan A, Marom G, Mega M, Raanani E, Haj-Ali R. Progressive aortic valve calcification: Three-dimensional visualization and biomechanical analysis. Journal of Biomechanics 2015; 48:489-97. https://doi.org/10.1016/j.jbiomech.2014.12.004.

[134] Geuzaine C, Remacle J F. GMSH User's Manual. GMSH, Version 2006; 62.

[135] Geuzaine C, Remacle J-F. Gmsh: A 3-D finite element mesh generator with built-in pre- and post-processing facilities. International Journal for Numerical Methods in Engineering 2009; 79:1309-31.

[136] Kanok-Nukulchai W, Barry W, Saran-Yasoontorn K, Bouillard P H. On elimination of shear locking in the element-free Galerkin method. International Journal for Numerical Methods in Engineering 2001; 52:705-25. https://doi.org/10.1002/nme.223.

[137] Zienkiewicz O C, Taylor R L, Taylor R L, Taylor R L. The Finite Element Method: Solid mechanics. Butterworth-Heinemann; 2000.

[138] Boerboom R A, Driessen N J B, Bouten C V C, Huyghe J M, Baaijens F P T. Finite Element Model of Mechanically Induced Collagen Fiber Synthesis and Degradation in the Aortic Valve. Annals of Biomedical Engineering 2003; 31:1040-53. https://doi.org/10.1114/1.1603749.

[139] De Hart J, Peters G W M, Schreurs P J G, Baaijens F P T. Collagen fibers reduce stresses and stabilize motion of aortic valve leaflets during systole. Journal of Biomechanics 2004; 37:303-11. https://doi.org/10.1016/S0021-9290(03)00293-8.

[140] Flamini V, DeAnda A, Griffith B E. Immersed boundary-finite element model of fluid-structure interaction in the aortic root. Theor Comput Fluid Dyn 2016; 30:139-64. https://doi.org/10.1007/s00162-015-0374-5.

[141] Labrosse M R, Lobo K, Beller C J. Structural analysis of the natural aortic valve in dynamics: From unpressurized to physiologically loaded. Journal of Biomechanics 2010; 43:1916-22. https://doi.org/10.1016/j.jbiomech.2010.03.020.

[142] Luraghi G, Migliavacca F, Rodriguez Matas J F. Study on the Accuracy of Structural and FSI Heart Valves Simulations. Cardiovasc Eng Tech 2018. https://doi.org/10.1007/s13239-018-00373-3.

[143] Baiocchi M, Barsoum S, Khodaei S, de la Torre Hernandez J M, Valentino S E, Dunford E C, et al. Effects of Choice of Medical Imaging Modalities on a Non-invasive Diagnostic and Monitoring Computational Framework for Patients With Complex Valvular, Vascular, and Ventricular Diseases Who Undergo Transcatheter Aortic Valve Replacement. Frontiers in Bioengineering and Biotechnology 2021; 9:389. https://doi.org/10.3389/fbioe.2021.643453.

[144] Karlov V, Simakov S. An Algorithm for Visualization of Patient-specific C T-based Vascular Data for the Model of 1 D Hemodynamics. CEUR Workshop Proceedings, 2019, p. 52-61.

[145] Moreland K. The paraview tutorial. Sandia National Laboratories, Tech Rep SAND 2013.

[146] Virtanen P, Gommers R, Oliphant T E, Haberland M, Reddy T, Cournapeau D, et al. SciPy 1.0: fundamental algorithms for scientific computing in Python. Nat Methods 2020; 17:261-72. https://doi.org/10.1038/s41592-019-0686-2.

[147] Wang H M, Luo X Y, Gao H, Ogden R W, Griffith B E, Berry C, et al. A modified Holzapfel-Ogden law for a residually stressed finite strain model of the human left ventricle in diastole. Biomechanics and Modeling in Mechanobiology 2014; 13:99-113. https://doi.org/10.1007/s10237-013-0488-x.

[148] Keshavarz-Motamed Z, Rikhtegar Nezami F, Partida R A, Nakamura K, Staziaki P V, Ben-Assa E, et al. Elimination of Transcoarctation Pressure Gradients Has No Impact on Left Ventricular Function or Aortic Shear Stress After Intervention in Patients With Mild Coarctation. JACC: Cardiovascular Interventions 2016; 9:1953-65. https://doi.org/10.1016/j.jcin.2016.06.054.

[149] Sadeghi R, Khodaei S, Ganame J, Keshavarz-Motamed Z. Towards non-invasive computational-mechanics and imaging-based diagnostic framework for personalized cardiology for coarctation. Sci Rep 2020; 10:9048. https://doi.org/10.1038/s41598-020-65576-y.

[150] Keshavarz-Motamed Z, Garcia J, Gaillard E, Capoulade R, Ven F L, Cloutier G, et al. Non-Invasive Determination of Left Ventricular Workload in Patients with Aortic Stenosis Using Magnetic Resonance Imaging and Doppler Echocardiography. PLOS ONE 2014; 9:e86793. https://doi.org/10.1371/journal.pone.0086793.

[151] Asaadi M, Mawad W, Djebbari A, Keshavardz-Motamed Z, Dahdah N, Kadem L. On Left Ventricle Stroke Work Efficiency in Children with Moderate Aortic Valve Regurgitation or Moderate Aortic Valve Stenosis. Pediatr Cardiol 2021. https://doi.org/10.1007/s00246-021-02690-2.

[152] Benevento E, Djebbari A, Keshavarz-Motamed Z, Cecere R, Kadem L. Hemodynamic Changes following Aortic Valve Bypass: A Mathematical Approach. PLOS ONE 2015; 10:e0123000. https://doi.org/10.1371/journal.pone.0123000.

[153] Keshavarz-Motamed Z, Edelman E R, Motamed P K, Garcia J, Dahdah N, Kadem L. The role of aortic compliance in determination of coarctation severity: Lumped parameter modeling, in vitro study and clinical evaluation. Journal of Biomechanics 2015; 48:4229-37. https://doi.org/10.1016/j.jbiomech.2015.10.017.

[154] Keshavarz-Motamed Z, Garcia J, Pibarot P, Larose E, Kadem L. Modeling the impact of concomitant aortic stenosis and coarctation of the aorta on left ventricular workload. Journal of Biomechanics 2011; 44:2817-25. https://doi.org/10.1016/j.jbiomech.2011.08.001.

[155] Baumgartner H (chair), Hung J (co-chair), Bermejo J, Chambers J B, Edvardsen T, Goldstein S, et al. Recommendations on the echocardiographic assessment of aortic valve stenosis: a focused update from the European Association of Cardiovascular Imaging and the American Society of Echocardiography. European Heart Journal—Cardiovascular Imaging 2017; 18:254-75. https://doi.org/10.1093/ehjci/jew335.

[156] Lang R M, Badano L P, Mor-Avi V, Afilalo J, Armstrong A, Ernande L, et al. Recommendations for Cardiac Chamber Quantification by Echocardiography in Adults: An Update from the American Society of Echocardiography and the European Association of Cardiovascular Imaging. Eur Heart J Cardiovasc Imaging 2015; 16:233-71. https://doi.org/10.1093/ehjci/jev014.

[157] Einarsen E, Cramariuc D, Bahlmann E, Midtbo H, Chambers J B, Gerdts E. Higher Acceleration/Ejection Time Ratio Predicts Impaired Outcome in Aortic Valve Stenosis. Circulation: Cardiovascular Imaging 2021; 14:e011467. https://doi.org/10.1161/CIRCIMAGING.120.011467.

[158] Gamaza-Chulián S, Díaz-Retamino E, Camacho-Freire S, Ruiz-Fernández D, Gutiérrez-Barrios A, Oneto-Otero J. Acceleration Time and Ratio of Acceleration Time to Ejection Time in Aortic Stenosis: New Echocardiographic Diagnostic Parameters. Journal of the American Society of Echocardiography 2017; 30:947-55. https://doi.org/10.1016/j.echo.2017.06.001.

[159] Nagueh, S. F., Smiseth, O. A., Appleton, C. P., Byrd, B. F., Dokainish, H., Edvardsen, T., Flachskampf, F. A., Gillebert, T. C., Klein, A. L., Lancellotti, P., 2016. Recommendations for the evaluation of left ventricular diastolic function by echocardiography: an update from the American Society of Echocardiography and the European Association of Cardiovascular Imaging. Eur. J. Echocardiogr. 17, 1321-1360.

[160] Pollock J D, Makaryus A N. Physiology, Cardiac Cycle. StatPearls, Treasure Island (F L): StatPearls Publishing; 2021.

[161] Briand M, Dumesnil J G, Kadem L, Tongue A G, Rieu R, Garcia D, et al. Reduced Systemic Arterial Compliance Impacts Significantly on Left Ventricular Afterload and Function in Aortic Stenosis: Implications for Diagnosis and Treatment. Journal of the American College of Cardiology 2005; 46:291-8. https://doi.org/10.1016/j.jacc.2004.10.081.

[162] Bahlmann E, Cramariuc D, Saeed S, Chambers J B, Nienaber C A, Kuck K-H, et al. Low systemic arterial compliance is associated with increased cardiovascular morbidity and mortality in aortic valve stenosis. Heart 2019; 105:1507-14. https://doi.org/10.1136/heartjnl-2018-314386.

[163] Auricchio, F., Ferrara, A., Morganti, S., 2012. Comparison and critical analysis of invariant-based models with respect to their ability in fitting human aortic valve data. Ann. Solid Struct. Mech. 4, 1-14. https://doi.org/10.1007/s12356-012-0028-x.

[164] Ayoub, S., Ferrari, G., Gorman, R. C., Gorman III, J. H., Schoen, F. J., Sacks, M. S., 2016. Heart Valve Biomechanics and Underlying Mechanobiology, in: Comprehensive Physiology. John Wiley & Sons, Ltd, pp. 1743-1780. https://doi.org/10.1002/cphy.c150048.

[165] Balachandran, K., Sucosky, P., Jo, H., Yoganathan, A. P., 2010. Elevated Cyclic Stretch Induces Aortic Valve Calcification in a Bone Morphogenic Protein-Dependent Manner. Am. J. Pathol. 177, 49-57. https://doi.org/10.2353/ajpath.2010.090631.

[166] Lee, S. J., Lee, I.-K., Jeon, J.-H., 2020. Vascular Calcification—New Insights into Its Mechanism. Int. J. Mol. Sci. 21, 2685. https://doi.org/10.3390/ijms21082685.

[167] Thubrikar, M. J., Deck, J. D., Aouad, J., Nolan, S. P., 1983. Role of mechanical stress in calcification of aortic bioprosthetic valves. J. Thorac. Cardiovasc. Surg. 86, 115-125. https://doi.org/10.1016/S0022-5223(19)39217-7.

[168] Qin, T., Caballero, A., Mao, W., Barrett, B., Kamioka, N., Lerakis, S., Sun, W., 2020. The role of stress concentration in calcified bicuspid aortic valve. J. R. Soc. Interface 17, 20190893. https://doi.org/10.1098/rsif.2019.0893.

[169] Mohammadi H, Bahramian F, Wan W. Advanced modeling strategy for the analysis of heart valve leaflet tissue mechanics using high-order finite element method. Medical Engineering & Physics 2009; 31:1110-7. https://doi.org/10.1016/j.medengphy.2009.07.012.

[170] Garcia D, Kadem L. What do you mean by aortic valve area: Geometric orifice area, effective orifice area, or Gorlin area? The Journal of Heart Valve Disease 2006; 15:601-8.

[171] Halevi R, Hamdan A, Marom G, Lavon K, Ben-Zekry S, Raanani E, et al. Fluid-structure interaction modeling of calcific aortic valve disease using patient-specific three-dimensional calcification scans. Medical & Biological Engineering & Computing 2016; 54:1683-94. https://doi.org/10.1007/s11517-016-1458-0.

[172] Mutlu O, Salman H E, Yalcin H C, Olcay A B. Fluid Flow Characteristics of Healthy and Calcified Aortic Valves Using Three-Dimensional Lagrangian Coherent Structures Analysis. Fluids 2021; 6:203. https://doi.org/10.3390/fluids6060203.

[173] Arjunon S, Rathan S, Jo H, Yoganathan A P. Aortic Valve: Mechanical Environment and Mechanobiology. Ann Biomed Eng 2013; 41:1331-46. https://doi.org/10.1007/s10439-013-0785-7.

[174] Izquierdo-Gómez, M. M., Hernández-Betancor, I., García-Niebla, J., Marí-López, B., Laynez-Cerdeña, I., Lacalzada-Almeida, J., 2017. Valve Calcification in Aortic Stenosis: Etiology and Diagnostic Imaging Techniques [WVW Document]. BioMed Res. Int. https://doi.org/10.1155/2017/5178631.

[175] Minno, M. N. D. D., Poggio, P., Conte, E., Myasoedova, V., Songia, P., Mushtaq, S., Cavallotti, L., Moschetta, D., Minno, A. D., Spadarella, G., Pizzicato, P., Pontone, G., Pepi, M., Andreini, D., 2019. Cardiovascular morbidity and mortality in patients with aortic valve calcification: A systematic review and meta-analysis. J. Cardiovasc. Comput. Tomogr. 13, 190-195. https://doi.org/10.1016/j.jcct.2019.06.006.

[176] Rogers, M. A., Aikawa, E., 2019. Cardiovascular calcification: artificial intelligence and big data accelerate mechanistic discovery. Nat. Rev. Cardiol. 16, 261-274. https://doi.org/10.1038/s41569-018-0123-8.

[177] Peeters, F. E. C. M., Meex, S. J. R., Dweck, M. R., Aikawa, E., Crijns, H. J. G. M., Schurgers, L. J., Kietselaer, B. L. J. H., 2018. Calcific aortic valve stenosis: hard disease in the heart: A biomolecular approach towards diagnosis and treatment. Eur. Heart J. 39, 2618-2624. https://doi.org/10.1093/eurheartj/ehx653.

[178] Sønderskov, P. S., Lindholt, J. S., Hallas, J., Gerke, O., Hasific, S., Lambrechtsen, J., Steffensen, F. H., Busk, M., Frost, L., Urbonaviciene, G., Karon, M., Kikar, A. M., Rasmussen, L. M., Diederichsen, and A., 2020. Association of aortic valve calcification and vitamin K antagonist treatment. Eur. Heart J.—Cardiovasc. Imaging 21, 718-724. https://doi.org/10.1093/ehjci/jeaa065.

[179] Myasoedova, V. A., Ravani, A. L., Frigerio, B., Valerio, V., Moschetta, D., Songia, P., Poggio, P., 2018. Novel pharmacological targets for calcific aortic valve disease: Prevention and treatments. Pharmacol. Res. 136, 74-82. https://doi.org/10.1016/j.phrs.2018.08.020.

[180] Freeman Rosario V., Otto Catherine M., 2005. Spectrum of Calcific Aortic Valve Disease. Circulation 111, 3316-3326. https://doi.org/10.1161/CIRCULATIONAHA.104.486738.

[181] Rosenhek, R., Maurer, G., Baumgartner, H., 2002. Should early elective surgery be performed in patients with severe but asymptomatic aortic stenosis? Eur. Heart J. 23, 1417-1421. https://doi.org/10.1053/euhj.2002.3163.

[182] Pibarot, P., Dumesnil, J. G., 2007. New concepts in valvular hemodynamics: Implications for diagnosis and treatment of aortic stenosis. Can. J. Cardiol. 23, 40B-47B. https://doi.org/10.1016/SO828-282X(07)71009-7.

[183] Miller, J. D., Weiss, R. M., Heistad, D. D., 2011. Calcific Aortic Valve Stenosis: Methods, Models, and Mechanisms. Circ. Res. 108, 1392-1412. https://doi.org/10.1161/CIRCRESAHA.110.234138.

[184] Omran, H., Schmidt, H., Hackenbroch, M., Illien, S., Bernhardt, P., von der Recke, G., Fimmers, R., Flacke, S., Layer, G., Pohl, C., LUderitz, B., Schild, H., Sommer, T., 2003. Silent and apparent cerebral embolism after retrograde catheterisation of the aortic valve in valvular stenosis: a prospective, randomised study. The Lancet 361, 1241-1246. https://doi.org/10.1016/S0140-6736(03)12978-9.

[185] Villarraga-Gómez, H., Lee, C., Smith, S. T., 2018. Dimensional metrology with X-ray C T: A comparison with CMM measurements on internal features and compliant structures. Precis. Eng. 51, 291-307. https://doi.org/10.1016/j.precisioneng.2017.08.021.

[186] Rehman, R., Yelamanchili, V. S., Makaryus, A. N., 2020. Cardiac Imaging, in: StatPearls. StatPearls Publishing, Treasure Island (F L).

[187] Rigsby, C. K., McKenney, S. E., Hill, K. D., Chelliah, A., Einstein, A. J., Han, B. K., Robinson, J. D., Sammet, C. L., Slesnick, T. C., Frush, D. P., 2018. Radiation dose management for pediatric cardiac computed tomography: a report from the Image Gently 'Have-A-Heart' campaign. Pediatr. Radiol. 48, 5-20. https://doi.org/10.1007/s00247-017-3991-x.

[188] Peterson P G, Berge M, Lichtenberger J P, Hood M N, Ho V B. Cardiac Imaging Modalities and Appropriate Use. Primary Care: Clinics in Office Practice 2018; 45:155-68. https://doi.org/10.1016/j.pop.2017.10.006.

[189] Zoghbi, W. A., 2014. Cardiovascular Imaging: A Glimpse Into The Future. Methodist DeBakey Cardiovasc. J. 10, 139-145. https://doi.org/10.14797/mdcj-10-3-139.

[190] Cartlidge, T. R., Bing, R., Kwiecinski, J., Guzzetti, E., Pawade, T. A., Doris, M. K., Adamson, P. D., Massera, D., Lembo, M., Peeters, F. E. C. M., Couture, C., Berman, D. S., Dey, D., Slomka, P., Pibarot, P., Newby, D. E., Clavel, M.-A., Dweck, M. R., 2021. Contrast-enhanced computed tomography assessment of aortic stenosis. Heart 107, 1905-1911. https://doi.org/10.1136/heartjnl-2020-318556.

[191] Baron Suzanne J., Arnold Suzanne V., Herrmann Howard C., Holmes David R., Szeto Wilson Y., Allen Keith B., et al. Impact of Ejection Fraction and Aortic Valve Gradient on Outcomes of Transcatheter Aortic Valve Replacement. Journal of the American College of Cardiology 2016; 67:2349-58. https://doi.org/10.1016/j.jacc.2016.03.514.

[192] Altes A, Sochala M, Attias D, Dreyfus J, Bohbot Y, Toledano M, et al. Correlates of the ratio of acceleration time to ejection time in patients with aortic stenosis: An echocardiographic and computed tomography study. Archives of Cardiovascular Diseases 2019; 112:567-75. https://doi.org/10.1016/j.acvd.2019.06.004.

[193] Altes A, Thellier N, Bohbot Y, Marsou W, Chadha G, Binda C, et al. Prognostic Impact of the Ratio of Acceleration Time to Ejection Time in Patients With Low Gradient Severe Aortic Stenosis and Preserved Ejection Fraction. The American Journal of Cardiology 2019; 124:1594-600. https://doi.org/10.1016/j.amjcard.2019.07.064.

[194] Zoghbi W A, Chambers J B, Dumesnil J G, Foster E, Gottdiener J S, Grayburn P A, et al. Recommendations for Evaluation of Prosthetic Valves With Echocardiography and Doppler Ultrasound. Journal of the American Society of Echocardiography 2009; 22:975-1014. https://doi.org/10.1016/j.echo.2009.07.013.

[195] Nagueh S F, Bierig S M, Budoff M J, Desai M, Dilsizian V, Eidem B, et al. American Society of Echocardiography Clinical Recommendations for Multimodality Cardiovascular Imaging of Patients with Hypertrophic Cardiomyopathy: Endorsed by the American Society of Nuclear Cardiology, Society for Cardiovascular Magnetic Resonance, and Society of Cardiovascular Computed Tomography. Journal of the American Society of Echocardiography 2011; 24:473-98. https://doi.org/10.1016/j.echo.2011.03.006.

[196] Seemann F, Arvidsson P, Nordlund D, Kopic S, Carlsson M, Arheden H, et al. Noninvasive Quantification of Pressure-Volume Loops From Brachial Pressure and Cardiovascular Magnetic Resonance. Circulation: Cardiovascular Imaging 2019; 12:e008493. https://doi.org/10.1161/CIRCIMAGING.118.008493.

[197] Piroli F, Franchin L, Bruno F, Filippo O D, D'Ascenzo F, Conrotto F. New advances in the prevention of transcatheter aortic valve implantation failure: current and future perspectives. Kardiologia Polska (Polish Heart Journal) 2020; 78:842-9. https://doi.org/10.33963/KP.15522.

[198] Kostyunin A E, Yuzhalin A E, Rezvova M A, Ovcharenko E A, Glushkova T V, Kutikhin A G. Degeneration of Bioprosthetic Heart Valves: Update 2020. JAHA 2020; 9. https://doi.org/10.1161/JAHA.120.018506.

[199] Gnyaneshwar R, Kumar R K, Balakrishnan K R. Dynamic analysis of the aortic valve using a finite element model. The Annals of Thoracic Surgery 2002; 73:1122-9. https://doi.org/10.1016/S0003-4975(01)03588-3.

[200] Zhang Q, Gao B, Yu C. The Effects of Left Ventricular Assist Device Support Level on the Biomechanical States of Aortic Valve. Med Sci Monit 2018; 24:2003-17. https://doi.org/10.12659/MSM.906903.

[201] Saxon J T, Allen K B, Cohen D J, Chhatriwalla A K. Bioprosthetic Valve Fracture During Valve-in-valve TAVR: Bench to Bedside. Interv Cardiol 2018; 13:20-6. https://doi.org/10.15420/icr.2017:29:1.

[202] Treibel T A, Fontana M, Gilbertson J A, Castelletti S, White S K, Scully P R, et al. Occult Transthyretin Cardiac Amyloid in Severe Calcific Aortic Stenosis. Circulation: Cardiovascular Imaging 2016; 9:e005066. https://doi.org/10.1161/CIRCIMAGING.116.005066.

[203] Wood F O, Abbas A E. General Considerations and Etiologies of Aortic Stenosis. In: Abbas A E, editor. Aortic Stenosis: Case-Based Diagnosis and Therapy, London: Springer; 2015, p. 1-20. https://doi.org/10.1007/978-1-4471-5242-2_1.

[204] Tastet L, Enriquez-Sarano Maurice, Capoulade R, Malouf J, Araoz P A, Shen M, et al. Impact of Aortic Valve Calcification and Sex on Hemodynamic Progression and Clinical Outcomes in A S. Journal of the American College of Cardiology 2017; 69:2096-8. https://doi.org/10.1016/j.jacc.2017.02.037.

[205] Marsden A L. Simulation based planning of surgical interventions in pediatric cardiology. Physics of Fluids 2013; 25:101303. https://doi.org/10.1063/1.4825031.

[206] Minagawa T, Saijo Y, Oktamuliani S, Kurokawa T, Nakajima H, Hasegawa K, et al. Left Ventricular Blood Flow Dynamics In Aortic Stenosis Before And After Aortic Valve Replacement. Conf Proc IEEE Eng Med Biol Soc 2018; 2018:3177-80. https://doi.org/10.1109/EMBC.2018.8512954.

[207] Scantlebury D C, Geske J B, Nishimura R A. Limitations of Doppler echocardiography in the evaluation of serial stenoses. Circ Cardiovasc Imaging 2013; 6:850-2. https://doi.org/10.1161/CIRCIMAGING.113.000575.

[208] Bennett C J, Maleszewski J J, Araoz P A. C T and M R Imaging of the Aortic Valve: Radiologic-Pathologic Correlation. RadioGraphics 2012; 32:1399-420. https://doi.org/10.1148/rg.325115727.

[209] Généreux P, Pibarot P, Redfors B, Mack M J, Makkar R R, Jaber W A, et al. Staging classification of aortic stenosis based on the extent of cardiac damage. European Heart Journal 2017; 38:3351-8. https://doi.org/10.1093/eurheartj/ehx381.

We claim:

1. A Doppler-based non-invasive method for determining dynamic behavior of an aortic valve of a subject, the aortic valve having multiple asymmetric valve leaflets and the method comprising:

receiving Doppler echocardiography images of the subject;

processing the received images to reconstruct a 3D geometry of the valve leaflets;

determining transient pressure boundary conditions for the valve leaflets using a lumped parameter model specific to the subject;

performing a first finite element simulation to determine one or more geometrical parameters for the valve leaflets, wherein the first finite element simulation is based on the reconstructed 3D geometry of the valve leaflets, the determined transient boundary conditions and an initial value of one or more anisotropic stiffness material parameters of the valve leaflets of the aortic valve;

iteratively calibrating the initial value of the one or more anisotropic stiffness material parameters for the subject by comparing the one or more geometrical parameters determined in each iteration with a measured geometrical parameter the one or more geometrical parameters in each iteration determined by further performing the first finite element simulation based on i) the reconstructed 3D geometry of the valve leaflets, ii) the transient boundary conditions determined using the lumped parameter model specific to the subject, and iii) iterative value(s) of the one or more anisotropic stiffness material parameters for the subject; and performing a second finite element simulation, based on the calibrated one or more anisotropic stiffness material parameters, to determine an indicator of the dynamic behavior of the aortic valve.

2. The method of claim 1, wherein the 3D geometry of the valve leaflets is reconstructed by processing parasternal long-axis view and parasternal short-axis view Doppler echocardiography images.

3. The method of claim 2, wherein the 3D geometry of the valve leaflets is reconstructed by measuring a base diameter, a diameter of commissures, a valve height and a length of central coaptation from the parasternal long-axis view Doppler echocardiographic image.

4. The method of claim 2, wherein the 3D geometry of the valve leaflets is reconstructed by measuring multiple leaflet angles from the parasternal short-axis view Doppler echocardiography image.

5. The method of claim 1, wherein the lumped parameter model comprises one or more of a left ventricle sub-model, a left atrium sub-model, an aortic valve sub-model, a mitral valve sub-model, a pulmonary circulation sub-model, and a systemic circulation sub-model.

6. The method of claim 1, wherein the transient pressure boundary conditions comprise a transient pressure difference between a left ventricle of the subject and an aorta of the subject.

7. The method of claim 1, wherein the measured geometrical parameter for the iterative calibration comprises an angular position or a geometric orifice area of the valve leaflets.

8. The method of claim 7, wherein the measured geometrical parameter is measured from a parasternal long-axis view and a parasternal short-axis view Doppler echocardiographic image at the peak systole time frame in which the aortic valve is in its fully open configuration.

9. The method of claim 1, wherein the indicator indicates one or more of a transient 3D distribution of stress and displacement field for the valve leaflets at different time points of a cardiac cycle, a 3D deformed shape of the valve leaflets and a stiffness of the valve leaflets.

10. The method of claim 1, wherein the valve leaflets comprise native valve leaflets or prosthetic valve leaflets.

11. The method of claim 1, further comprising diagnosing, monitoring or prognosing aortic valve stenosis (AS) in the subject based on the indicator.

12. The method of claim 11, wherein the indicator indicates dynamic behavior of each of the valve leaflets.

13. The method of claim 12, wherein the diagnosing, monitoring or prognosing aortic valve stenosis (AS) is conducted pre-intervention or post-intervention.

14. The method of claim 13, wherein the intervention is a transcatheter aortic valve replacement (TAVR).

15. A system for determining dynamic behavior of an aortic valve of a subject, the aortic valve having multiple asymmetric valve leaflets and the system comprising:

a processor; and a memory storing processor-executable instructions, wherein the instruction configure the processor to perform the method of any of claims 1 to 14.

* * * * *